United States Patent
Pahan et al.

(10) Patent No.: US 11,344,524 B2
(45) Date of Patent: May 31, 2022

(54) BRAIN DERIVED PPARα LIGANDS

(71) Applicant: Rush University Medical Center, Chicago, IL (US)

(72) Inventors: Kalipada Pahan, Skokie, IL (US); Avik Roy, Chicago, IL (US)

(73) Assignee: RUSH UNIVERSITY MEDICAL CENTER, Chicago, IL (US)

( * ) Notice: Subject to any disclaimer, the term of this patent is extended or adjusted under 35 U.S.C. 154(b) by 3 days.

(21) Appl. No.: 16/816,524

(22) Filed: Mar. 12, 2020

(65) Prior Publication Data

US 2020/0206177 A1 Jul. 2, 2020

Related U.S. Application Data

(62) Division of application No. 15/736,244, filed as application No. PCT/US2016/037365 on Jun. 14, 2016, now Pat. No. 10,617,664.

(60) Provisional application No. 62/175,871, filed on Jun. 15, 2015.

(51) Int. Cl.
| | |
|---|---|
| *A61K 31/22* | (2006.01) |
| *A61K 31/16* | (2006.01) |
| *G01N 33/68* | (2006.01) |
| *G01N 33/50* | (2006.01) |
| *A61K 31/19* | (2006.01) |
| *A61P 25/28* | (2006.01) |
| *A61P 3/00* | (2006.01) |

(52) U.S. Cl.
CPC ............... *A61K 31/22* (2013.01); *A61K 31/16* (2013.01); *A61K 31/19* (2013.01); *A61P 3/00* (2018.01); *A61P 25/28* (2018.01); *G01N 33/5058* (2013.01); *G01N 33/6896* (2013.01); *G01N 2800/2814* (2013.01); *G01N 2800/2835* (2013.01)

(58) Field of Classification Search
CPC ........ A61K 31/16; A61K 31/19; A61K 31/22; A61P 25/28; A61P 3/00
See application file for complete search history.

(56) References Cited

U.S. PATENT DOCUMENTS

| | | |
|---|---|---|
| 2006/0229265 A1 | 10/2006 | Milburn et al. |
| 2008/0103209 A1 | 5/2008 | Piomelli et al. |
| 2010/0261676 A1 | 10/2010 | Semenkovich et al. |

FOREIGN PATENT DOCUMENTS

| | | |
|---|---|---|
| EP | 3404054 A1 | 11/2018 |
| JP | 2002527496 A | 8/2002 |
| JP | 2005-501817 A | 1/2005 |
| JP | 2005-525313 A | 8/2005 |
| JP | 2008527002 A | 7/2008 |
| JP | 2015-120667 A * | 7/2015 |
| JP | 2015120667 A | 7/2015 |
| WO | 2000023407 A2 | 4/2000 |
| WO | 2001035939 A2 | 5/2001 |
| WO | 2006076681 A2 | 7/2006 |
| WO | 08125805 A1 | 10/2008 |
| WO | 13064579 A1 | 5/2013 |
| WO | 17121916 A1 | 7/2017 |

OTHER PUBLICATIONS

ANO—JP2015120667A-1—English translation (Year: 2015).*
Roy (Cell Rep, Aug. 29, 2013, 4(4), 724-737 (Year: 2013).*
CAS registry—Hexadecanamide (Year: 1984).*
Cabrera et al.; "Increased reactive oxygen species production downregulates peroxisome praliferator-activated alpha pathway in C2C12 skeletal muscle cells"; The Journal of Biological Chemistry, vol. 277; Mar. 22, 2002; pp. 10100-10107.
Campolongo, P. et al.; "Fat-induced satiety factor oleoylethanolamide enhances memory consolidation"; Procedures of the National Academy of Sciences, vol. 106; May 12, 2009; pp. 5027-5031.
Chakravarthy, M.V. et al.; "Identification of a physiologically relevant endogenous ligand for PPARα in liver"; Cell, vol. 138; Aug. 7, 2009; pp. 476-488.
Chakravarthy, M.V. et al.; "Brain fatty acid synthase activates PPARα to maintain energy homeostasis"; The Journal of Clinical Investigation, vol. 117; Sep. 4, 2007; pp. 2539-2552.
Chen, C. et al.; "Inhibition of TNFα-induced adhesion molecule expression by (Z)- (S)-9-octadecenamide, N-(2-hydroxyethyl, 1-methyl)"; European Journal of Pharmacology, vol. 660; 2011; pp. 305-309; Abstract.
Chen, L. et al.; "Oleoylethanolamide, an endogenous PPAR-alpha ligand, attenuates liver fibrosis targeting hepatic stellate cells"; Oncotarget, vol. 6; Dec. 2015; pp. 42530-42540.
Cluny, N.L. et al.; "The identification of peroxisome praliferator-activated receptor alpha-independent effects of oleoylethanolamide on intestingal transit in mice"; Neurogastroenterol Motil, vol. 21; Apr. 1, 2009; pp. 420-429.
Corbett, G.T. et al.; "Activation of peroxisome praliferator-activated receptor alpha stimulates ADAM10-mediated proteolysis of APP"; Procedures National Academy of Sciences, vol. 112; Jul. 7, 2015; pp. 8445-8450.

(Continued)

*Primary Examiner* — Umamaheswari Ramachandran
(74) *Attorney, Agent, or Firm* — Barnes & Thornburg LLP

(57) ABSTRACT

Methods of modulating peroxisome proliferator-activated receptor α (PPARα) activity in a cell in a subject in need thereof are provided. The methods include administering an effective amount of a PPARα ligand to the subject where the PPARα ligand is selected from 3-hydroxy-2,2-dimethyl butyrate (HMB), hexadecananamide (HEX) and 9-octadecenamide (OCT). Methods of treating dementia, neurodegenerative disorders, lysosomal storage diseases and body weight disorders in a subject in need thereof are provided. The methods include administering an effective amount of a PPARα ligand to the subject.

9 Claims, 43 Drawing Sheets
Specification includes a Sequence Listing.

(56) References Cited

OTHER PUBLICATIONS

Dasgupta, S. et al.; "Role of very-late antigen-4 (VLA-4) in myelin basic protein-primed T cell contact-induced expression of proinflammatory cytokines in microglial cells"; Journal of Biological Chemistry, vol. 278; Apr. 10, 2003 pp. 22424-22431.
Fanelli, F. et al.; "Age-dependent roles of peroxisomes in the hippocampus of a transgenic mouse model of Alzheimer's disease"; Molecular Neurodegener, vol. 8; Dec. 2013; 19 pages.
Fang et al.; "20-carboxy-arachidonic acid is a dual activator of peroxisome proliferator-activated receptors alpha and gamma"; Prostaglandins & Other Lipid Mediators, vol. 82; Jan. 2007; pp. 175-184.
Fu, J. et al.; "Oleylethanolamide regulates feeding and body weight through activation of the nuclear receptor PPAR-α"; Nature, vol. 425; Sep. 4, 2003; pp. 90-93.
Fu, J. et al.; "Oleoylethanolamide, an endogenous PPAR-a agonist, lowers body weight and hyperlipidemia in obese rats"; Neuropharmacology, vol. 48; Jun. 1, 2005; pp. 1147-1153.
Ghosh et al.; "Activation of Peroxisome Proliferator-activated Receptor a induces Lysosomal biogenesis in Brain Cells"; The Journal of Biological Chemistry, vol. 290, No. 16; Apr. 17, 2015; pp. 10309-10324.
Ghosh, A. et al.; "Gemfibrozil and fenogibrate, Food and Drug Administration-approved lipid-lowering drugs, up-regulate tripeptidyl-peptidase 1 in brain cells via peroxisome proliferator-activated receptor a: implications for late infantile Batten disease therapy"; Journal of Biological Chemistry, vol. 287; Nov. 9, 2012; p. 38922-38935.
Ghosh, A. et al.; "Selective inhibition of NF-kappβ activation prevents dopaminergic neuronal loss in a mouse model of Partkinson's disease"; Procedures of the National Academy of Sciences, vol. 104; Nov. 20, 2007; pp. 18754-18759.
Giulian, D. et al.; "Characterization of ameboid microglia isolated from developing mammalian brain"; Journal of Neuroscience, vol. 6; Aug. 1, 1986; pp. 2163-2178.
Gocke, A.R. et al.; "Transcriptional modulation of the immune response by peroxisome proliferator-activated receptor-a agonists in autoimmune disease"; The Journal of Immunology, vol. 182; Apr. 1, 2009; pp. 4479-4487.
Gorini, A. et al.; "Energy metabolism of synaptosomal subpopulations from different neuronal systems of rat hippocampus: effect of L-acetylcarnitine administration in vivo"; Neurochem Research, vol. 24; May 1, 1999; pp. 617-624.
Gronemeyer, H. et al.; "Principles for modulation of the nuclear receptor superfamily"; Nature Reviews Drug Discovery, vol. 3; Nov. 2004; pp. 950-964.
Jana, M. et al.; "A simplified method for isolating highly purified neurons, oligodendrocytes, astrocytes, and microglia from the same human fetal brain tissue"; Neurochemistry Research, vol. 32; Dec. 1, 2007; pp. 2015-2022.
Harris, K.M. et al.; "Three-dimensional structure of dendritic spines and synapses in rat hippocampus (CA1) at postnatal day 15 and adult ages: implications for the maturation of synaptic physiology and long-term potentiation" Journal of Neuroscience, vol. 12; Jul. 1992; pp. 2685-2705.
Huitron-Resendiz, S. et al.; "Effect of oleamide on sleep and its relationship to blood pressure, body temperature and locomotor activity in rats"; Experimental Neurology, vol. 172; Nov. 1, 2001; DD. 235-243.
Im, W. et al.; "An implicit membrane generalized born theory for the study of structure, stability, and interactions of membrane proteins"; Biophysical Journal, vol. 85; Nov. 1, 2003; pp. 2900-2918.
Issemann, I. et al.; "Activation of a member of the steroid hormone receptor superfamily by peroxisome proliferators" Nature, vol. 347; Oct. 1990; pp. 645-650.
Kainu, T. et al.; "Localization of the peroxisome proliferator-activated receptor in the brain"; Neuroreport, vol. 5; Dec. 1994; pp. 2481-2485.

Kauer, J.A. et al.; "NIMDA application potentiates synaptic transmission in the hippocampus"; Nature, vol. 334, Jul. 1988; pp. 250-252.
Keller, H. et al.; "Fatty acids and retinoids control lipid metabolism through activation of peroxisome proliferator-activated receptor-retinoid X receptor heterodimers"; Proceedings of the National Academy of Sciences, vol. 90; Mar. 1993; pp. 2160-2164.
Lehmann, J.M. et al.; "Peroxisome proliferator-activated receptors alpha and gamma are activated by indomethacin and other non-steroidal anti-inflammatory drugs"; The Journal of Biological Chemistry, vol. 272; Feb. 7, 1997; pp. 3406-3410.
LoVerme, J. et al.; "The search for the palmitoylethanolamide receptor"; Life Sciences, vol. 77; 2005; pp. 1685-1698.
Melis, M. et al.; "Physiological role of peroxisome proliferator-activated receptors type alpha on dopamine systems"; CNS & Neurological Disorders—Drug Targets, vol. 12; Feb. 1, 2013; pp. 70-77.
Mulkey, R.M. et al.; "An essential role for protein phosphatases in hippocampal long-term depression"; Science, vol. 261; Aug. 20, 1993; pp. 1051-1055.
Narala, V.R. et al.; "Leukotriene B4 is a physiologically relevant endogenous peroxisome proliferator-activated receptor-alpha agonist"; Journal of Biologiceal Chemistry, vol. 285; Apr. 16, 2010; pp. 22067-22074.
Raso, G.M. et al.; "N-Palmitoylethanolamide protects the kidney from hypertensive injury in spontaneously hypertensive rats via inhibition of oxidative stress"; Pharmacological Research, vol. 76; Oct. 2013; pp. 67-76.
Roy, A. et al.; "Enhancement of morphological plasticity in hippocampal neurons by a physically modified saline via phosphatidylinositol-3 kinase"; PLoS One, vol. 9; Jul. 9, 2014; 15 pages.
Roy, A. et al.; "Regulation of cyclic AMP response element binding and hippocampal plasticity-related genes by peroxisome proliferator-activated receptor a"; Cell Reports, vol. 4; Aug. 29, 2013; pp. 724-737.
Roy, A. et al.; "Up-regulation of microglial CD11b expression by nitric oxide"; Journal of Biological Chemistry, vol. 281; May 26, 2006; pp. 14971-14980.
Roy, A. et al.; "HMG-CoA Reductase Inhibitors Bind to PPARalpha to Upregulate Neurotrophin Expression in the Brain and Improve Memory in Mice"; Cell Metab, vol. 22; 2015 pp. 253-265.
Saha, R.N. et al.; "TNF-alpha preconditioning protects neurons via neuron-specific up-regulation of CREB-binding protein"; The Journal of Immunology, vol. 183; Jul. 13, 2009; pp. 2068-2078.
Saha, R.N. et al.; "Differential regulation of Mn-superoxide dismutase in neurons and astroglia by HIV-1 gp120: Implications for HIV-associated dementia"; Free Radical Biology and Medicine, vol. 42; Jun. 2007; pp. 1866-1878.
Schoonjans, K. et al.; "Induction of the acyl-coenzyme A synthetase gene by fibrates and fatty acids is mediated by a peroxisome proliferator response element in the C promoter"; Journal of Biological Chemistry, vol. 270; Aug. 18, 1995; pp. 19269-19276.
International Search Report completed Aug. 23, 2016 for International Application No. PCT/US2016/037365.
Written Opinion completed Aug. 23, 2016 for International Application No. PCT/US2016/037365.
International Preliminary Report on Patentability dated Dec. 19, 2017 for International Application No. PCT/US2016/037365.
Koichi Takao et al.; "Synthesis and Evaluation of Fatty Acid Amides on the iN/i-Oleoylethanolamide-Like Activation of Peroxisome Proliferator Activated Receptor [alpha]"; Chemical and Pharmaceutical Bulletin, vol. 63, No. 4; Jan. 2015; pp. 278-285.
Burris, Nature Chemical Biology, 2016, p. 993-994 (Year: 2016).
Roy et al, Nature Chemical Biology, Dec. 2016 (Year: 2016).
Tyagi et al., J Adv Pharm Technol Res. Oct.-Dec. 2011; 2(4): 236-240 (Year: 2011).
Ezzili et al., "Fatty Acid Amide Signaling Molecules," Bioorganic & Medicinal Chemistry Letters, Pergamon, Amsterdam, NL, vol. 20, No. 20, (2010), pp. 5959-5968.
Capasso et al., "Fatty Acid Amide Hydrolase Controls Mouse Intestinal Motility in Vivo," Gastroenterology, W.B. Saunders Co., US, vol. 129, No. 3, (2005), pp. 941-951.

(56) References Cited

OTHER PUBLICATIONS

Hiley et al., "Oleamide: A Fatty Acid Amide Signaling Molecule in the Cardiovascular System?: Oleamide" Cardiovascular Drug Reviews, vol. 25, No. 1, (2007), pp. 46-60.
Lin et al., "Differential Proteomic Analysis of the Anti-Depressive Effects of Oleamide in a Rat Chronic Mild Stress Model of Depression," Pharmacology Biochemistry and Behavior, vol. 131, (2015), pp. 77-86.
Ano et al., "Preventive Effects of a Fermented Dairy Product against Alzheimer's Disease and Identification of a Novel Oleamide with Enhanced Microglial Phagocytosis and Anti-Inflammatory Activity," PLOS ONE, vol. 10, No. 3, (2015), p. e0118512.
LoVerme et al., "The Nuclear Receptor Peroxisome Proliferator-Activated Receptor-alpha Mediates the Anti-Inflammatory Actions of Palmitoylethanolamide," Molecular Pharmacology, vol. 67, No. 1, (2005), pp. 15-19.
Guo et al., "Chemical Composition, Antifungal and Antitumor Properties of Ether Extracts of Scapania verrucosa Heeg and its Endophytic Fungus Chaetomium fusiforme," Molecules, vol. 13, (2008), pp. 2114-2125.
Uchiyama et al., "The Absorption, Distribution, Metabolism and Excretion after Single-Dose Administration in in-the-living-body moving state: Rat of Hyperlipemia Medicine Simvastatin," Pharmacokinetics and Metabolism, vol. 5, No. 2, (1990), pp. 133-149.

\* cited by examiner

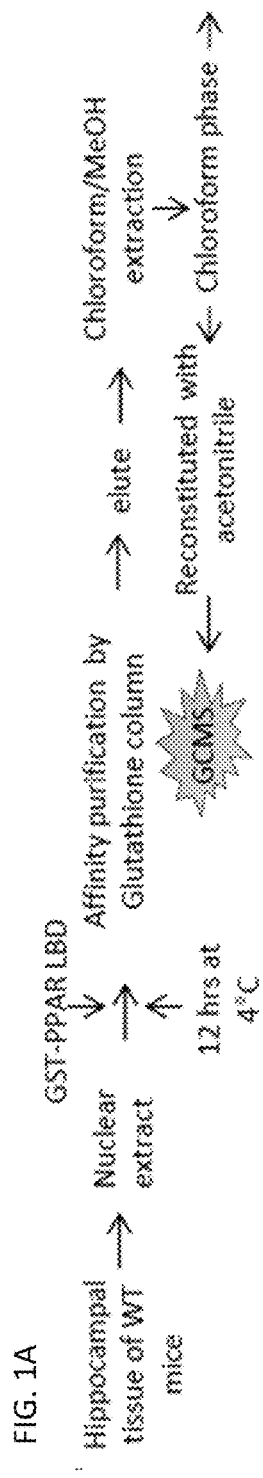
FIG. 1A
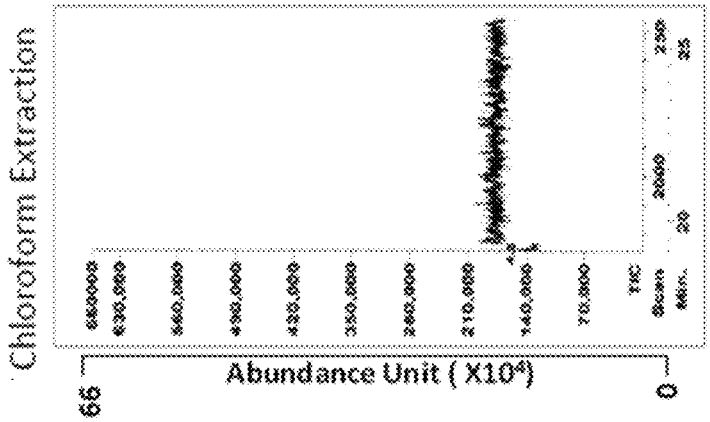
FIG. 1E
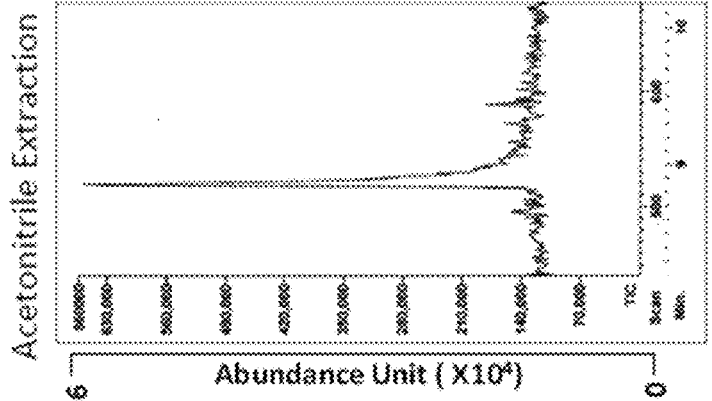
FIG. 1D
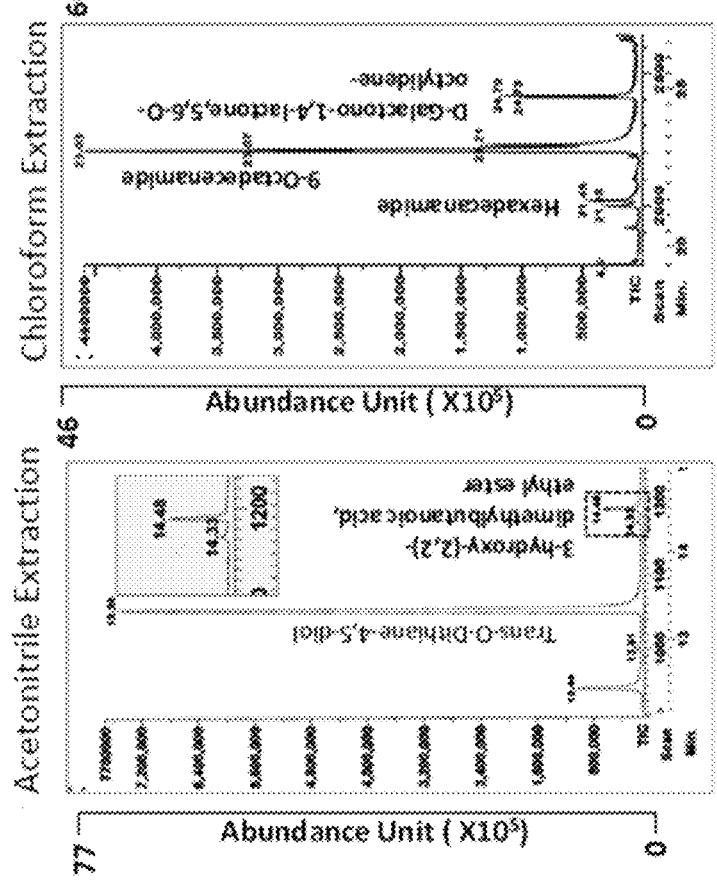
FIG. 1C
FIG. 1B

FIG. 1F
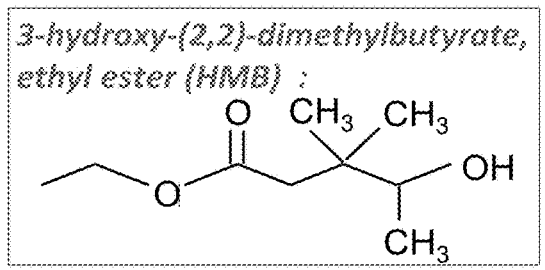
FIG. 1G
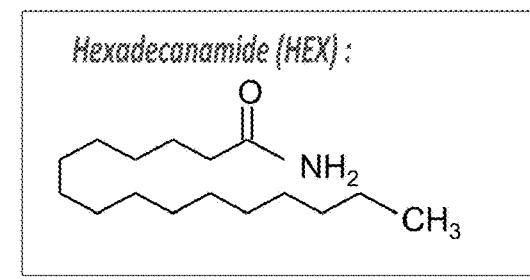
FIG. 1H
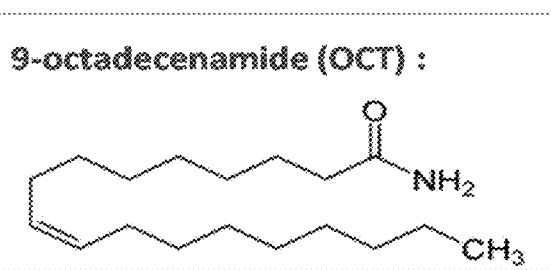
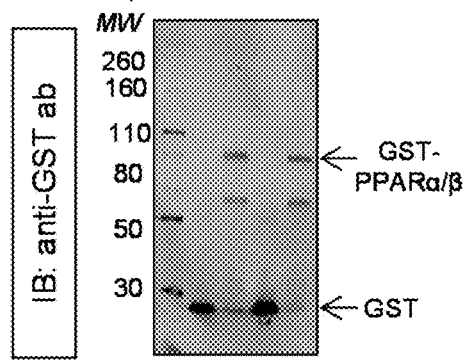
FIG. 1I
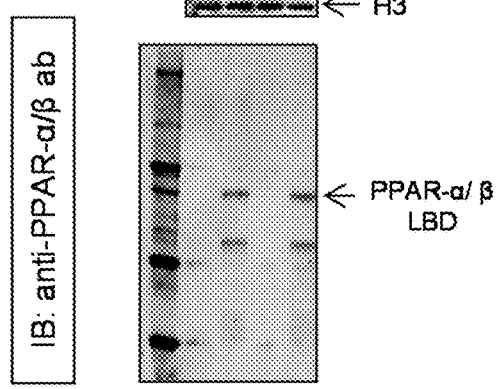
FIG. 1J FIG. 1K
FIG. 1L
Chloroform Extraction :
Chloroform Extraction :
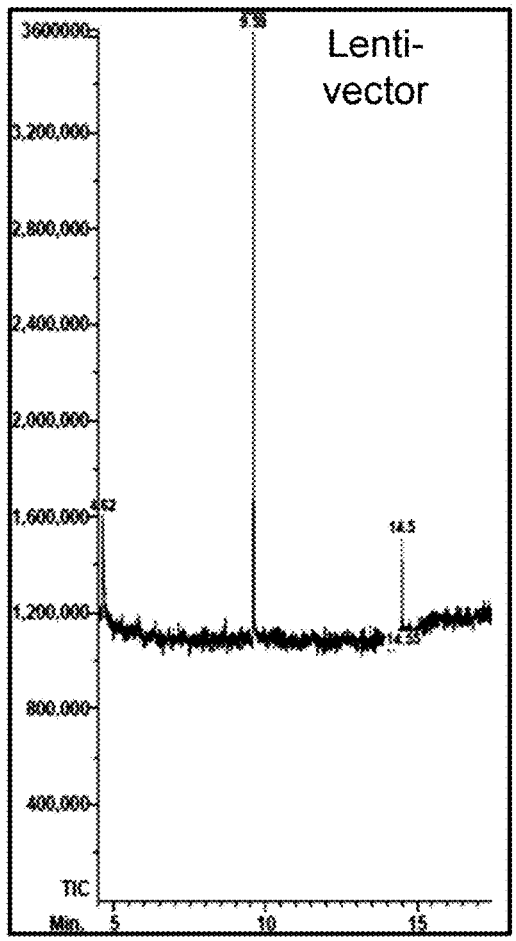
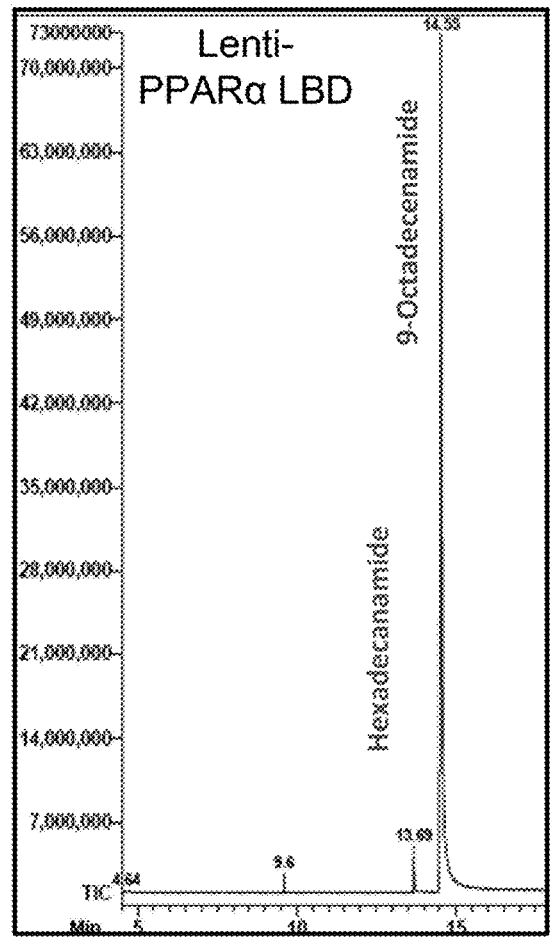
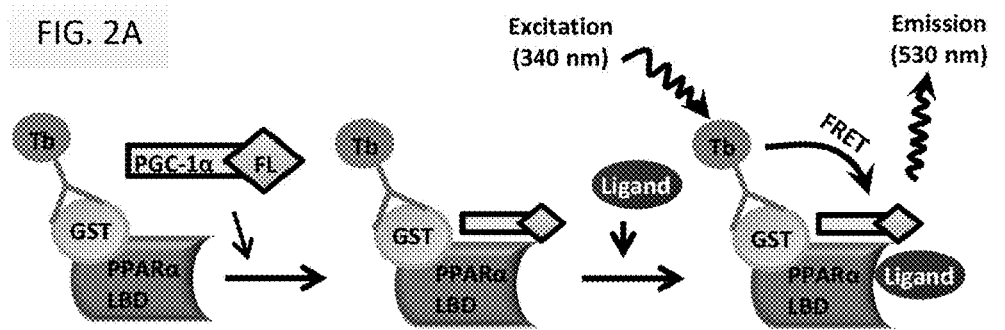

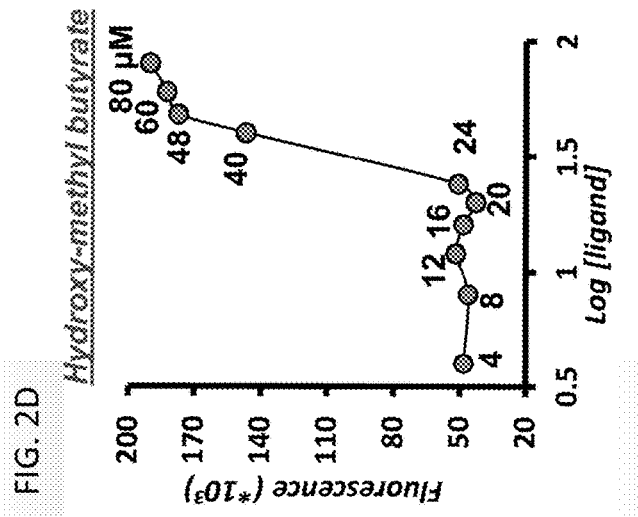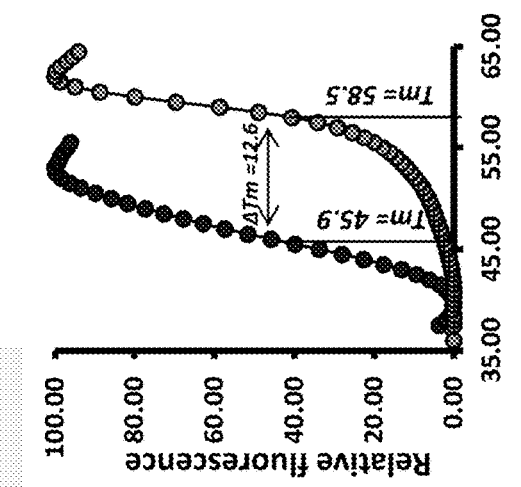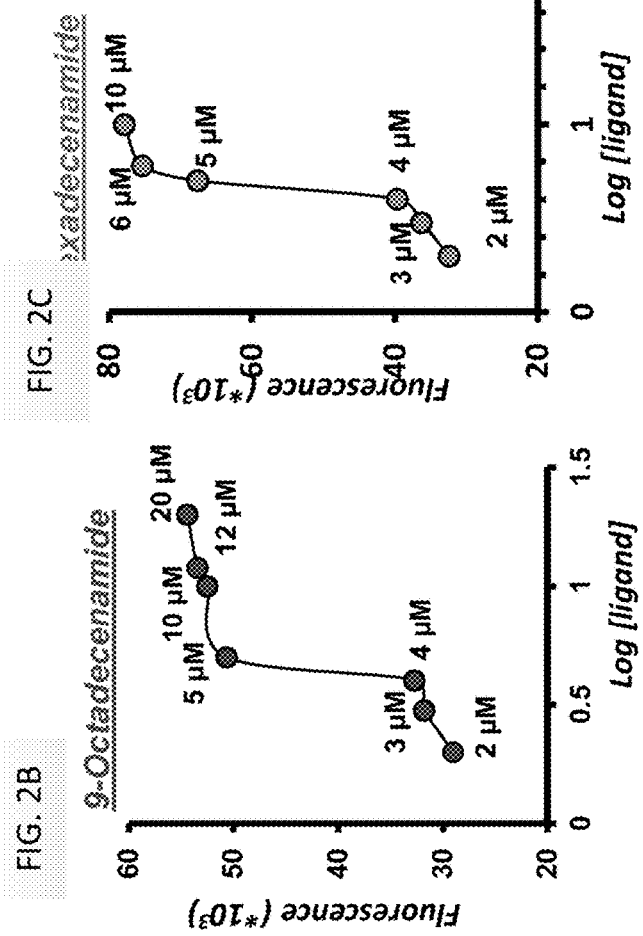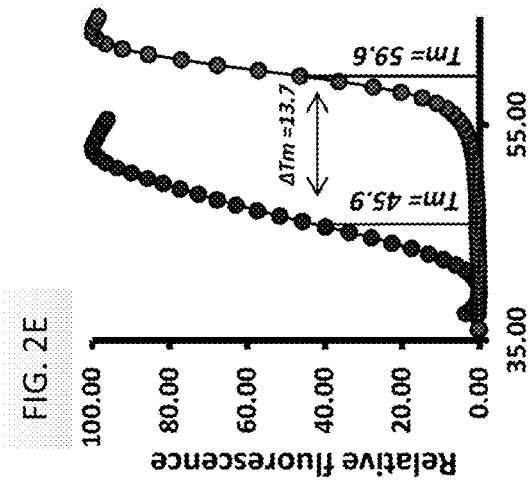

FIG. 3A
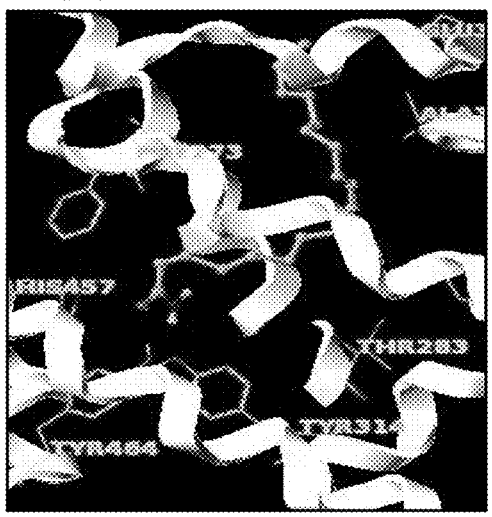
FIG. 3B
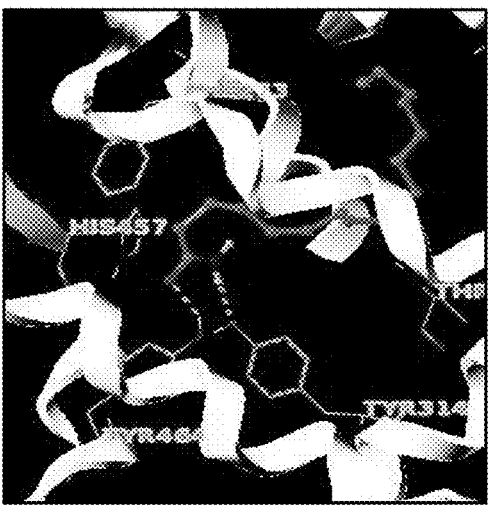
FIG. 3C
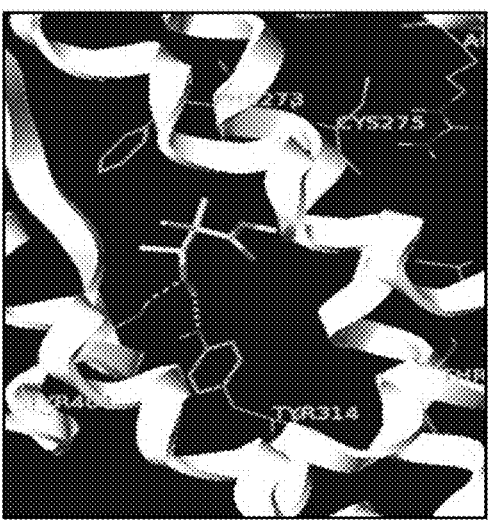
FIG. 3D
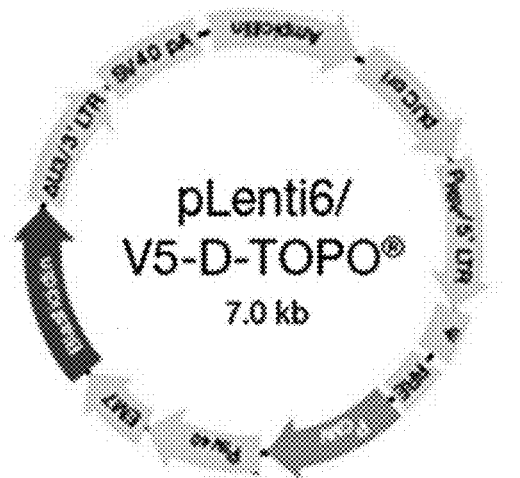
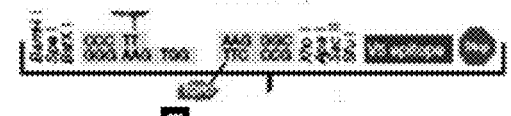
**FL*Ppara***
             314   464
.....K Y G V Y.......Y R D.....
.....AAGTACGGTGTGTAT...TACAGAGAC....
**Y314D *Ppara***
             314   464
.....K Y G V D.......Y R D.....
.....AAGTACGGTGTGGAT...TACAGAGAC....
**Y464D *Ppara***
             314   464
.....K Y G V Y.......D R D.....
.....AAGTACGGTGTGTAT...GACAGAGAC....
**Y314D/Y464D *Ppara***
             314   464
.....K Y G V D.......D R D.....
.....AAGTACGGTGTGGAT...GACAGAGAC....

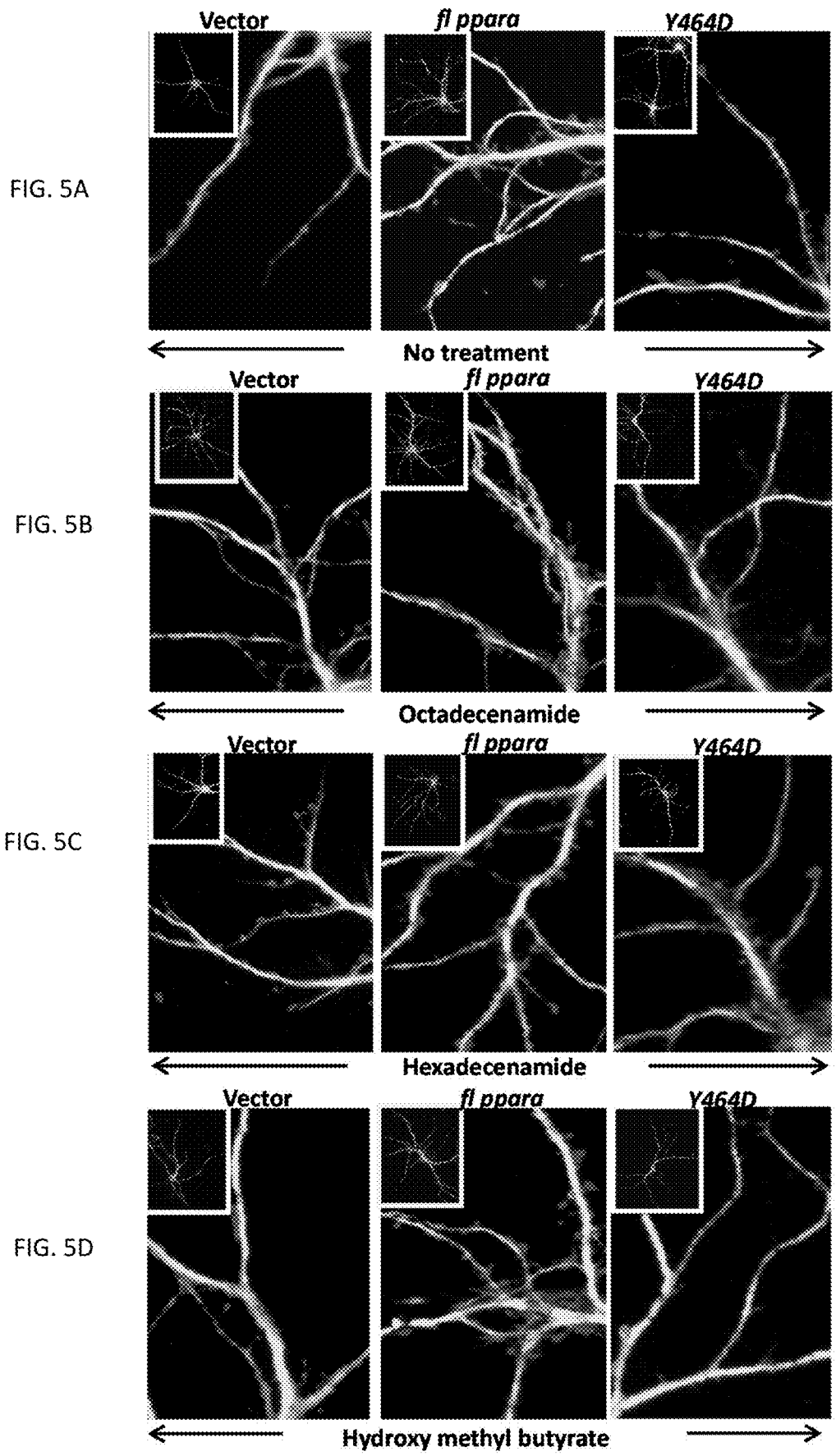

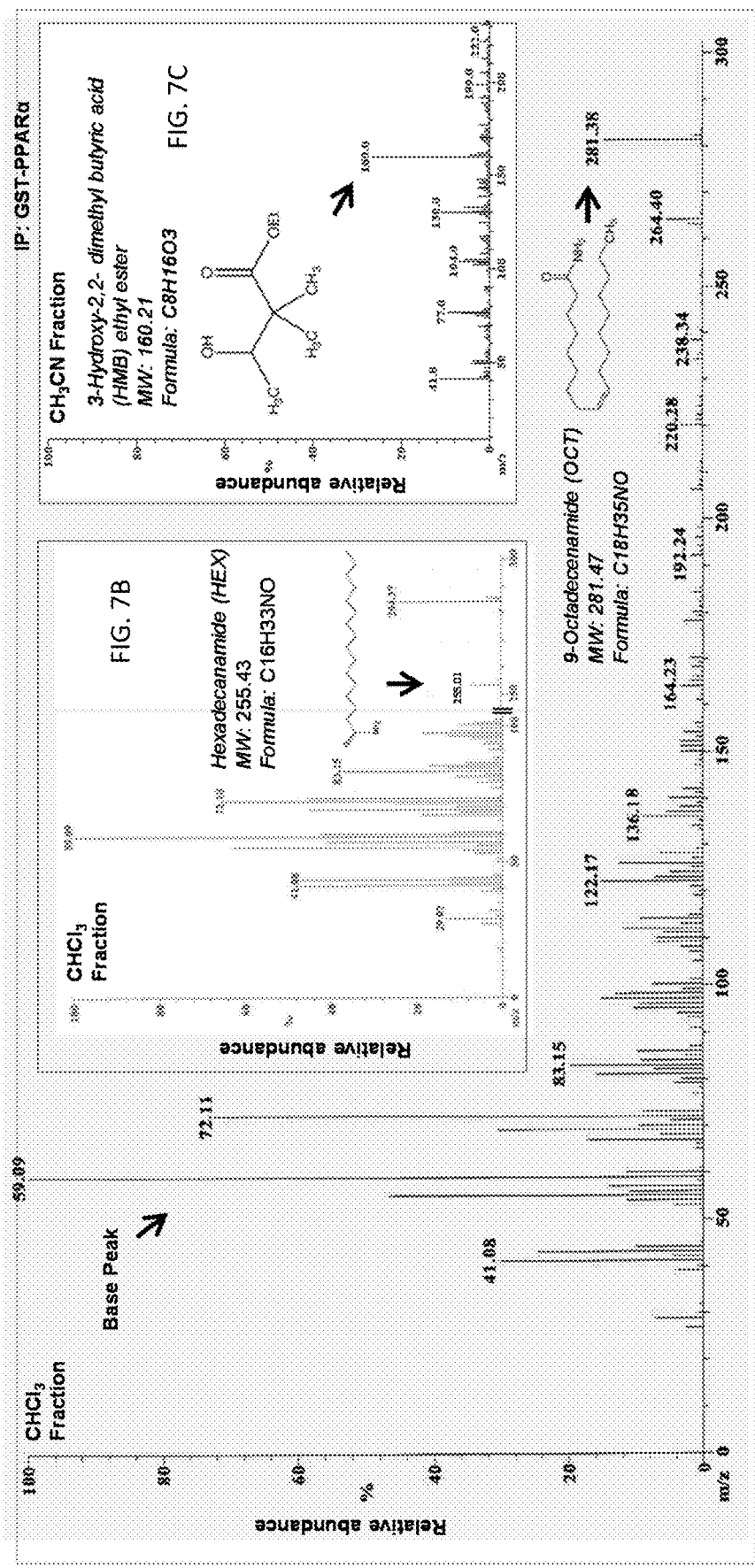

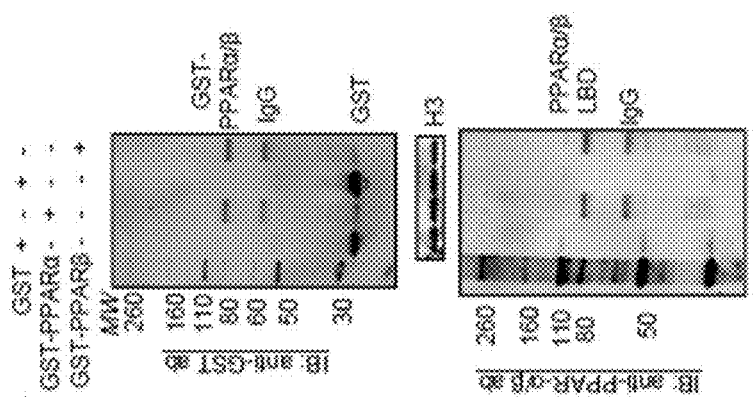
FIG. 7F
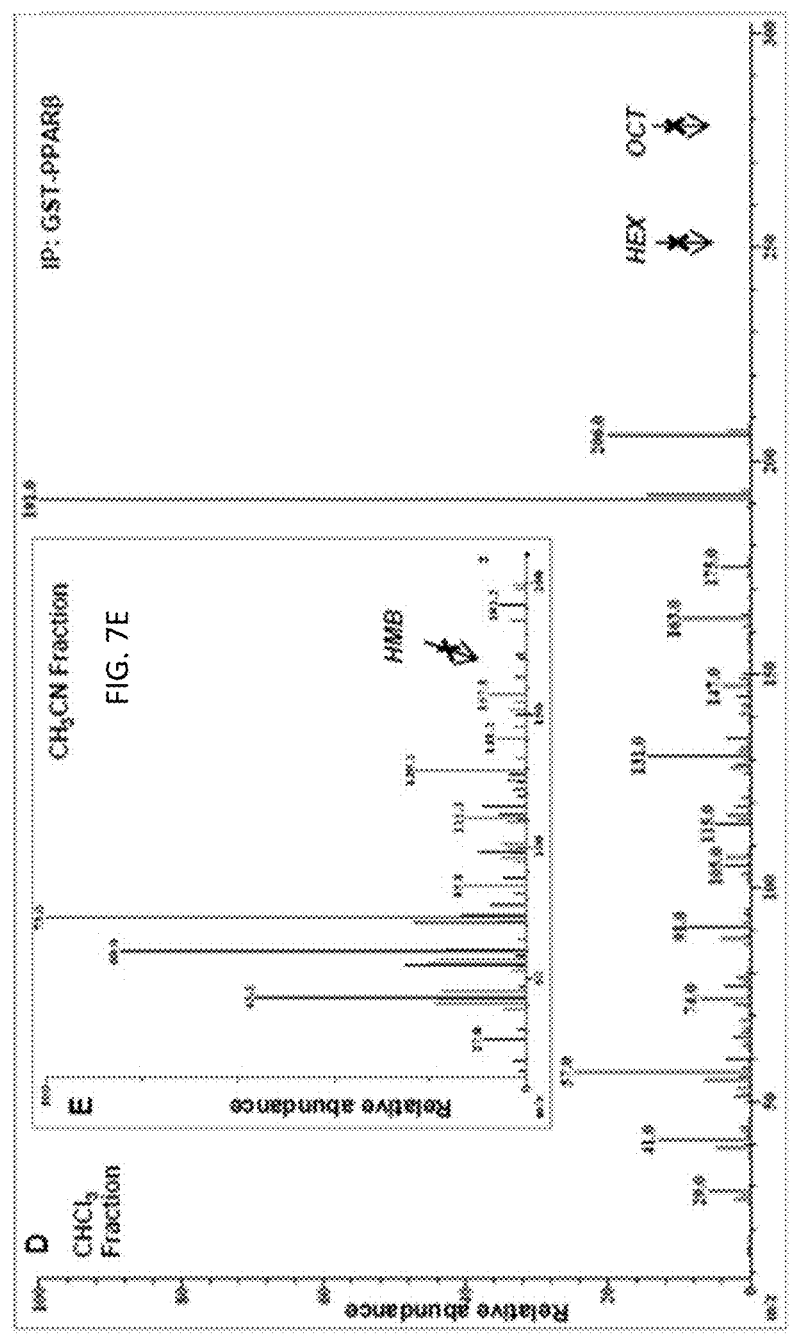
FIG. 7D
FIG. 7E

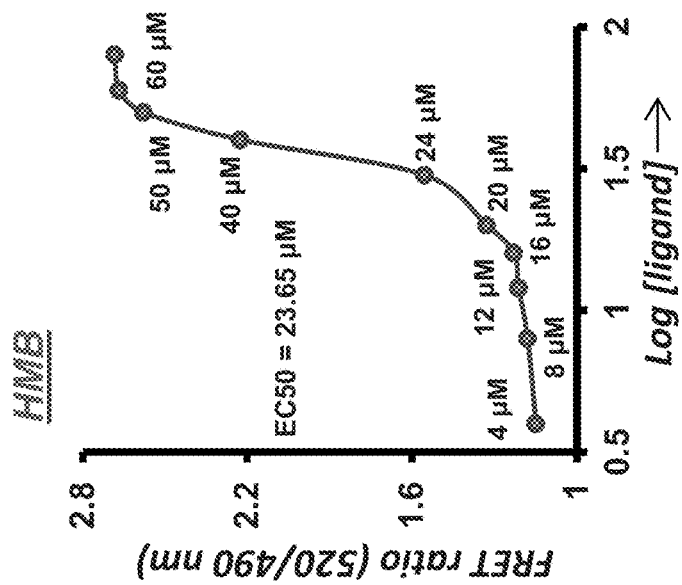
FIG. 8C HMB
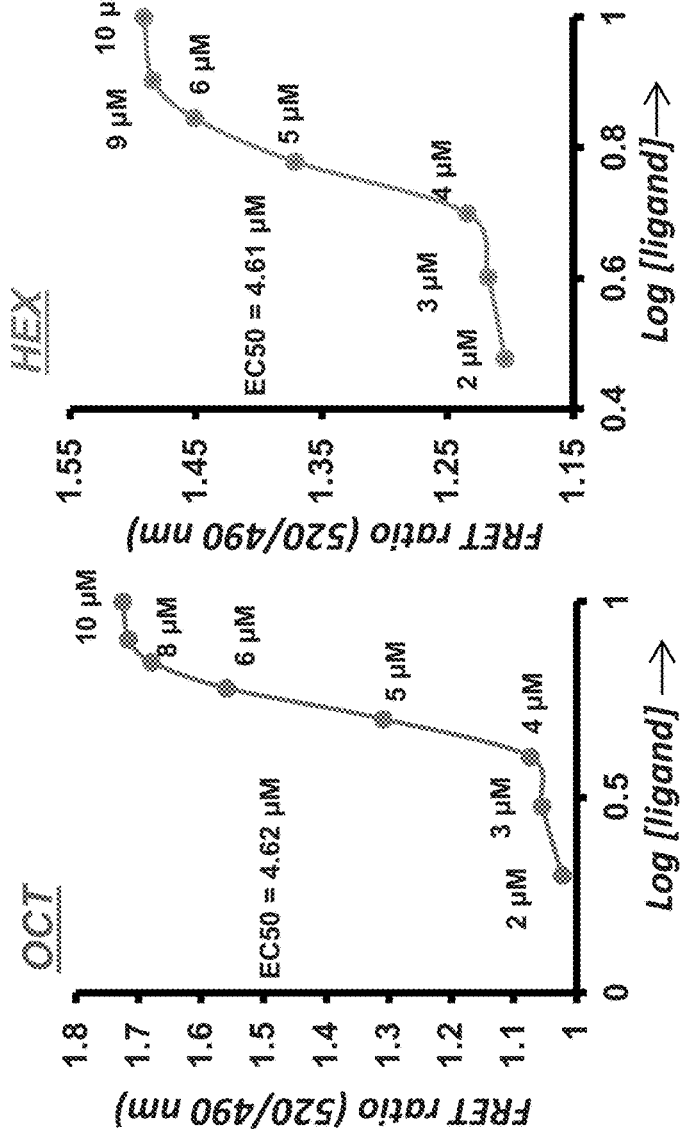
FIG. 8B HEX
FIG. 8A OCT

Grey-Carbon; Cyan-Hydrogen; Red-Oxygen; Yellow-Sulfur; Blue-Nitrogen
FIG. 9A
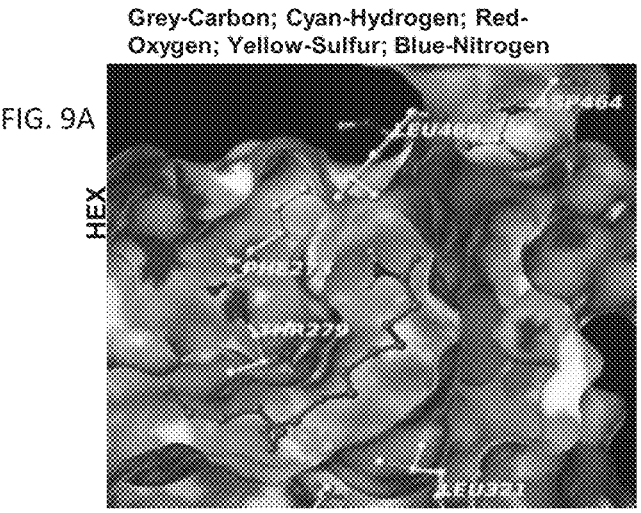
FIG. 9B
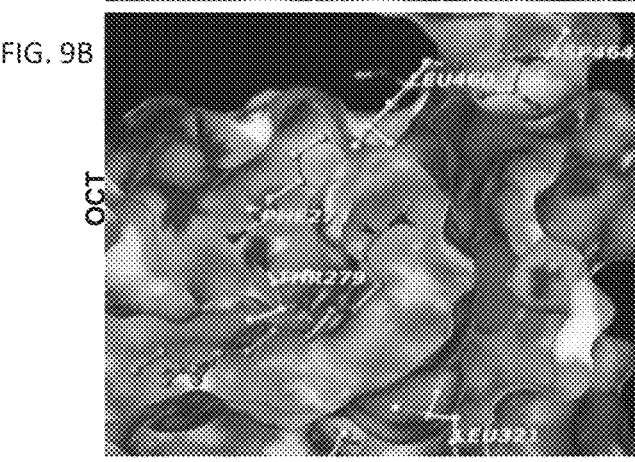
FIG. 9C
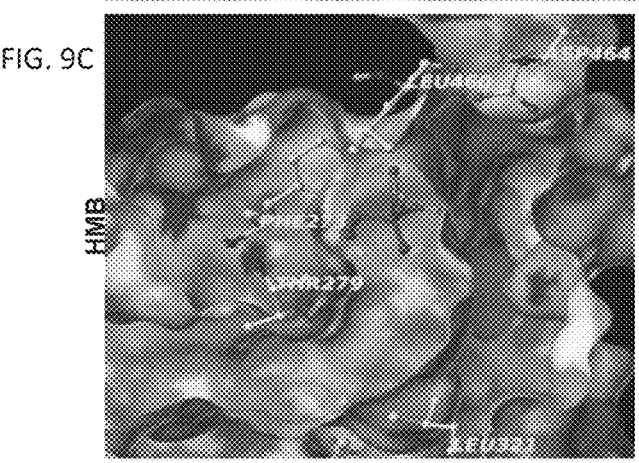
FIG. 9D
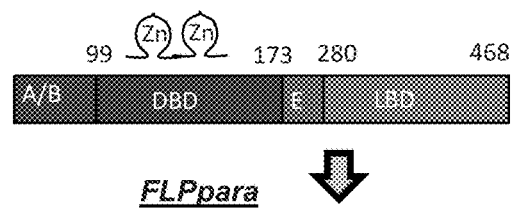
*FLPpara*
Y314D Ppara
314   464
.....K Y G V D......Y R D.....
..AAGTACGGTGTGGAT... TACAGAGAC...
Y464D Ppara
314   464
.....K Y G V Y......D R D.....
..AAGTACGGTGTGTAT... GACAGAGAC...
Y314D/Y464D Ppara
314   464
.....K Y G V D......D R D.....
..AAGTACGGTGTGGAT... GACAGAGAC...
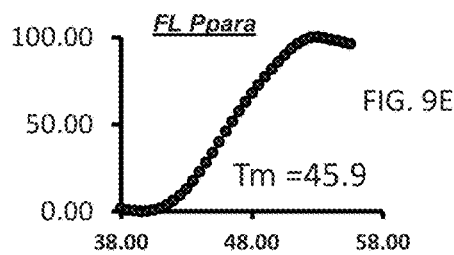
*FL Ppara*
Tm =45.9
FIG. 9E
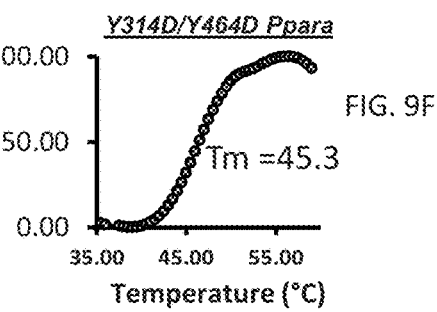
*Y314D/Y464D Ppara*
Tm =45.3
FIG. 9F
Temperature (°C)

GFP-Y314DPpara + αKO neurons

GFP-Y464DPpara + αKO neurons

GFP-Y314D/Y464DPpara + αKO neurons

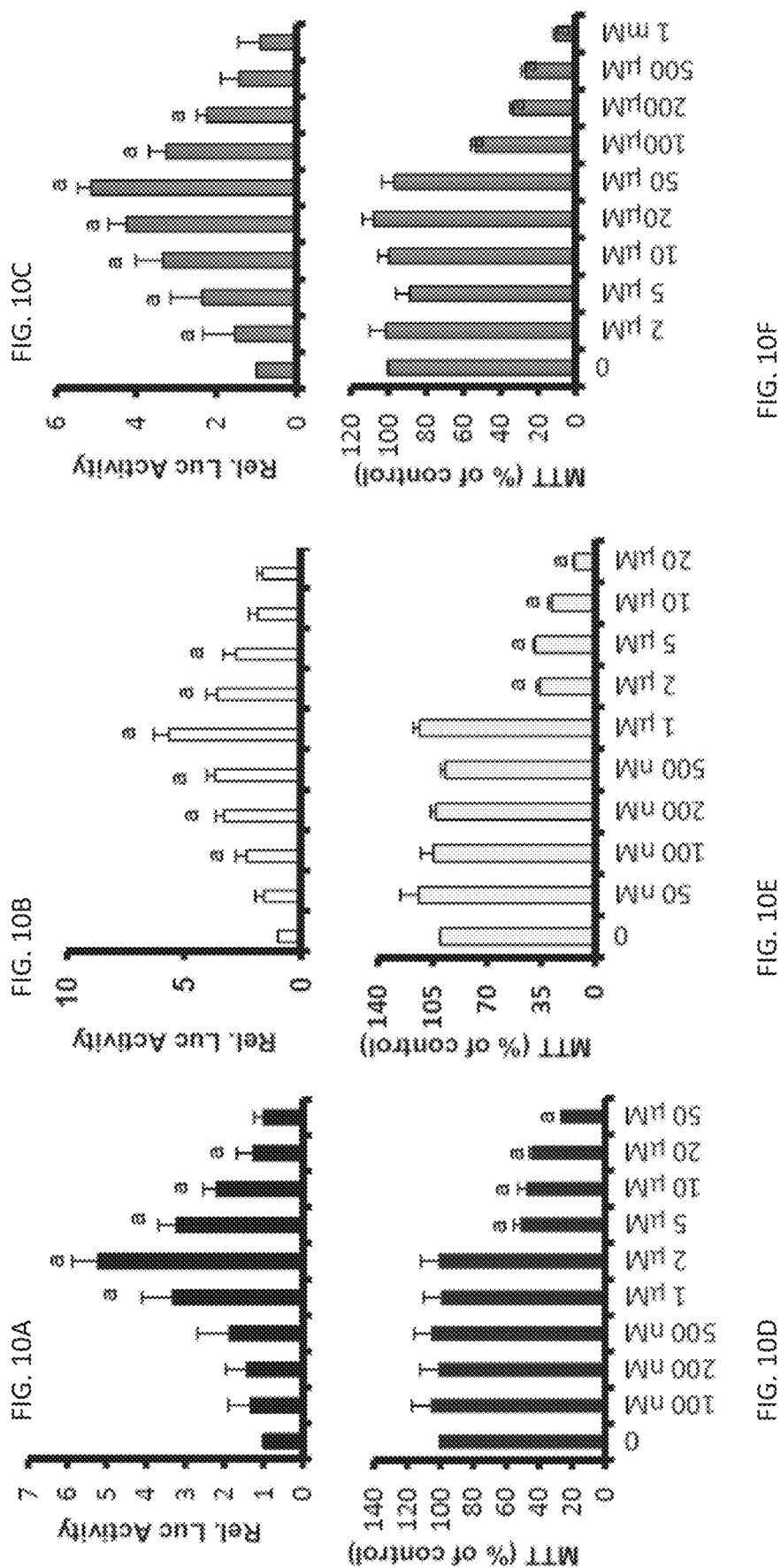

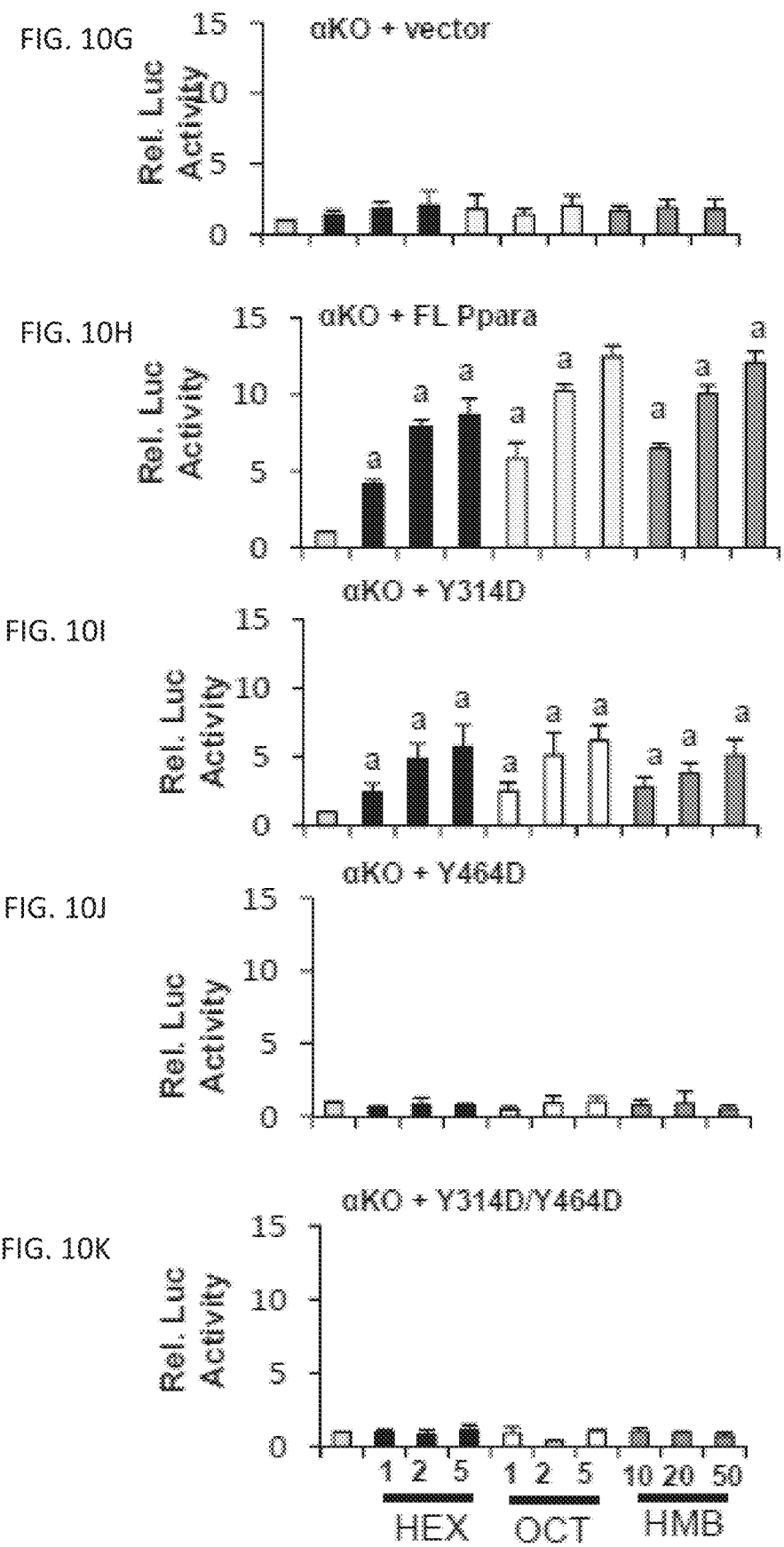

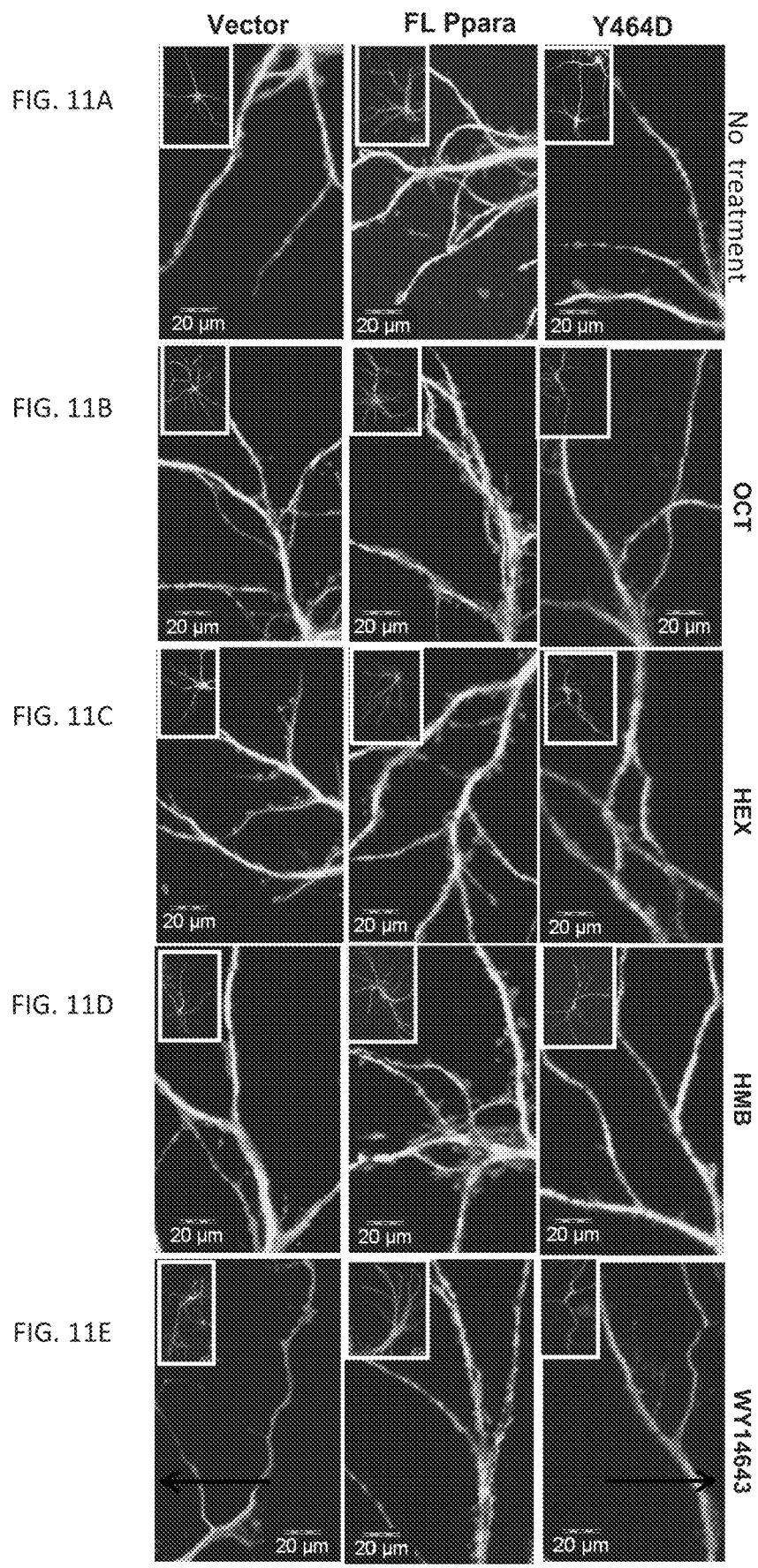

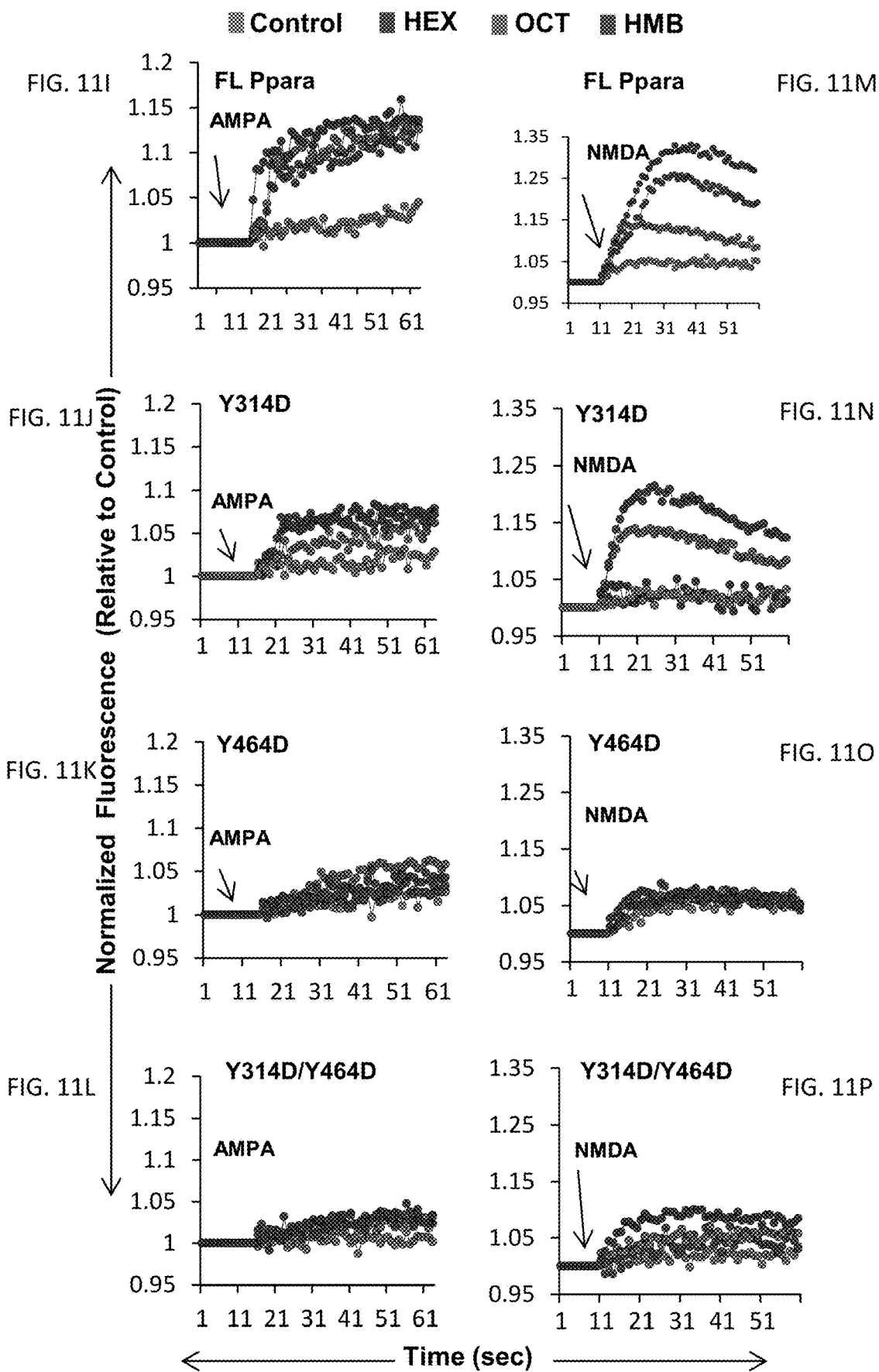

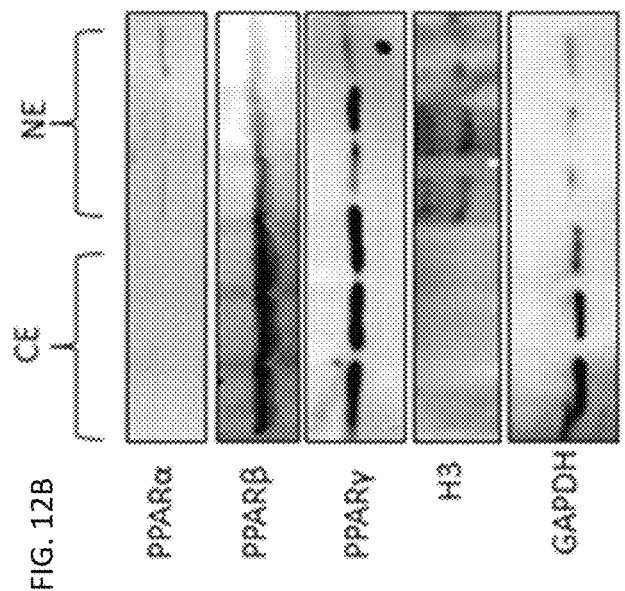
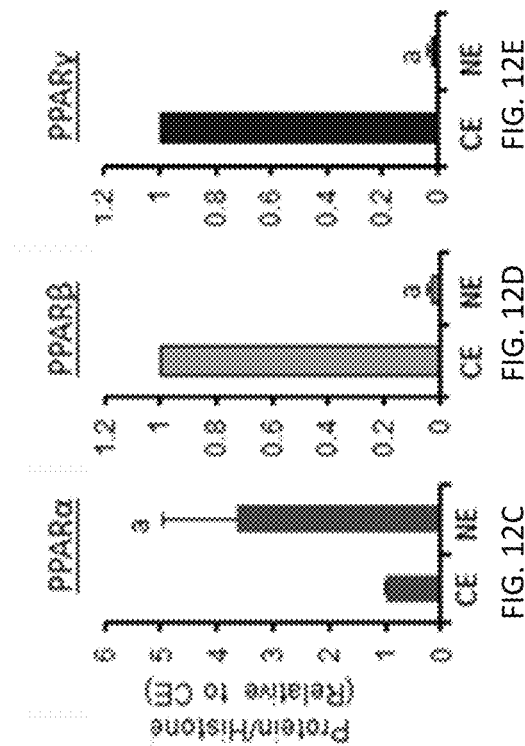
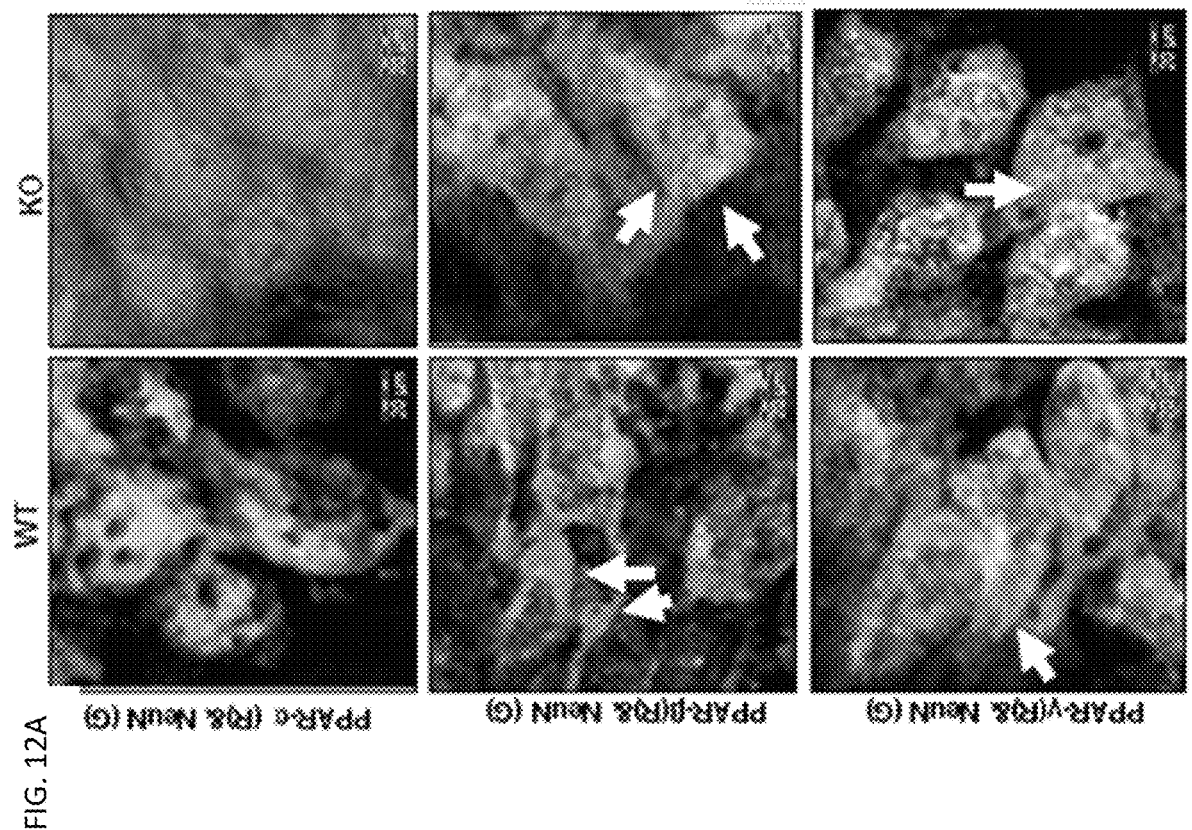
FIG. 12A
FIG. 12B
FIG. 12C
FIG. 12D
FIG. 12E

FIG. 14A
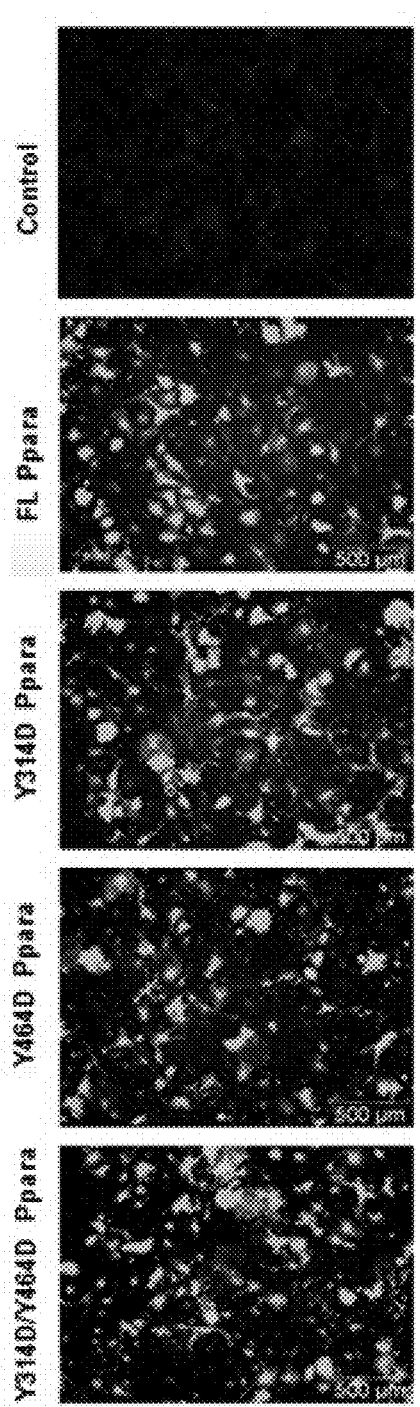
FIG. 14B
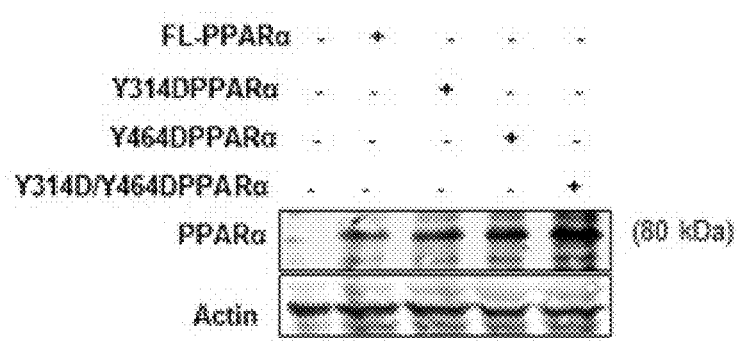
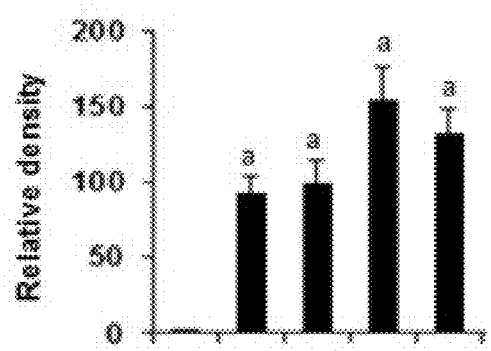
FIG. 14C

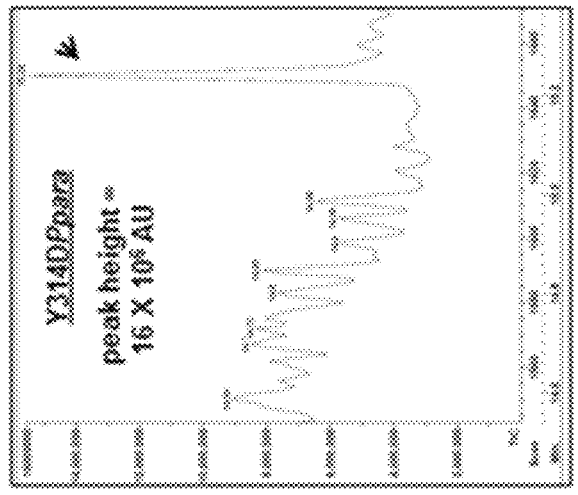
FIG. 15A
FIG. 15B
FIG. 15C
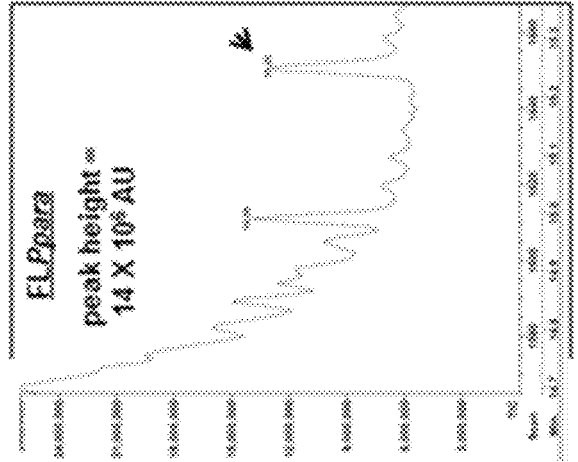
FIG. 15D
FIG. 15E
FIG. 15F

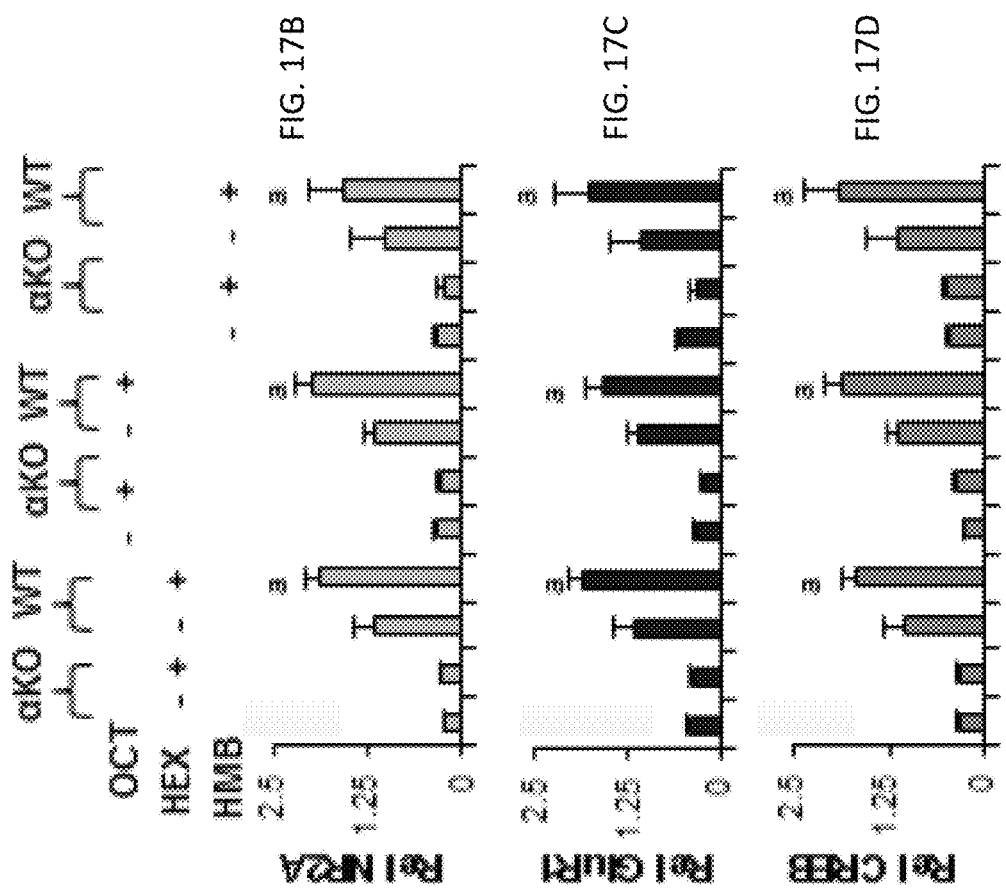
FIG. 17B
FIG. 17C
FIG. 17D
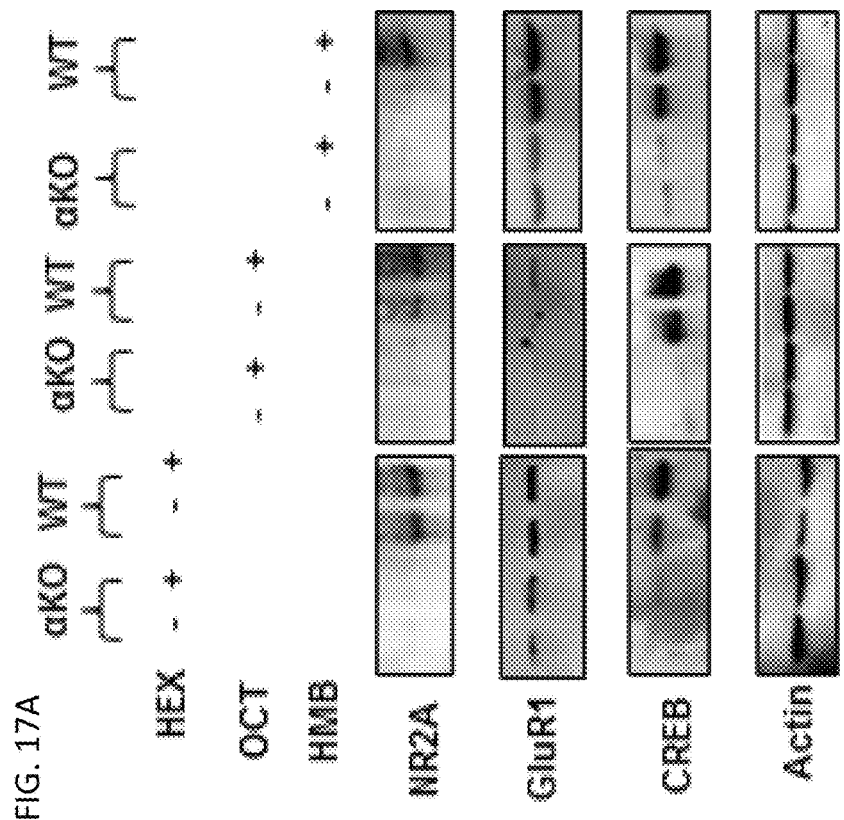
FIG. 17A

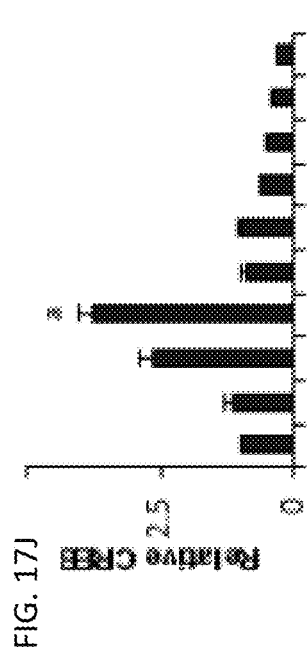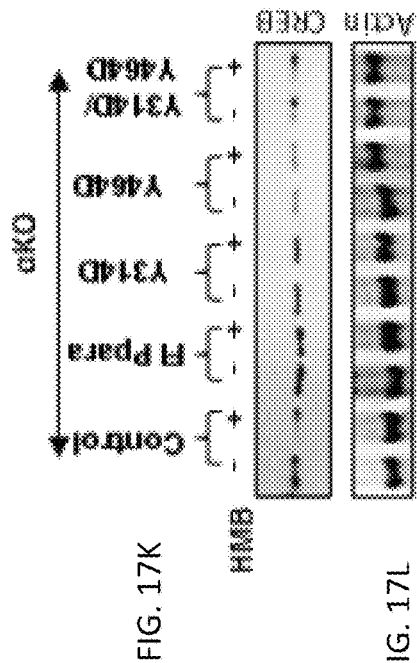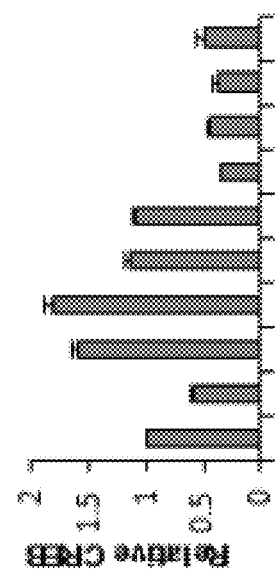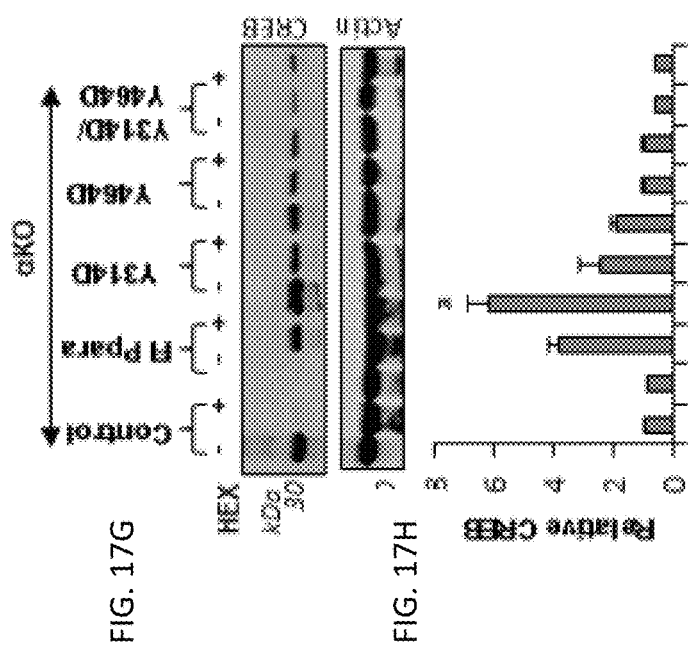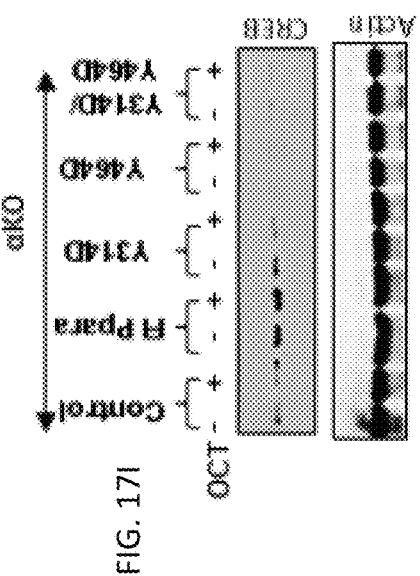

SEQUENCE LISTING

```
<160> NUMBER OF SEQ ID NOS: 9

<210> SEQ ID NO 1
<211> LENGTH: 25
<212> TYPE: DNA
<213> ORGANISM: Artificial Sequence
<220> FEATURE:
<223> OTHER INFORMATION: iNOS forward primer

<400> SEQUENCE: 1
cccttccgaa gtttctggca gcagc                                    25

<210> SEQ ID NO 2
<211> LENGTH: 25
<212> TYPE: DNA
<213> ORGANISM: Artificial Sequence
<220> FEATURE:
<223> OTHER INFORMATION: iNOS reverse primer

<400> SEQUENCE: 2
ggctgtcaga gcctcgtggc tttgg                                    25

<210> SEQ ID NO 3
<211> LENGTH: 21
<212> TYPE: DNA
<213> ORGANISM: Artificial Sequence
<220> FEATURE:
<223> OTHER INFORMATION: IL-1B forward primer

<400> SEQUENCE: 3
ctccatgagc tttgtacaag g                                        21

<210> SEQ ID NO 4
<211> LENGTH: 20
<212> TYPE: DNA
<213> ORGANISM: Artificial Sequence
<220> FEATURE:
<223> OTHER INFORMATION: IL-1B reverse primer

<400> SEQUENCE: 4
tgctgatgta ccagttgggg                                          20

<210> SEQ ID NO 5
<211> LENGTH: 21
<212> TYPE: DNA
<213> ORGANISM: Artificial Sequence
<220> FEATURE:
<223> OTHER INFORMATION: MBP forward primer

<400> SEQUENCE: 5
tggagagatt caccgaggag a                                        21

<210> SEQ ID NO 6
<211> LENGTH: 21
<212> TYPE: DNA
<213> ORGANISM: Artificial Sequence
<220> FEATURE:
<223> OTHER INFORMATION: MBP reverse primer

<400> SEQUENCE: 6
tgaagctcgt cggactctga g                                        21

<210> SEQ ID NO 7
<211> LENGTH: 20
<212> TYPE: DNA
<213> ORGANISM: Artificial Sequence
```

```
-continued

<220> FEATURE:
<223> OTHER INFORMATION: GAPDH forward primer

<400> SEQUENCE: 7
ggtgaaggtc ggtgtgaacg                                                   20

<210> SEQ ID NO 8
<211> LENGTH: 20
<212> TYPE: DNA
<213> ORGANISM: Artificial Sequence
<220> FEATURE:
<223> OTHER INFORMATION: GAPDH reverse primer

<400> SEQUENCE: 8
ttggctccac ccttcaagtg                                                   20

<210> SEQ ID NO 9
<211> LENGTH: 13
<212> TYPE: DNA
<213> ORGANISM: Artificial Sequence
<220> FEATURE:
<223> OTHER INFORMATION: Consensus PPRE

<400> SEQUENCE: 9
aggtcaaagg aca                                                          13
```

BRAIN DERIVED PPARα LIGANDS

RELATED APPLICATIONS

This application is a division of application Ser. No. 15/736,244, filed Dec. 13, 2017, which claims the benefit under 35 U.S.C. § 371 of International Application No. PCT/US2016/037365, filed Jun. 14, 2016, which claims the benefit of U.S. Provisional Application No. 62/175,871 filed Jun. 15, 2015; which are incorporated by reference herein in their entirety.

SEQUENCE LISTING

The instant application contains a Sequence Listing which has been submitted electronically in ASCII format and is hereby incorporated by reference in its entirety. The ASCII copy, created on Jun. 13, 2016, is named 42960-313354_Sequence Listing_ST25.txt and is 2 KB in size.

BACKGROUND

Peroxisome proliferator-activated receptor α or PPARα belongs to a class of nuclear hormone receptors[1] that participates in a diverse range of biological functions including control of fatty acid transport and catabolism[2], anti-inflammation[3], immuno-modulation[4], and anti-oxidation[5]. However, in a recent study[6], it has been shown that PPARα also plays an important role in the modulation of synaptic function in hippocampus via transcriptional upregulation of CREB. It has also been delineated that activation of PPARα in hippocampal neurons leads to the increase in ADAM10 transcription and subsequent non-amyloidogenic proteolysis of APP[21]. These reports highlight a lipid-independent role of PPARα in controlling brain function. Otherwise, it was believed that the presence of peroxisomes in abundance could be important for the compensation of mitochondrial instability in the adult brain hippocampus[7].

Like many other nuclear hormone receptors, it is not known if all the biological activity of PPAR-α also depends on its binding with the ligand and subsequent translocation to the nucleus. Since interaction with ligand plays an instrumental role in modulating the biological effect of most nuclear hormone receptors[22], an investigation into the existence of endogenous ligands of PPARα in the hippocampus was prompted. Successful identification of endogenous modulators of PPARα would aid in understanding the endogenous regulation hippocampal function and memory by PPARα. However, little is known about the presence of endogenous ligands of PPARα in the hippocampus and their role in regulating the synaptic activity. Although endocannabinoid-like molecules including oleoylethanolamide[23,24] and palmitoylethanolamide[25], the fatty acid derivative 20-carboxy-arachidonic acid[26], and leukotriene B4[27] have been considered as endogenous PPARα ligands, these compounds are ubiquitously present in different tissues including liver[28], kidney[29] and brain[30]. Furthermore, these compounds display a wide range of biological activities starting form antioxidant, anti-inflammation to neuroprotection[25,29]. In attempt to find an endogenous ligand of PPAR-α, a recent study[8] identifies that 1-palmitoyl-2-oleoyl-sn-glycerol-3-phosphocholine (16:0/18:1-GPC) could serve as a potent ligand of PPAR-α in liver. However, until now, nothing is known about the presence of endogenous ligand(s) in the hippocampus that are capable of modulating the PPARα activity in hippocampal neurons.

In order to identify physiologically available ligands, affinity purification was performed followed by gas phase mass spectrometry (GCMS) analyses in the nuclear extracts of lenti*ppara-overexpressed neurons. Then, the existence of these molecules was confirmed by affinity purification of hippocampal extracts collected from wild-type and Pparα-null animals against GST-PPAR-α recombinant protein followed by GCMS analyses. These analyses identified three unique ligands 3-hydroxy-(2,2)-dimethyl butyrate (HMB), hexadecanamide (HEX), and 9-Octadecenamide (OCT) in brain hippocampus. Further structural analyses revealed that two key amino acid residues Tyrosine 314 and 464 in the ligand binding pocket of PPARα are important for the binding with these ligands, which was confirmed by making site-directed mutated constructs of PPARα, subsequent expression of these constructs in neuronal cells using lentiviral strategy, and GCMS analyses of the affinity-purified nuclear fraction. The role of these ligands in controlling the expression of synaptic proteins and regulating the synaptic function of hippocampal neurons has also been analyzed.

The HMB, HEX and OCT ligands induce the activation of PPARα in brain cells and increase synaptic functions via upregulation of different synaptic molecules and calcium entry. What is needed in the art are PPARα ligands for modulating PPARα activity and for treatment of disorders such as dementia, neurological disorders, lysosomal storage disorders and body weight disorders.

BRIEF SUMMARY

Methods of modulating peroxisome proliferator-activated receptor α (PPARα) activity in a cell in a subject in need thereof are provided. The methods include administering an effective amount of a PPARα ligand to the subject, the PPARα ligand being selected from the group consisting of 3-hydroxy-2,2-dimethyl butyrate (HMB), hexadecanamide (HEX) and 9-octadecenamide (OCT).

Methods of treating dementia, neurodegenerative disorders, lysosomal storage diseases and body weight disorders in a subject in need thereof are provided. The methods include administering an effective amount of a PPARα ligand to the subject. The PPARα ligand is selected from the group consisting of 3-hydroxy-2,2-dimethyl butyrate (HMB), hexadecanamide (HEX) and 9-octadecenamide (OCT).

BRIEF DESCRIPTION OF THE DRAWINGS

FIGS. 1A-1L. Identification of Endogenous Ligands of PPAR-α in the mouse brain hippocampus.

(FIG. 1A) A flow chart represents the procedure for the affinity purification of nuclear ligands of PPAR-α. (FIG. 1B) GCMS analyses of the acetonitrile- and (FIG. 1C) chloroform-reconstructed nuclear extracts of WT and KO hippocampus (n=3 per group) after pulling down with GST-PPARα. (Similar GCMS analyses were performed in (FIG. 1D) acetonitrile- and (FIG. 1E) chloroform-reconstituted nuclear extracts of Pparabeta-null hippocampal tissue (n=3 per group). Chemical structure of 3-hydroxy, 2,2-dimethyl butyrate (HMB) (FIG. 1F), hexadecanamide (HEX) (FIG. 1G), and 9-Octadecenamide or oleamide (OCT) (FIG. 1H). (FIG. 1I) The immunoblot analyses of eluate collected from glutathione column probed with anti-GST, anti-GST-PPAR-α, and anti GST-PPARβ antibodies (upper panel), and with anti-PPAR-α or anti-PPARβ antibody (lower panel). Histone 3 (H3) immunoblot was performed in the nuclear lysate (input) to show the purity of the nuclear extract (middle panel). (FIG. 1J) Flow-chart of the GCMS analysis for identifying endogenous ligands after de novo synthesized PPARα. GCMS analyses of the chloroform-extracted nuclear fraction of (FIG. 1K) lenti-vector and (FIG. 1L) lenti-PPARα-LBD-transduced hippocampal neurons. Results are confirmed after three independent experiments.

FIGS. 2A-2G. Analyses of the interaction of OCT, HEX, and HMB with PPARα by high-throughput analyses.

(FIG. 2A) A schematic presentation of TR-FRET analysis to analyze the interaction between endogenous ligands and PPARα-PGC-1A complex. TR-FRET analyses of (FIG. 2B) OCT, (FIG. 2C) HEX, and (FIG. 2D) HMB as plotted fluorescence vs. logarithmic scale of ligand concentration. Thermal-shift assay of (FIG. 2E) OCT, (FIG. 2F) HEX, and (FIG. 2G) HMB as described under materials and method section. Results are confirmed after three independent experiments.

FIGS. 3A-3L. A proteomic approach to study the interaction between ligands and PPARα in a molecular level.

(FIG. 3A) Ribbon representations of superposed structures of PPAR-α ligand binding pocket along with its ligands OCT (FIG. 3A), HEX (FIG. 3B), and HMB (FIG. 3C). groups of amino acids positioned at a distance of 4 A° around the ligands were also shown in green colour. (FIG. 3D) A plasmid map of PPARα gene cloned in pLenti6 vector and the restriction site to clone the entire PPARagene as shown in the middle panel. The detailed map of FL Ppara, Y314D Ppara, Y464DPpara, and Y314D/Y464D Ppara gene cloned in the vector using lentiviral packaging kit as supplied by Life technologies. Thermal shift assay of (FIG. 3E) FL PPARα and (FIG. 3F) Y314D/Y464D PPARα protein. Tm represents the melting temperature. (FIG. 3G) A flow-chart represents the strategy of GCMS analyses for the detection of endogenous ligands in Ppara-null neuronal extracts infected with lentivirus particles of different PPARα constructs. (FIGS. 3H-L) GCMS analyses in the GFP-affinity purified extracts of Ppara-null hippocampal neurons transduced with (FIG. 3H) GFP only, (FIG. 3I) GFP-FLP-para, (FIG. 3J) GFP-Y314DPpara, (FIG. 3K) GFP-Y464DPpara, and (FIG. 3L) GFP-Y314D/Y464DPpara viruses.

PPRE-luciferase activity in the mouse primary astrocytes after 4 hrs of incubation with (FIG. 4A) OCT, (FIG. 4B) HEX, and (FIG. 4C) HMB at their wide range of concentrations. Results are mean±SD of three independent experiments *p<0.01 vs. control.

FIGS. 5A-5L. The role of endogenous ligands of PPARα on the morphological plasticity of hippocampal neurons.

Double immunostaining of MAP-2 and phalloidin to measure the spine density in hippocampal neurons transduced with vector, FLPpara, and Y464DPpara viruses after the treatment with (FIG. 5A) solvent (only DMSO), (FIG. 5B) OCT, (FIG. 5C) HEX, and (FIG. 5D) HMB. AMPA-driven calcium influx was measured in OCT (red), HEX (green) and HMB (purple)-treated Ppara-null hippocampal neurons transduced with (FIG. 5E) FLPpara, (FIG. 5F) Y314D, (FIG. 5G) Y464D, and (FIG. 5H) Y314D/Y464D PPARα genes. All neurons were treated with 50 μM of NMDA receptor antagonist N20C to inhibit passive calcium flow through NMDA receptor. (FIGS. 5I-L) Similarly NMDA-driven calcium influx was measured in the lentivius-infected hippocampal neurons in the presence of different endogenous ligands. In these cases, Naspm HCl was treated to stop the passive flow of calcium currents through AMPA receptor.

(FIG. 6A) The intracellular distribution of PPARα, β and γ were shown by immunofluorescence (NeuN=green, PPARs=red) analyses in the CA1 regions of hippocampus. (FIG. 6B) Nuclear (NE) and cytoplasmic extracts (CE) of hippocampal tissue were immunoblotted for PPAR-α, β, and γ. Immunoblot analyses were performed in 6-8 weeks old WT and Ppara-null mice (n=3 per group). The purity of the cytoplasmic fraction was validated by GAPDH immunoblot analysis whereas histone 3 (H3) immunoblot was performed to evaluate the purity of nuclear fraction.

FIGS. 7A-7I. Identification of endogenous ligands of PPARα in the mouse brain hippocampus.

GC-MS analyses of chloroform—(FIGS. 7A & 7B) and acetonitrile—(FIG. 7C) reconstituted nuclear extracts of WT hippocampus after pulling down with GST-PPARα-LBD. Similar GC-MS analyses were performed in chloroform (FIG. 7D) and acetonitrile (FIG. 7E) reconstituted nuclear extracts after pulling down with GST-PPARβ-LBD. FIG. 7F) The immunoblot analyses of eluate collected from glutathione column probed with anti-GST antibody (upper panel), and anti-PPARα or anti-PPARβ antibodies (lower panel). Histone 3 (H3) immunoblot was performed in the nuclear lysate (input) to show the purity of the nuclear extract (middle panel). GC-MS analyses of the chloroform-extracted nuclear fraction of lenti-vector—(FIG. 7G) and lenti-PPARα—(FIG. 7H) transduced Ppara-null hippocampal neurons. FIG. 7I) Neuronal extracts infected with lenti-vector and lenti-PPARα were analyzed for PPARα and then normalized with actin. Results were confirmed by three independent experiments.

FIGS. 8A-8I. Analyses of the interaction of OCT, HEX and HMB with PPARα by TR-FRET.

Figure 8F:
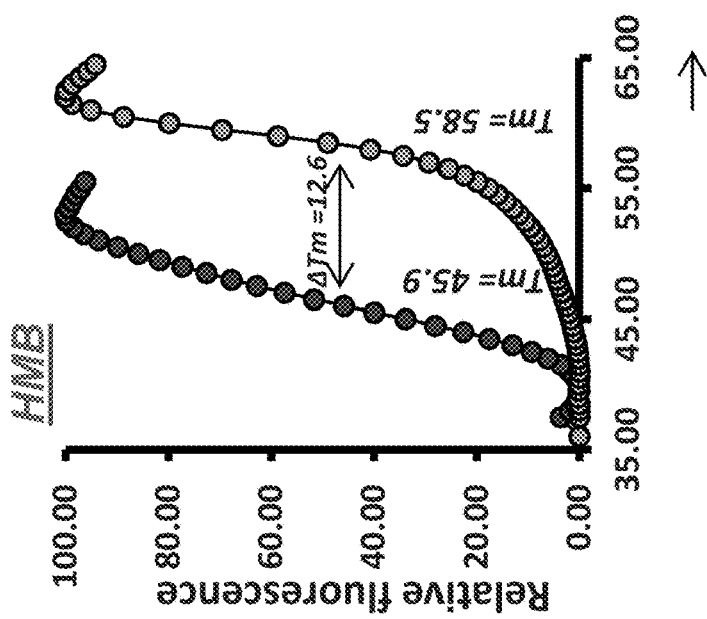
Figure 8E:
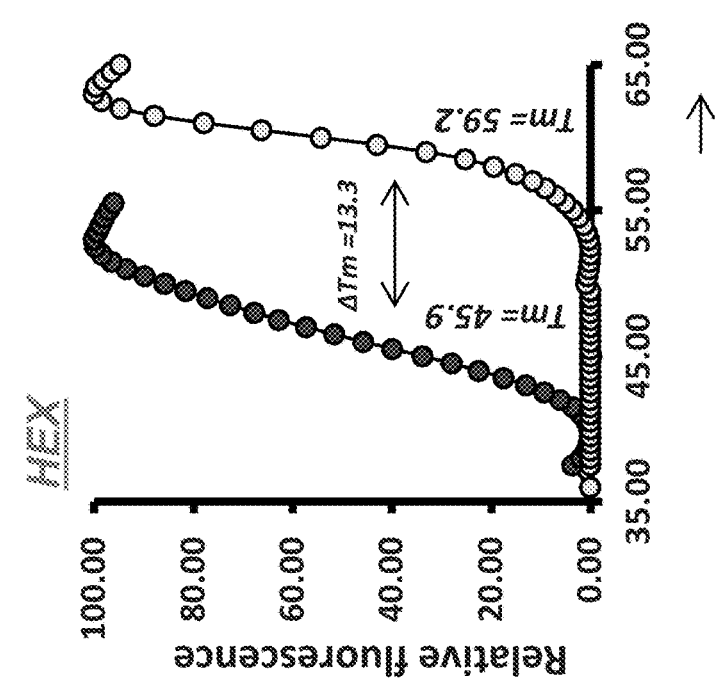
Figure 8D:
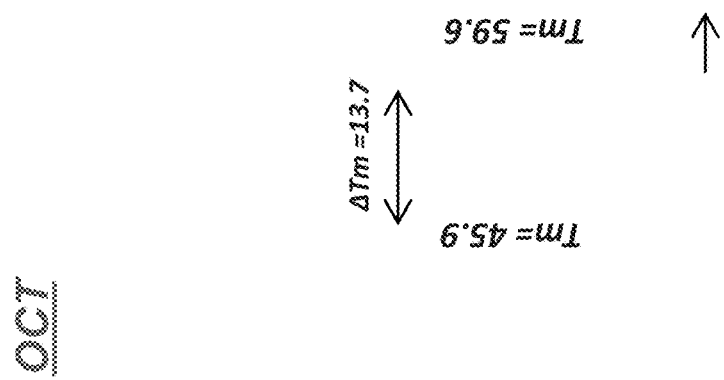

TR-FRET analyses of OCT (FIG. 8A), HEX (FIG. 8B) and HMB (FIG. 8C) plotted as fluorescence vs. logarithmic scale of ligand concentration. Thermal-shift assay of OCT (FIG. 8D), HEX (FIG. 8E) and HMB (FIG. 8F) was performed as described under the Materials and Method section.

Equation for full-length protein only:

$$y=50=-0.0652x^3+9.053x^2-408.09x+6012.7;\ x=45.96321$$

Equation for full length protein with OCT:

$$y=50=-0.0002x^5+0.052x^4-5.1349x^3+250.52x^2-6041.9x+57653;\ x=59.6128$$

Equation for full length protein with HEX:

$$y=0.0074x^3-0.8528x^2+31.967x-389.74; x=59.2835$$

Equation for full length protein with HMB:

$$y=-0.06529x^3+9.053x^2-408.09x+6012.7;\\ x=58.494798$$

Figure 8G:
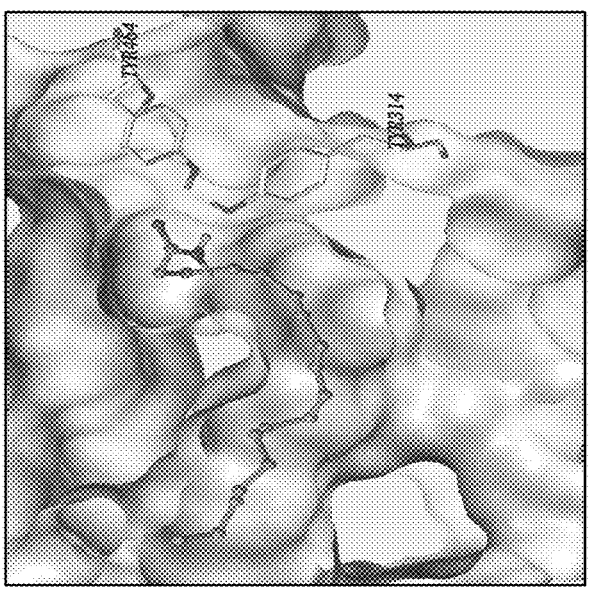
Figure 8H:
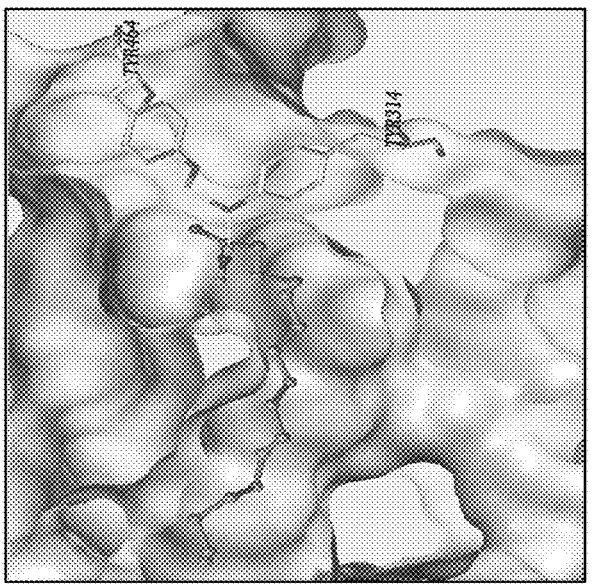
Figure 8I:
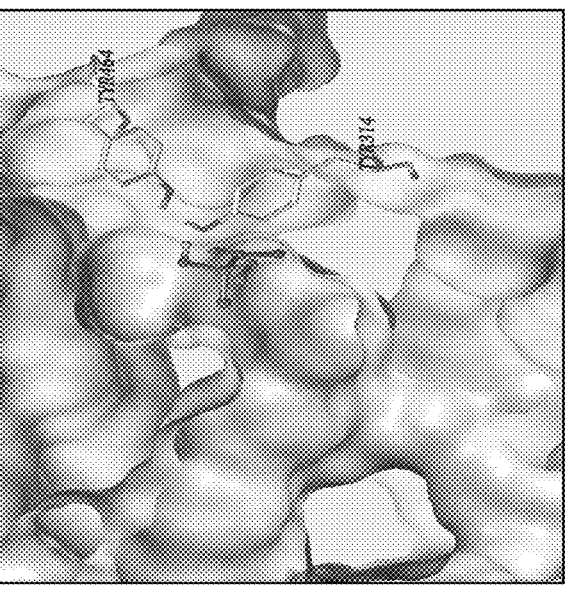

Ribbon representations of superposed structures of PPARα ligand binding pocket along with its ligands OCT (FIG. 8G), HEX (FIG. 8H) and HMB (FIG. 8I) are shown. Results are confirmed by three independent experiments.

FIGS. 9A-9L. Interaction between ligands and PPARα at the molecular level.

Figure 9G:
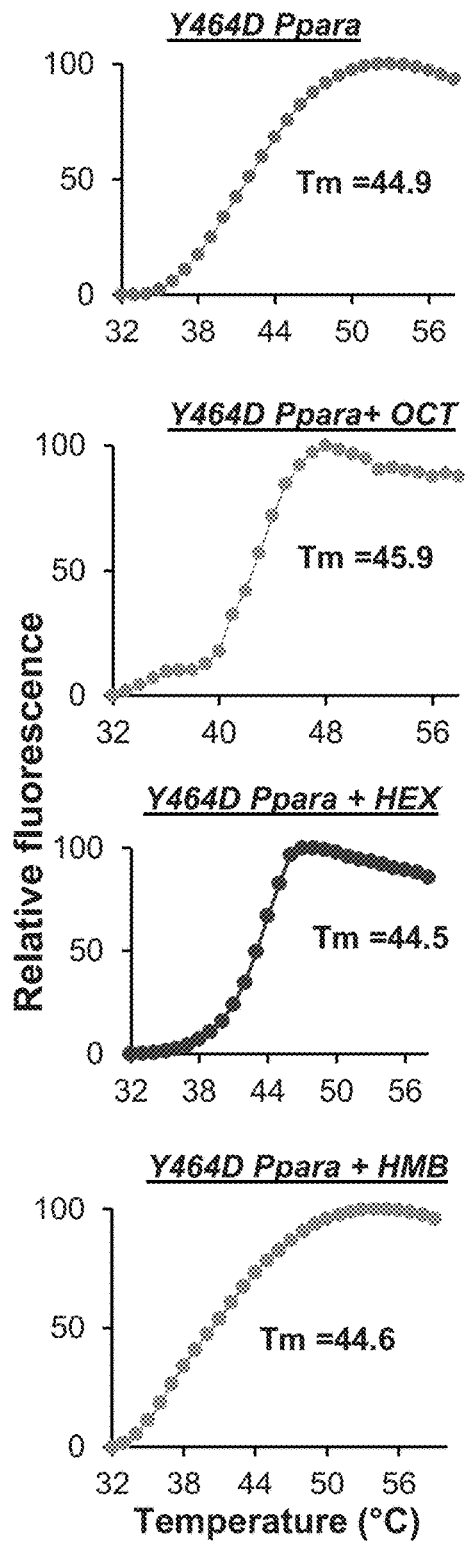
Figure 9H:
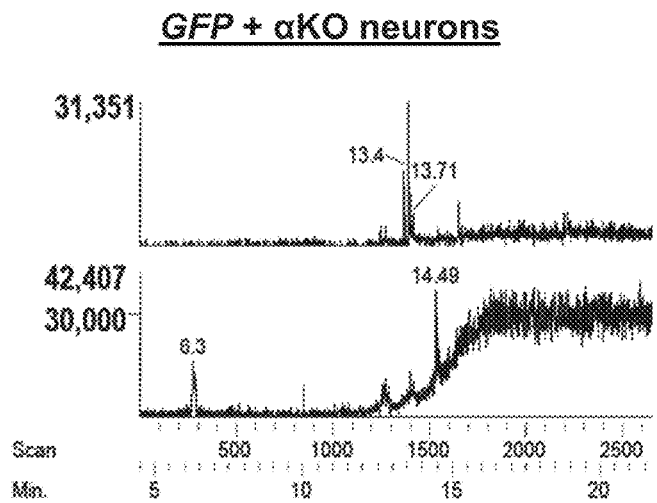
Figure 9I:
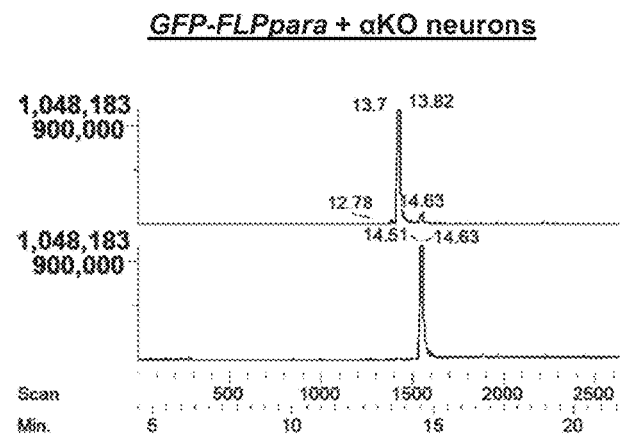
Figure 9J:
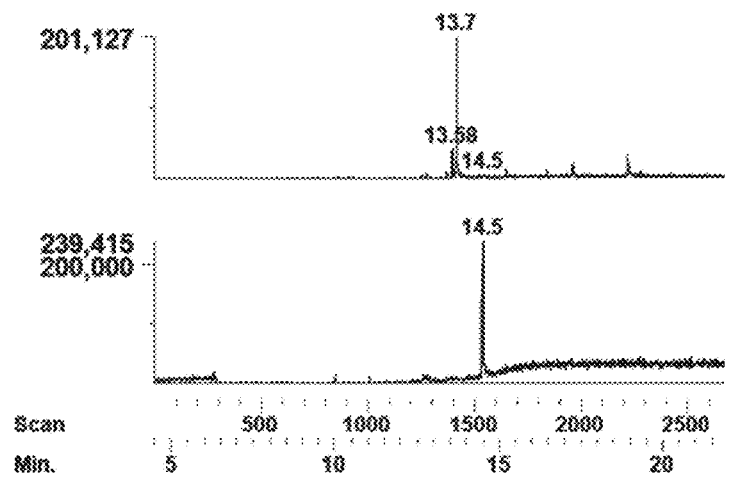
Figure 9K:
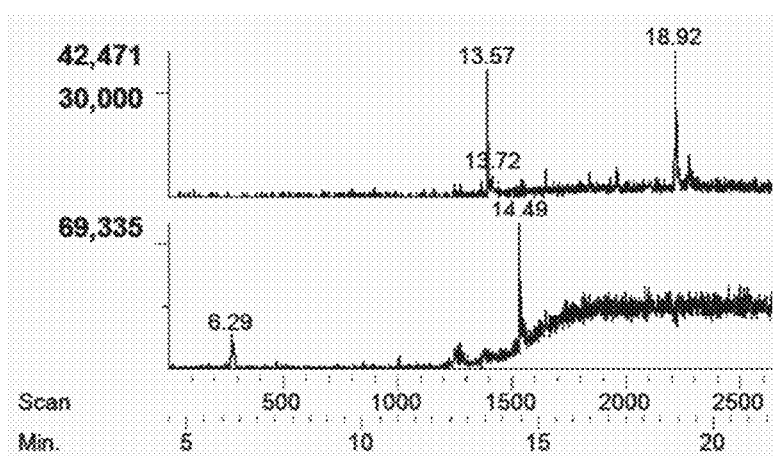
Figure 9L:
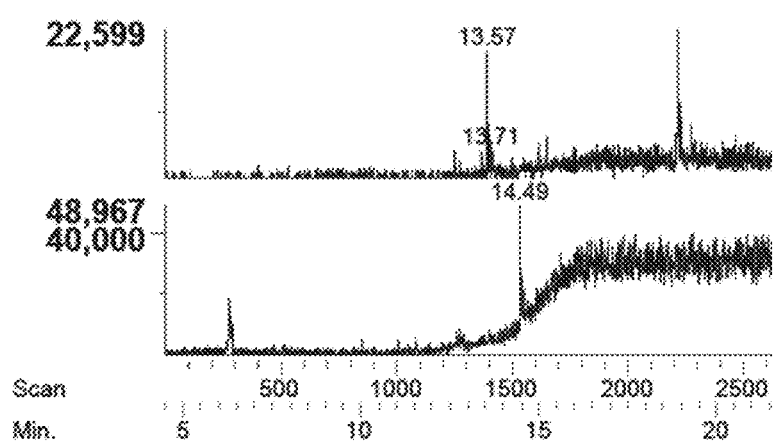

Atom-specific representations of superimposed structures of Y464D-PPARα ligand binding pocket along with OCT (FIG. 9A), HEX (FIG. 9B) and HMB (FIG. 9C). Amino acids positioned at a distance of 4 A° around the ligands were also shown in yellow color. FIG. 9D) Detailed maps of FL-Ppara, Y314D-Ppara, Y464D-Ppara, and Y314D/Y464D-Ppara are shown. Thermal shift assays of (FIG. 9E) FL-PPARα and (FIG. 9F) Y314D/Y464D-PPARα proteins. Tm represents the melting temperature. (FIG. 9G) Thermal shift assay for Y464D-PPARα alone and together with three ligands. GC-MS analyses in GFP-affinity purified extracts of Ppara-null hippocampal neurons transduced with lentivirions containing GFP (FIG. 9H), GFP-FL-Ppara (FIG. 9I), GFP-Y314D-Ppara (FIG. 9J), GFP-Y464D-Ppara (FIG. 9K), and GFP-Y314D/Y464D-Ppara (FIG. 9L).

Figure 10L:
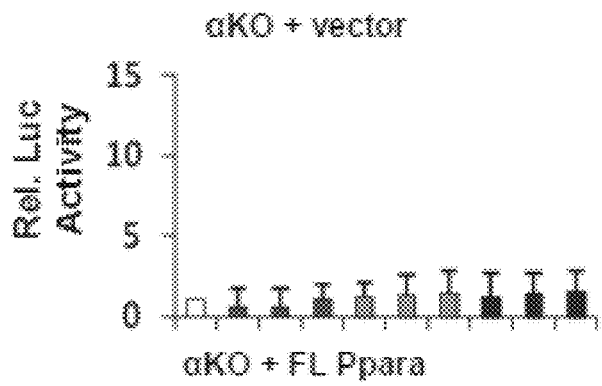
Figure 10M:
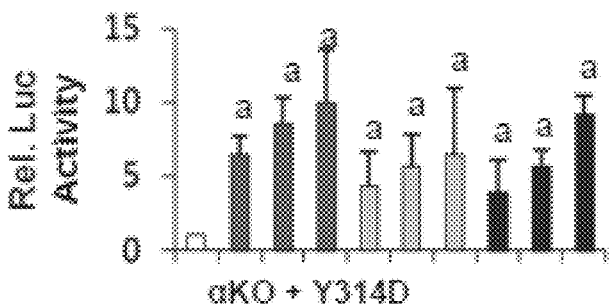
Figure 10N:
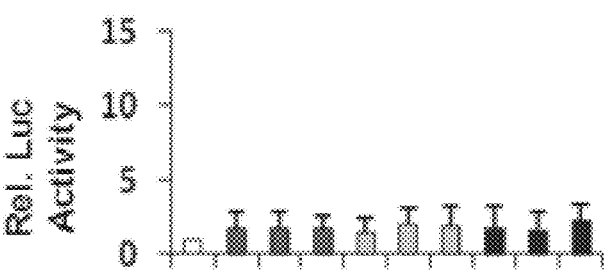
Figure 10O:
Figure 10P:
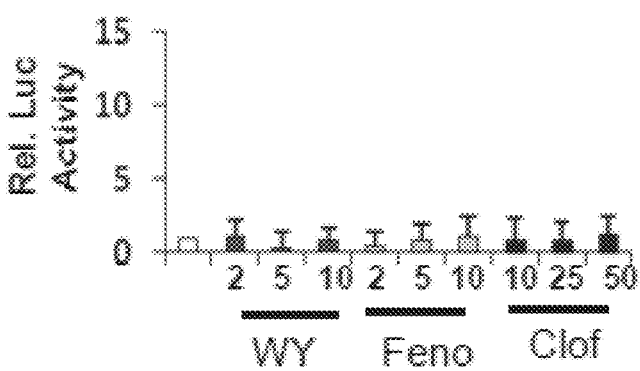
Figure 10Q:
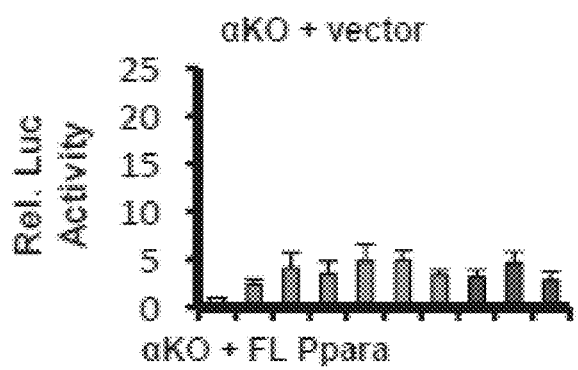
Figure 10R:
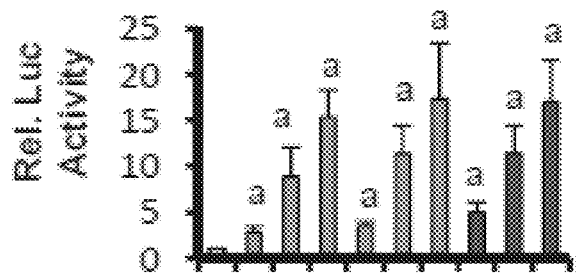
Figure 10S:
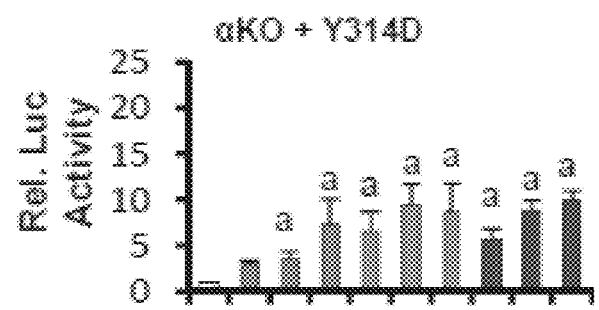
Figure 10T:
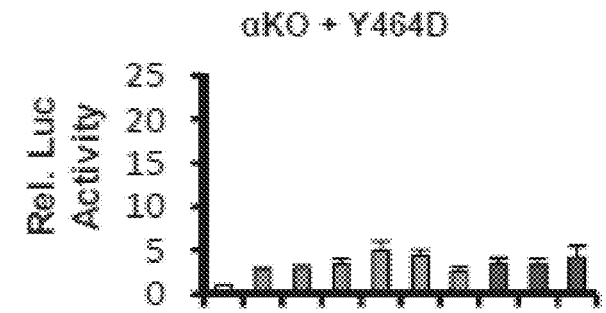
Figure 10U:
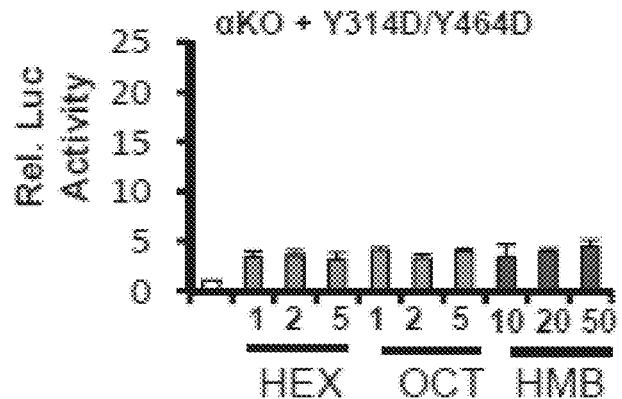

FIGS. 10A-10U Hippocampal ligands of PPARα induce PPRE-driven luciferase activity in primary mouse astrocytes and neurons.

Astrocytes plated at 60-70% confluence were transfected with tk-PPREx3-Luc, a PPRE-dependent luciferase reporter construct. After 24 h of transfection, cells were treated with different concentrations of HEX (FIG. 10A), OCT (FIG. 10B) and HMB (FIG. 10C) for 4 h followed by monitoring luciferase activity. Under similar experimental condition, MTT was performed to understand the effect of these ligands on cell viability (FIG. 10D, HEX; FIG. 10E, OCT; FIG. 10F, HMB). Results are mean±SD of three independent experiments. $^a$p<0.001 vs. control. Ppara-null astrocytes were transduced with lentivirions containing empty vector (FIG. 10G), FL-Ppara (FIG. 10H), Y314D-Ppara (FIG. 10I), Y464D-Ppara (FIG. 10J), and Y314D/Y464D-Ppara (FIG. 10K) for 48 h followed by transfection with tk-PPREx3-Luc. After 24 h of transfection, cells were treated with different doses of HEX, OCT and HMB for 4 h followed by monitoring luciferase activity. PPRE luciferase activity was assayed in Ppara-null astrocytes transduced with lentivirions containing empty vector (FIG. 10L), FL-Ppara (FIG. 10M), Y314D-Ppara (FIG. 10N), Y464D-Ppara (FIG. 10O), and Y314D/Y464D-Ppara (FIG. 10P) after treatment with different doses of WY14643, fenofibrate, and clofibrate. PPRE luciferase activity was assayed in primary hippocampal neurons transduced with lentivirions containing empty vector (FIG. 10Q), FL-Ppara (FIG. 10R), Y314D-Ppara (FIG. 10S), Y464D-Ppara (FIG. 10T), and Y314D/Y464D-Ppara (FIG. 10U) after treatment with different doses of HEX, OCT and HMB. Results are mean±SD of three independent experiments. $^a$p<0.001 vs. control.

FIGS. 11A-11P. The role of endogenous ligands of PPARα on the morphological plasticity of hippocampal neurons.

Figure 11F:
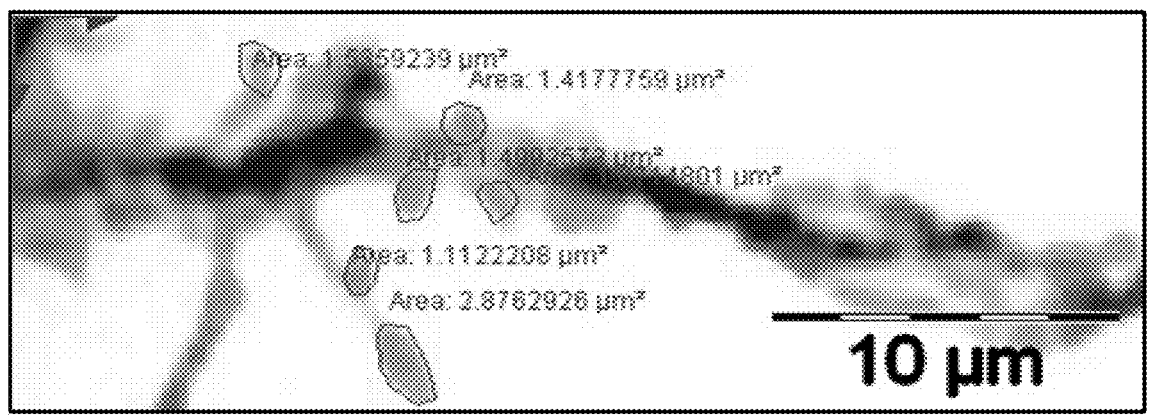

Ppara-null hippocampal neurons were transduced with lentivirions containing GFP (vector), FL-Ppara, and Y464D-Ppara for 48 h followed by treatment with vehicle (DMSO) (FIG. 11A), OCT (FIG. 11B), HEX (FIG. 11C), HMB (FIG. 11D), and WY14643 (FIG. 11E) for 24 h. Then neurons were stained for phalloidin to measure spine density. (FIG. 11F) A representative picture of dendrite with spines (Cyan color) used for counting area of spine heads. Area of spine heads (FIG. 11G) and number of spines (FIG. 11H) in 10 µm of dendrites. Results are mean±SEM of 5 neurons per group. $^a$p<0.05 vs vector only; $^b$p<0.05 vs FL-Ppara. AMPA-driven calcium influx was measured in OCT (red), HEX (green) and HMB (purple)-treated Ppara-null hippocampal neurons transduced with lentivirions containing FL-Ppara (FIG. 11I), Y314D-Ppara (FIG. 11J), Y464D-Ppara (FIG. 11K), and Y314D/Y464D-Ppara (FIG. 11L). All neurons were treated with 50 µM of NMDA receptor antagonist N20C to inhibit passive calcium flow through NMDA receptor. (FIG. 11M-P) Similarly NMDA-driven calcium influx was measured in the lentivius-infected Ppara-null hippocampal neurons in the presence of different endogenous ligands. In these cases, Naspm-HCl was treated to stop the passive flow of calcium currents through AMPA receptor. Results are mean of three independent experiments.

FIGS. 12A-12E. The subcellular localization of PPARα, β and γ isotypes in mouse brain hippocampus.

(FIG. 12A) The intracellular distribution of PPARα, β and γ were shown by immunofluorescence (NeuN, green; PPARs, red) analyses of the CA1 regions of hippocampus. (FIG. 12B) Nuclear-enriched (NE) and cytoplasmic enriched (CE) fractions of hippocampal tissues were immunoblotted for PPARα, β, and γ. Histone 3 (H3) and GAPDH were included for monitoring purity of nuclear extract and cytoplasmic extract, respectively. Immunoblot analyses were performed in 6-8 weeks old male WT and Ppara-null mice (n=3 per group). Bands were scanned and protein/H3 values are presented as relative to CE (FIG. 12C, PPARα; FIG. 12D, PPARβ; FIG. 12E, PPARγ). Results are mean±SEM of three mice per group. $^a$p<0.0001 vs CE.

Figure 13A:
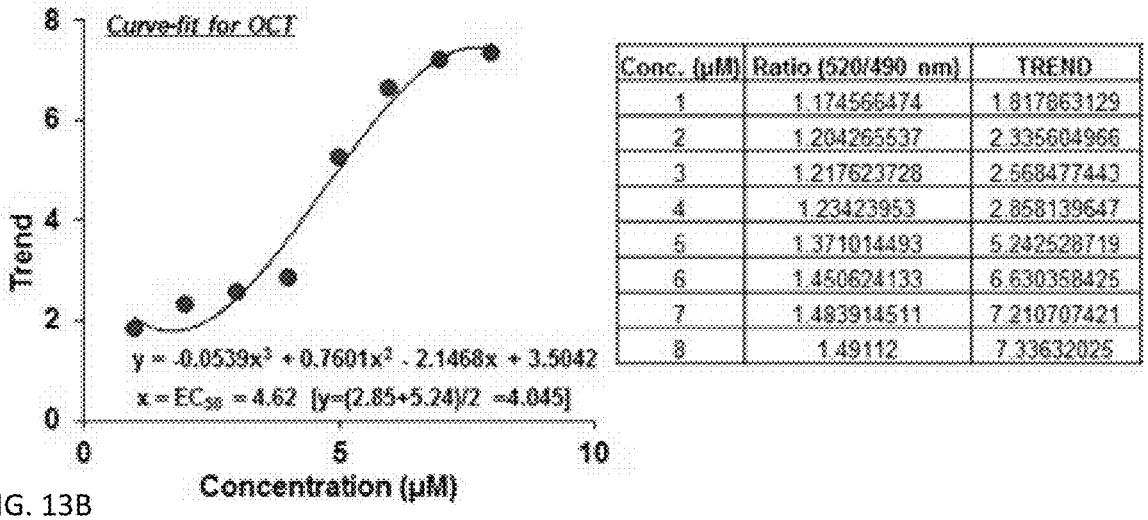
Figure 13B:
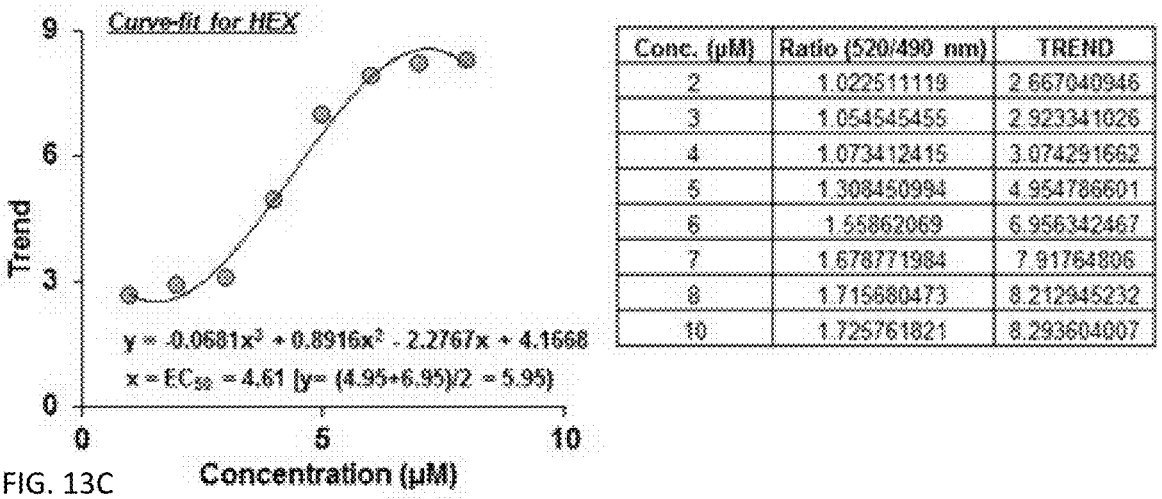
Figure 13C:
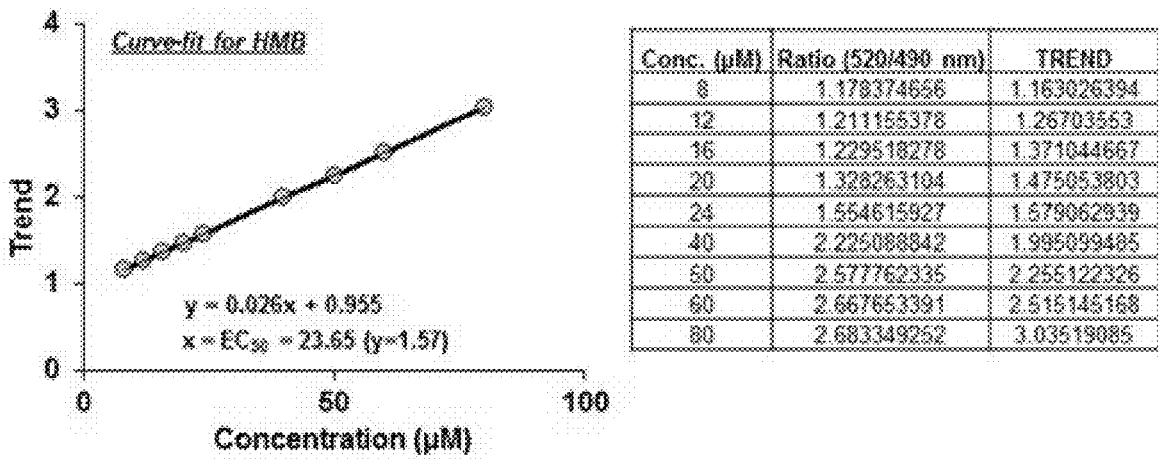

FIGS. 13A-13C. TR-FRET and extraction of EC50 values. Curve-fit for OCT (FIG. 13A), HEX (FIG. 13B) and HMB (FIG. 13C).

FIGS. 14A-14C. Transduction of Ppara-null astrocytes with lentivirions containing different Ppara constructs.

FIG. 14A) Ppara-null astrocytes cultured on coverslips were transduced with lentivirions containing FL-Ppara, Y314D-Ppara, Y464D-Ppara, and Y314D/Y464D-Ppara. Forty-eight h after transduction, level of GFP was monitored in an Olympus IX81 fluorescence microscope. DAPI was used to visualize nucleus. FIG. 14B) Similarly, 48 h after transduction, the level of PPARα [PPARα (53 kDa)+GFP (27 kDa)] was monitored by Western blot. FIG. 14C) Bands were scanned and values (PPARα/Actin) presented as relative to control. Results are mean±SD of three independent experiments. $^a$p<0.0001 vs control.

FIGS. 15A-15F. Peak integration statistics of GC-MS.

2,4-Bis(α,α-dimethylbenyl)phenol was used as internal standard (arrowhead) in GC-MS analyses (FIG. 15A, vector only; FIG. 15 B, FL Ppara; FIG. 15 C, Y314D Ppara; FIG. 15 D, Y464D Ppara; FIG. 15 E, Y314D/Y464D Ppara). FIG. 15 F) Chemical structure, molecular weight and CAS number of 2,4-Bis (α,α-dimethylbenyl)phenol.

FIGS. 16A-16H. OCT, HEX and HMB induce PPRE-driven luciferase activity in Pparb-null astrocytes in the presence of PPARγ antagonist.

Figure 16A:
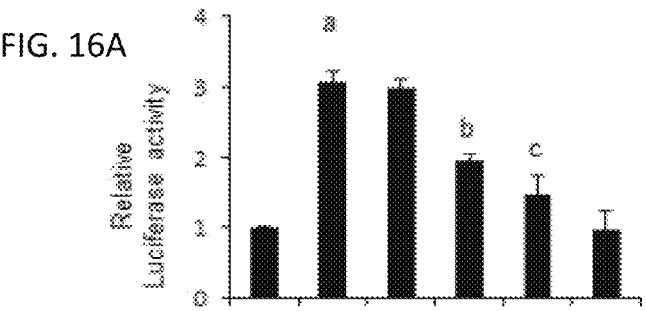
Figure 16B:
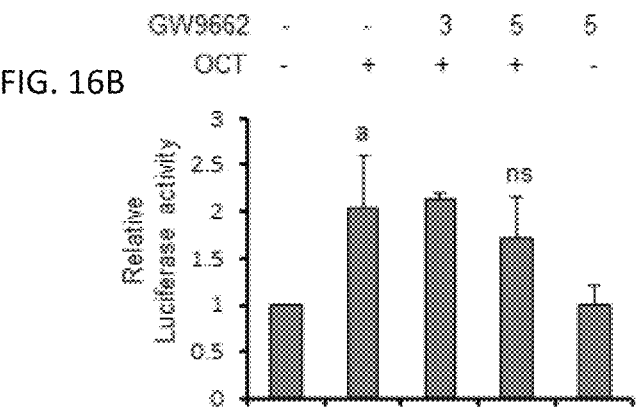
Figure 16C:
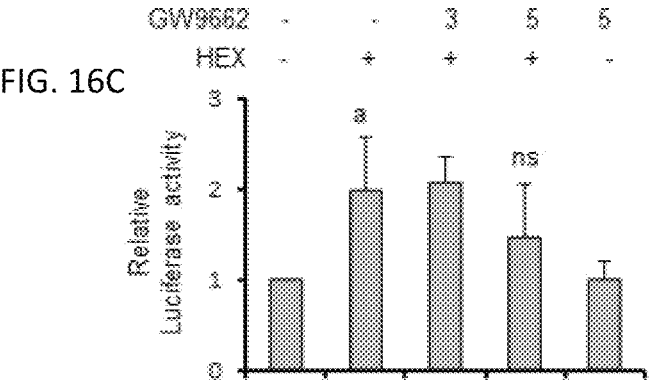
Figure 16D:
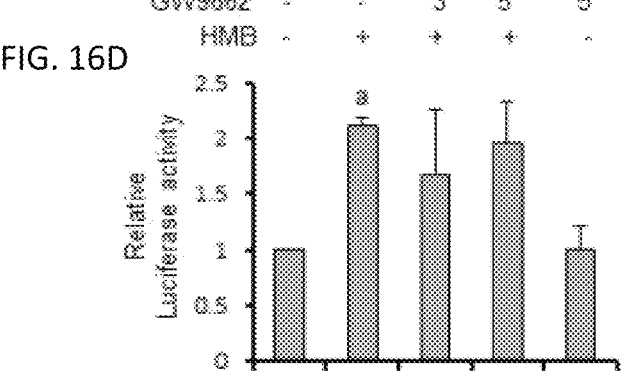
Figure 16E:
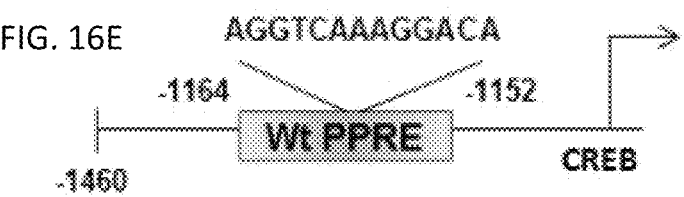

FIG. 16A) Pparb-null primary astrocytes plated at 60-70% confluence in 12-well plates were transfected with 0.25 µg of tkPPREx3-Luc (a PPRE-dependent luciferase reporter construct). Twenty-four hours after transfection, cells were treated with different concentrations of GW9662 for 30 min followed by stimulation with rosiglitazone. After 4 h, luciferase activities were assayed. Data are mean±SD of three different experiments. $^a$p<0.001 versus control; $^b$p<0.05 & $^c$p<0.01 versus rosiglitazone. After transfection, cells were also treated with GW9662 followed by stimulation with OCT (FIG. 16B), HEX (FIG. 16C) and HMB (FIG. 16D). After 4 h, luciferase activities were assayed. $^a$p<0.001 versus control; ns, not significant. (FIG. 16E, SEQ ID NO: 9) Promoter map of CREB shows the presence of a consensus PPRE. ChIP analyses (FIG. 16F) followed by real-time (FIG. 16G-H) validation of CREB promoter after pulling down with PPARα and PGC1α. Data are mean±SD of three different experiments. $^a$p<0.001 versus control.

FIGS. 17A-17L. Effect of HEX, OCT and HMB on the expression of synaptic molecules in Ppara-null hippocampal neurons and neurons transduced with different Ppara constructs.

Figure 17E:
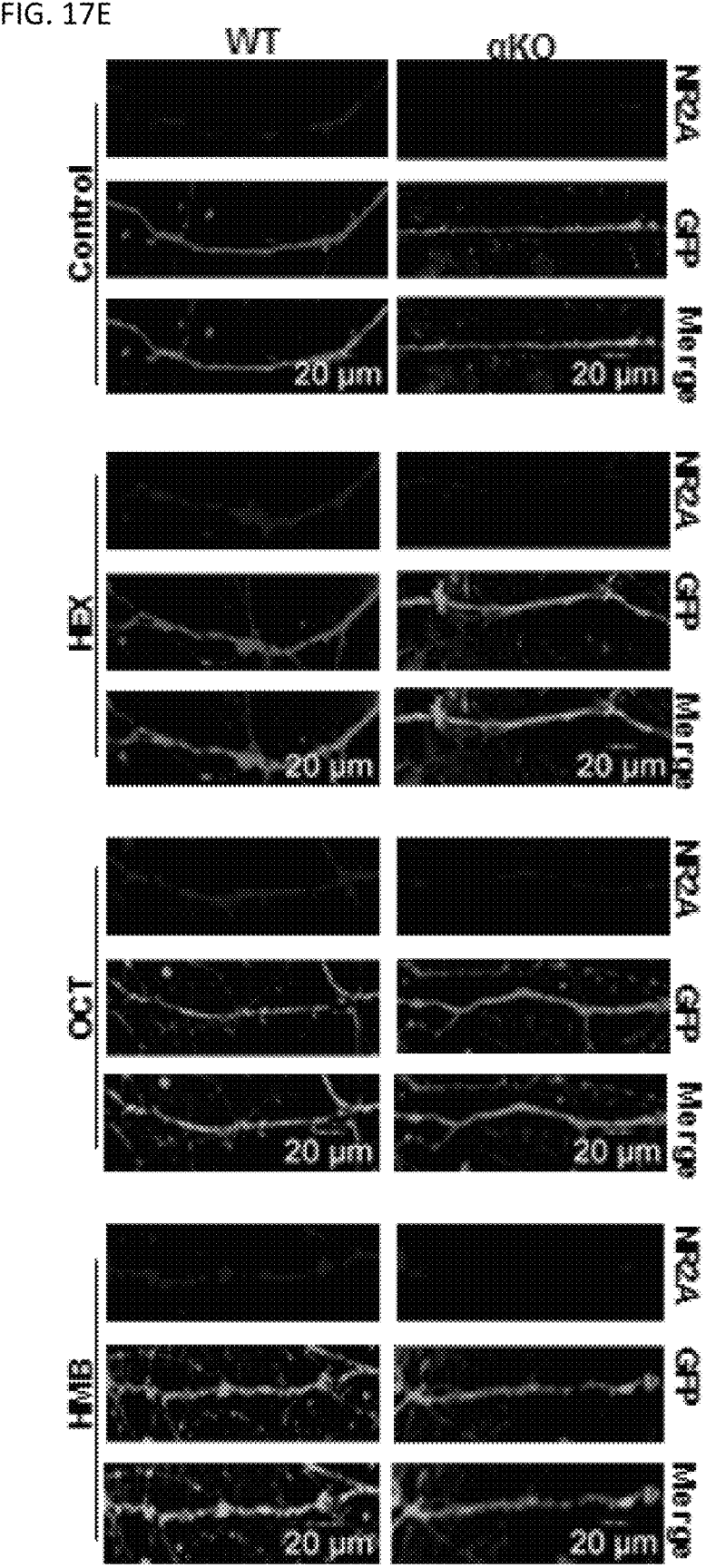
Figure 17F:
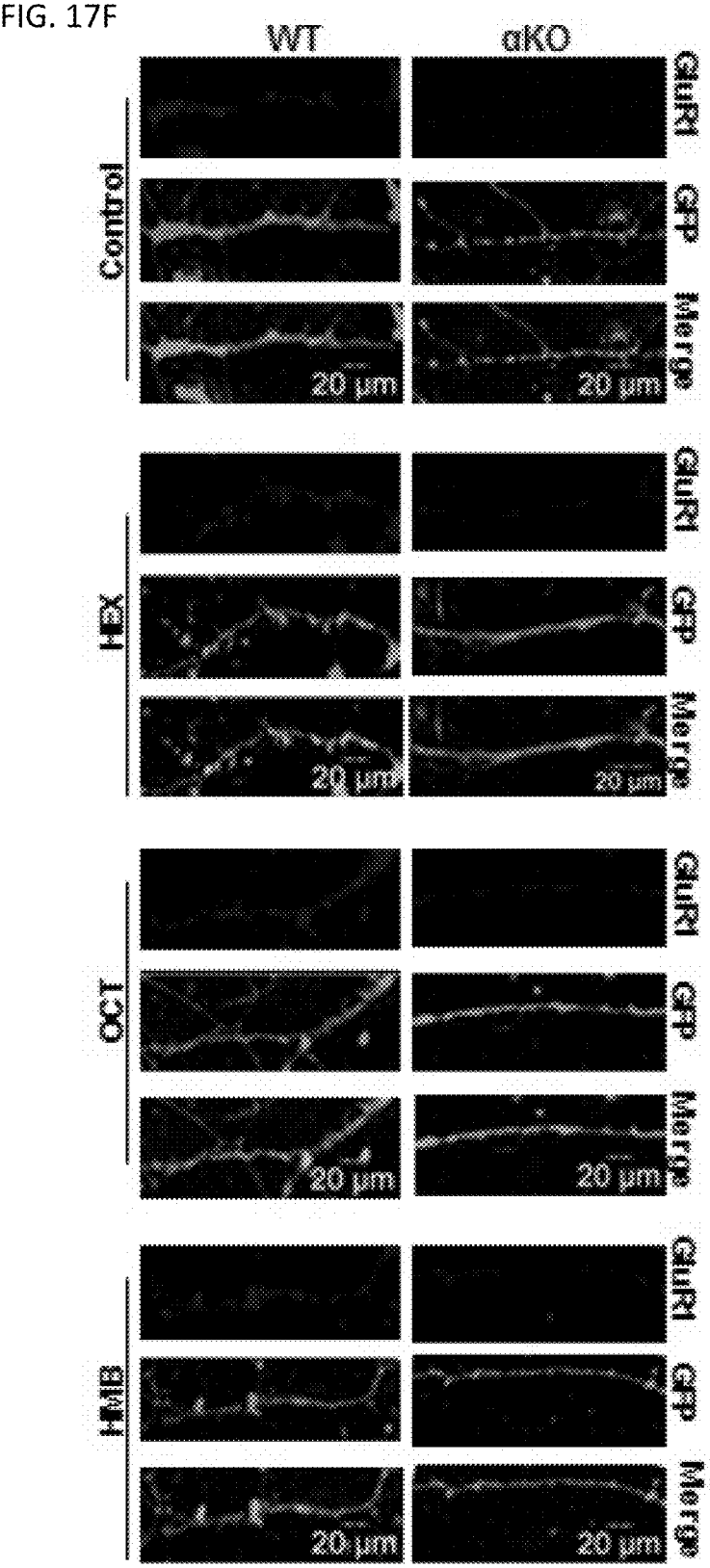

(FIG. 17A) Immunoblot analyses followed by densitometric analyses of NR2A (FIG. 17B), GluR1 (FIG. 17C) and CREB (FIG. 17D) were performed in Ppara-null and WT hippocampal neurons treated with 5 μM HEX, 5 μM OCT and 50 μM HMB. Data are mean±SD of three different experiments. $^a$p<0.05 versus WT-control. Immunocytochemical analyses of NR2A (FIG. 17E) and GluR1 (FIG. 17F) in WT and Ppara-null hippocampal neurons treated with HEX, OCT and HMB. Hippocampal neurons were transduced with lenti-GFP for 48 h followed by treatment with different ligands. Immunoblot analyses followed by relative densitometric analyses of CREB in Ppara-null hippocampal neurons transduced with lentivirions containing different Ppara constructs followed by treatment with HEX (FIG. 17G-H), OCT (FIGS. 17I-J) and HMB (FIG. 17K-L). Bands were scanned and presented as relative to control (FIG. 17H, HEX; FIG. 17J, OCT; FIG. 17L, HMB). Data are mean±SD of three different experiments. $^a$p<0.05 vs FLP-para control.

Figure 18:
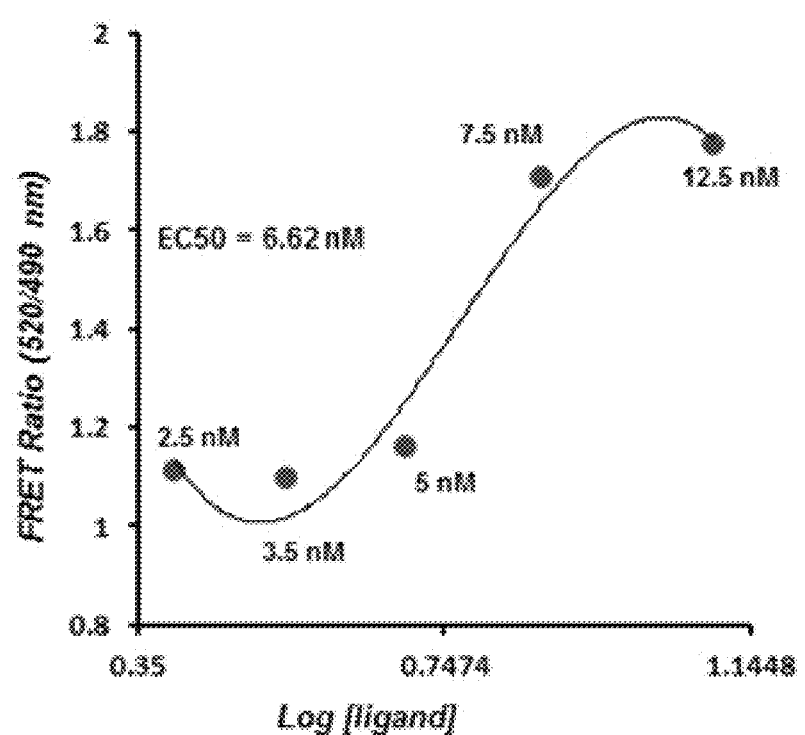

FIG. 18. Analysis of the interaction of GW7647 with PPARα by TR-FRET. TR-FRET analysis of GW7647 was plotted as fluorescence vs. logarithmic scale of ligand concentration.

DETAILED DESCRIPTION

The embodiments disclosed below are not intended to be exhaustive or to limit the scope of the disclosure to the precise form in the following description. Rather, the embodiments are chosen and described as examples so that others skilled in the art may utilize its teachings.

Methods of modulating peroxisome proliferator-activated receptor α (PPARα) activity in a cell in a subject are provided. An effective amount of a PPARα ligand may be administered to the subject. The PPARα ligand is selected from the group consisting of 3-hydroxy-2,2-dimethyl butyrate (HMB), hexadecanamide (HEX) and 9-octadecenamide (OCT).

The PPARα activity may be modulated in different cells including hippocampal neurons and other brain cells.

The PPARα ligands may be administered to treat dementia, neurodegenerative disorders, lysosomal storage disorders or obesity.

"Treating", "treat", or "treatment" within the context of the instant invention, means an alleviation of symptoms associated with a disorder or disease, or halt of further progression or worsening of those symptoms, or prevention or prophylaxis of the disease or disorder. For example, within the context of this invention, successful treatment may include an alleviation of symptoms related to dementia, neurodegenerative disorders, lysosomal storage disorders, and body weight disorders. The treatment may include administering an effective amount of a PPARα ligand to the subject that results in an alleviation of symptoms associated with a disorder or disease, or halt of further progression or worsening of those symptoms, or prevention or prophylaxis of the disease or disorder.

By way of non-limiting example, neurodegenerative disorders may be selected from neuronal ceroid lipofuscinosis, Alzheimer's disease, Huntington's disease, Amyotrophic lateral sclerosis (ALS), Parkinson's disease, including Parkinson's plus diseases such as multiple system atrophy (MSA), progressive supranuclear palsy (PSP), corticobasal degeneration (CBD) and dementia with Lewy bodies (DLB).

By way of non-limiting example, lysosomal storage disorders may be selected from Tay-Sach's disease, Fabry disease, Niemann-Pick disease, Gaucher disease, Hunter Syndrome, Alpha-mannosidosis, Aspartylglucosaminuria, Cholesteryl ester storage disease, Chronic Hexosaminidase A Deficiency, Cystinosis, Danon disease, Farber disease, Fucosidosis, and Galactosialidosis.

The term "subject" or "patient" as used herein, refers to a mammal, preferably a human.

In some embodiments, practice of the present invention will employ, unless otherwise indicated, conventional techniques of molecular biology, immunology, microbiology, cell biology and recombinant DNA, which are within the skill of the art. See e.g., Sambrook, Fritsch and Maniatis, MOLECULAR CLONING: A LABORATORY MANUAL, (Current Edition); CURRENT PROTOCOLS IN MOLECULAR BIOLOGY (F. M. Ausubel et al. eds., (Current Edition)); the series METHODS IN ENZYMOLOGY (Academic Press, Inc.): PCR 2: A PRACTICAL APPROACH (Current Edition) ANTIBODIES, A LABORATORY MANUAL and ANIMAL CELL CULTURE (R. I. Freshney, ed. (1987)). DNA Cloning: A Practical Approach, vol. I & II (D. Glover, ed.); Oligonucleotide Synthesis (N. Gait, ed., Current Edition); Nucleic Acid Hybridization (B. Hames & S. Higgins, eds., Current Edition); Transcription and Translation (B. Hames & S. Higgins, eds., Current Edition); Fundamental Virology, 2nd Edition, vol. I & II (B. N. Fields and D. M. Knipe, eds.)

Pharmaceutical Compositions

The ligands described herein may be used alone or in compositions together with a pharmaceutically acceptable carrier or excipient. Pharmaceutical compositions of the present invention comprise a therapeutically effective amount of a ligand of PPARα, including 3-hydroxy-2,2-dimethyl butyrate, hexadecanamide or 9-octadecenamide, together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. Other suitable pharmaceutically acceptable excipients are described in "Remington's Pharmaceutical Sciences," Mack Pub. Co., New Jersey, 1991, incorporated herein by reference.

The ligands described herein may be administered to humans and animals in dosage unit formulations containing conventional nontoxic pharmaceutically acceptable carriers, adjuvants, and vehicles as desired.

Methods of formulation are well known in the art and are disclosed, for example, in Remington: *The Science and Practice of Pharmacy*, Mack Publishing Company, Easton, Pa., 19th Edition (1995). Pharmaceutical compositions for use in the present invention can be in the form of sterile, non-pyrogenic liquid solutions or suspensions, coated capsules or lipid particles, lyophilized powders, or other forms known in the art.

Compositions of the invention may be formulated for delivery as a liquid aerosol or inhalable dry powder. Liquid aerosol formulations may be nebulized predominantly into particle sizes that can be delivered to the terminal and respiratory bronchioles.

Liquid dosage forms for oral administration include pharmaceutically acceptable emulsions, microemulsions, solutions, suspensions, syrups and elixirs. In addition to the active ligands, the liquid dosage forms may contain inert diluents commonly used in the art such as, for example, water or other solvents, solubilizing agents and emulsifiers such as ethyl alcohol, isopropyl alcohol, ethyl carbonate, EtOAc, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Solid dosage forms for oral administration include capsules, tablets, pills, powders, and granules. In such solid dosage forms, the active ligand is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, acetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

The active ligands can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active ligand may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a ligand of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulations, ear drops, and the like are also contemplated as being within the scope of this invention.

The ointments, pastes, creams and gels may contain, in addition to an active ligand of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Ligands of the invention may also be formulated for use as topical powders and sprays that can contain, in addition to the ligands of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a ligand to the body. Such dosage forms can be made by dissolving or dispensing the ligand in the proper medium. Absorption enhancers can also be used to increase the flux of the ligand across the skin. The rate can be controlled by either providing a rate controlling membrane or by dispersing the ligand in a polymer matrix or gel. The ligands of the present invention can also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes can be used. The present compositions in liposome form can contain, in addition to a ligand of the present invention, stabilizers, preservatives, excipients, and the like. The preferred lipids are the phospholipids and phosphatidyl cholines (lecithins), both natural and synthetic. Methods to form liposomes are known in the art. See, for example, Prescott (ed.), "Methods in Cell Biology," Volume XIV, Academic Press, New York, 1976, p. 33 et seq.

Aerosolized formulations of the invention may be delivered using an aerosol forming device, such as a jet, vibrating porous plate or ultrasonic nebulizer, preferably selected to allow the formation of an aerosol particles having with a mass medium average diameter predominantly between 1 to 5 μm. Further, the formulation preferably has balanced osmolarity ionic strength and chloride concentration, and the smallest aerosolizable volume able to deliver effective dose of the ligands of the invention to the site of the infection. Additionally, the aerosolized formulation preferably does not impair negatively the functionality of the airways and does not cause undesirable side effects.

Aerosolization devices suitable for administration of aerosol formulations of the invention include, for example, jet, vibrating porous plate, ultrasonic nebulizers and energized dry powder inhalers, that are able to nebulize the formulation of the invention into aerosol particle size predominantly in the size range from 1-5 μm. Predominantly in this application means that at least 70% but preferably more than 90% of all generated aerosol particles are within 1-5 μm range. A jet nebulizer works by air pressure to break a liquid solution into aerosol droplets. Vibrating porous plate nebulizers work by using a sonic vacuum produced by a rapidly vibrating porous plate to extrude a solvent droplet through a porous plate. An ultrasonic nebulizer works by a piezoelectric crystal that shears a liquid into small aerosol droplets. A variety of suitable devices are available, including, for example, AERONEB and AERODOSE vibrating porous plate nebulizers (AeroGen, Inc., Sunnyvale, Calif.), SIDE-STREAM nebulizers (Medic-Aid Ltd., West Sussex, England), PARI LC and PARI LC STAR jet nebulizers (Pari Respiratory Equipment, Inc., Richmond, Va.), and AEROSONIC (DeVilbiss Medizinische Produkte (Deutschland) GmbH, Heiden, Germany) and ULTRAAIRE (Omron Healthcare, Inc., Vernon Hills, Ill.) ultrasonic nebulizers.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-propanediol or 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables. The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form may be accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations may also be prepared by entrapping the drug in liposomes or microemulsions, which are compatible with body tissues.

A ligand described herein can be administered alone or in combination with other ligands, for a possible combination therapy being staggered or given independently of one another. Long-term therapy is equally possible as is adjuvant therapy in the context of other treatment strategies, as described above. Other possible treatments are therapy to maintain the patient's status after the initial treatment, or even preventive therapy, for example in patients at risk.

Effective amounts of the ligands of the invention generally include any amount sufficient to detectably an inhibition or alleviation of symptoms. The amount of active ingredient that may be combined with the carrier materials to produce a single dosage form will vary depending upon the host treated and the particular mode of administration. It will be understood, however, that the specific dose level for any particular patient will depend upon a variety of factors including the activity of the specific ligand employed, the age, body weight, general health, sex, diet, time of administration, route of administration, rate of excretion, drug combination, and the severity of the particular disease undergoing therapy. The therapeutically effective amount for a given situation can be readily determined by routine experimentation and is within the skill and judgment of the ordinary clinician.

If the ligand is administered in combination with another compound, the term "amount that is effective to modulate PPARα activity" is understood to mean that amount of a ligand in combination with the additional compound to achieve the desired effect. In other words, a suitable combination therapy according to the current invention encompasses an amount of the ligand and an amount of the additional compound, either of which when given alone at that particular dose would not constitute an effective amount, but administered in combination would be an "amount that is effective to modulate PPARα activity".

It will be understood, however, that the total daily usage of the ligands and compositions of the present invention will be decided by the attending physician within the scope of sound medical judgment. The specific therapeutically effective dose level for any particular patient will depend upon a variety of factors including the disorder being treated and the severity of the disorder; the activity of the specific ligand employed; the specific composition employed; the age, body weight, general health, sex and diet of the patient; the time of administration, route of administration, and rate of excretion of the specific ligand employed; the duration of the treatment; drugs used in combination or coincidental with the specific ligand employed; and like factors well known in the medical arts.

The dose of a ligand to be administered to warm-blooded animals, for example humans of approximately 70 kg body weight, is preferably from approximately 3 mg to approximately 5 g, more preferably from approximately 10 mg to approximately 1.5 g, most preferably from about 100 mg to about 1000 mg per person per day, divided preferably into 1 to 3 single doses which may, for example, be of the same size. Usually, children receive half of the adult dose.

Results

Role of PPARα in the Expression of Plasticity-Related Genes in Hippocampus

PPARα is strongly expressed in hippocampal neurons[6,31]. Since hippocampal neurons are equipped with a wide-spectrum of synaptic proteins related to Long term potentiation (LTP)[10] and long term depression (LTD)[11], the role of PPARα in regulating the expression of different LTP- and LTD-associated synaptic molecules was examined. LTP causes a persistent increase in synaptic strength between pre- and post-synaptic neurons, whereas LTD causes a persistent reduction of synaptic strength. An mRNA-based microarray followed by heat map analyses clearly indicated that hippocampus of Ppara-null (KO) mice, but not wild type (WT) mice, downregulation of 28 genes, upregulation of 34 genes and no alteration in 22 genes. (Data not shown.) Most of the downregulated mRNAs are involved in LTP, including the ionotropic AMPA receptors Gria1 and Gria3 mRNAs; ionotropic NMDA receptors Grin1, Grin2a and Grin2bmRNAs; immediate early genes (IEGs) mRNAs including Arc, Homer1 and Fos; and different synaptic membrane encoded mRNAs Adam10, Dlg4, Synpo, and Adcy1. On the contrary, most of the up-regulated mRNAs are associated with LTD including different protein phosphatase mRNAs such as; Ngfr, Pick1, Nos1, and Nfkb1. The downregulation of some crucial LTP-associated mRNAs in KO hippocampus including Arc, Gria1, Grin2a, Grin2b, and Creb was separately confirmed by real-time PCR analyses. Immunohistochemical analyses of PSD-95 (encoded by the Dlg4 gene) in the presynaptic fibers of CA1 hippocampus and immunoblot assay of NR2A (encoded by Grin2a), GluR1 (encoded by Gria1), PSD-95, Arc, and CREB further indicated that hippocampus of KO brain expressed less LTP-associated molecules than the hippocampus of WT mice.

Figure 7I:
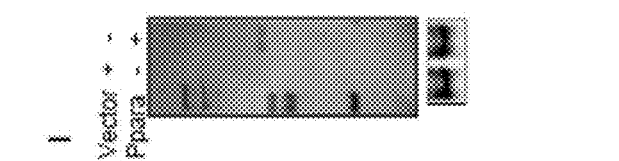
Figure 7H:
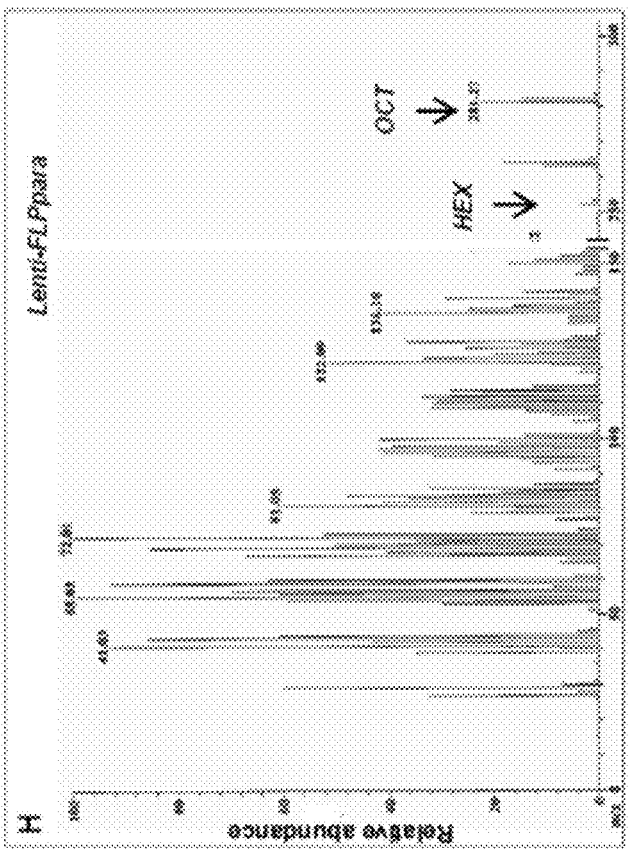
Figure 7G:
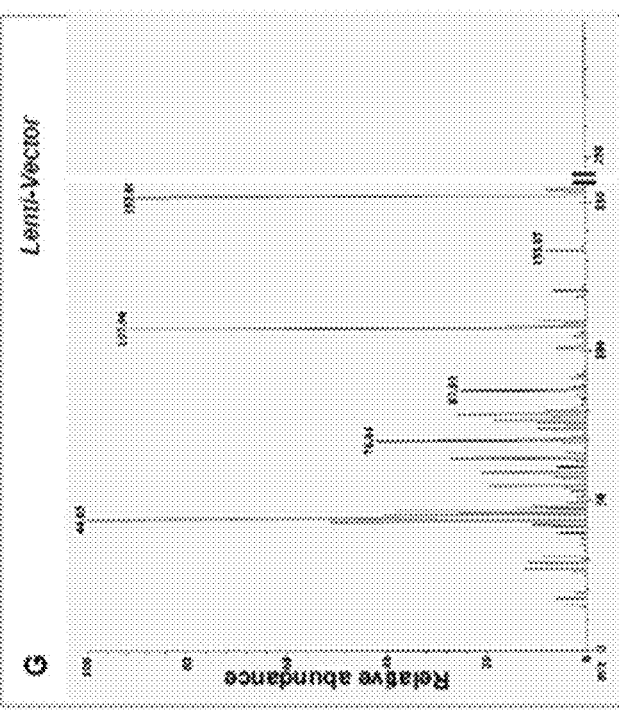

Identification of novel nuclear ligands of PPARα in the hippocampus PPARs are nuclear receptors that require the binding of ligands for activation of gene expression. Immunostaining of hippocampal section (FIG. 12A) and immunoblot analyses of nuclear-enriched fraction of hippocampal extracts (FIGS. 12B-E) clearly demonstrated that PPARα, but neither PPARβ nor PPARγ, was present in the nuclei, These results suggest that the hippocampus has endogenous expression of PPARα agonist and the such ligands should be present within the nucleus. In order to identify these ligands, a gas chromatography mass spectrometric (GCMS) technology was adopted. Briefly, nuclear extracts were prepared form mouse hippocampus, incubated with a GST-tagged PPARα ligand binding domain (LBD), purified with affinity chromatography, reconstituted with chloroform or acetonitrile, and GCMS analyses preformed. (FIG. 1A, FIGS. 7A-C.). Analysis chloroform extracts displayed two distinct peaks matching 9-octadecenamide (OCT) with an m/z at 23.03 minute (FIG. 7A) and hexadecanamide (HEX) with an m/z at 21.45 minute (FIG. 7B). On the other hand, GC-MS analyses of the acetonitrile fraction of affinity purified hippocampal nuclear extract resulted in a distinct peak of m/z 160.0 at 14.48 minutes that mated the NIST library for 3-hydroxy (2,2)-dimethyl butyric acid ethyl ester (HMB) (FIG. 7C). Interestingly, GCMS analyses of hippocampal nuclear extracts after pulling down with PPARβ-LBD did not exhibit any peak(FIG. 7D-E), suggesting that these three hippocampal ligands could be specific for PPARα. The fraction of hippocampal nuclear extracts eluted through the glutathione column was further immunoblotted to validate the accuracy of the affinity purification procedure, which clearly showed that all parameters including the amount of hippocampal tissue, amount of recombinant protein, and the volume of eluate were kept constant in all cases throughout the assay (FIG. 1I, FIG. 7F). However, the above-mentioned assay was unable to demonstrate if these ligands could display similar interaction with de novo-synthesized PPARα. Therefore, next cultured Ppara-null hippocampal neurons were infected with lentiviral particles of full-length PPARα and then immunoprecipitation performed followed by GCMS analyses (FIG. 1J, FIG. 7G-H). Similar to the previous observations, both OCT (FIG. 1K) and HEX (FIG. 1L) were found to be bound to de novo-synthesized PPARα in lenti-FLPara-transduced (FIG. 7H), but not with empty lenti-vector-transduced Ppara-null neurons (FIG. 7G). The efficiency of gene transduction was measured by immunoblot analyses of cell extract with PPARα antibody (FIG. 7I. In addition, these analyses successfully identified a group of biological ligands of PPARα, which are endogenously produced in the hippocampus. Some of these detected compounds are sulfur-containing unknown compounds such as thiazoles (MW 220-240), thiosemicarbazones (MW 190-200) and thiazolidine esters (MW 250-270) (Table 2). However, these compounds were excluded from this study because of their unknown biosynthetic pathway, relatively poor match-factor (<65), and commercial unavailability. Trans-O-dithiane-4,5 diol is the oxidized product of DTT used in the buffer whereas D-Galactono 1,4-lactone 5,6-octylidene is excluded because of the commercial unavailability of this compound required to confirm its association with PPARα. Taken together, our GC-MS analyses identified OCT, HEX and HMB as three putative, endogenously produced, but also commercially available, PPARα ligands.

Next, Time Resolved-Fluorescence Resonance Energy Transfer (TR-FRET) analysis was performed to confirm the interaction between these ligands and PPARα. The optimized TR-FRET analysis (FIG. 2A, FIG. 8A-C)) indicated that PGC-1α-PPARα LBD complex displayed a strong interaction with all these three ligands (FIG. 2B-D, FIG. 8A-C). FIG. 13 shows how these data were fit and EC50 values extracted for OCT (A), HEX (B) and HMB (C). In all cases, TR-FRET signals (FIG. 2D, FIGS. 8A-C)) released by PPARα LBD showed a steady increase. Although the signal intensity was observed higher in HMB compared to OCT (FIG. 2B, FIG. 8A) and HEX (FIG. 2C, FIG. 8B), both OCT and HEX generated FRET signals at much lower concentrations than that of HMB. On the other hand, a large thermal shift was observed as evidenced by a change in melting temperature of purified PPARα-LBD protein when incubated with these ligands (FIG. 2E-G, FIG. 8D-F) suggesting that these ligands truly interact with the ligand binding domain of PPARα with high efficiency.

Molecular Characterization of the Interaction Between the Ligand Binding Domain of PPARα and its Novel Ligands The next aim was to characterize the molecular interaction of these ligands with the PPARα-LBD. The in silico computer-aided cheminformatic analyses generated a reasonable docked pose of these ligands in the PPARα-LBD (FIG. 3A-C, FIG. 8G-I). The docked pose of all three ligands showed two potential hydrogen bonds between the ligand and two active-site residues, Tyr 314 (Y314) and Tyr 464 (Y464) (FIG. 3B), of the PPARα-LBD. The ligand-binding surface is amphipathic, as it shared both a negatively charged electrostatic surface and a few patches of a partial positively charged surface with mostly lipophilic, and some hydrophilic patches. Imposing the most stringent docking protocols, a reasonable docked poses of OCT (a total score of 10.15, a polar score of 1.05, and a crash score of −1.49; total binding energy −25.56 kcal/mol), HEX (a total score of 10.01, a polar score of 1.81, and a crash score of −1.04; total binding energy −26.3 kcal/mol), and HMB (a total score of 5.63, a polar score of 1.93, and a crash score of −1.55; total binding energy −10.5 kcal/mol) were obtained for PPARα. Interestingly, in the case of both PPARβ and PPARγ, by applying similar docking protocols, we failed to obtain any docked pose for these ligands, suggesting that the interaction of all three ligands with PPARα-LBD is specific and not possible in other PPAR isoforms. To further confirm this observation, in silico mutation analysis was performed, in which OCT, HEX, and HMB were placed in the ligand-binding pocket of Y464D-PPARα. After energy minimization (total binding energy is −15.6 kcal/mol for OCT, −14.3 kcal/mol for HEX and −5.04 kcal/mol for HMB), all three ligands were observed to be located far (>4A°) from aspartate (D) residue to establish any hydrogen bond (FIG. 9A-C), suggesting that the mutation of tyrosine 464 to aspartate significantly impairs the interaction of these ligands with PPARα. However, in silico modeling of protein-ligand interaction is hypothetical and requires rigorous experimental analysis for further validation.

Figure 3E:
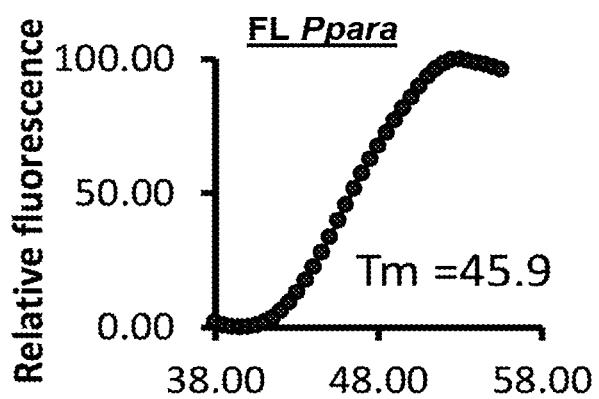
Figure 3F:
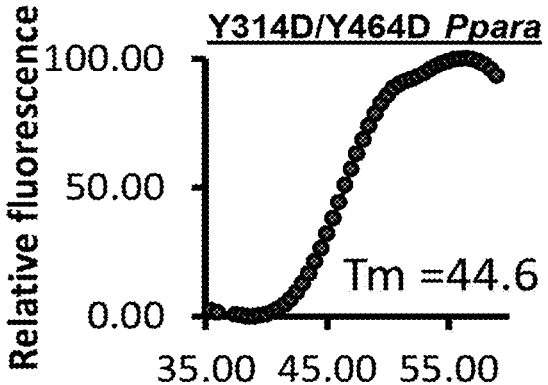
Figure 3G:
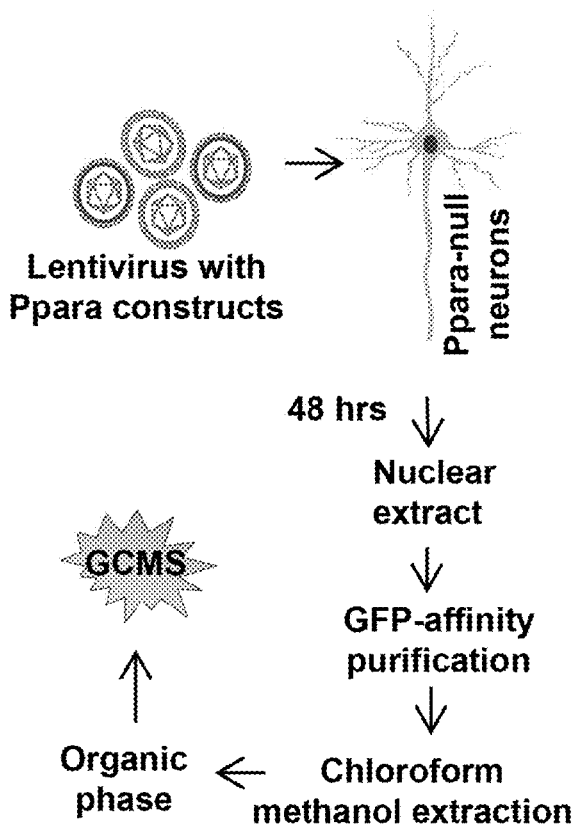
Figure 3H:
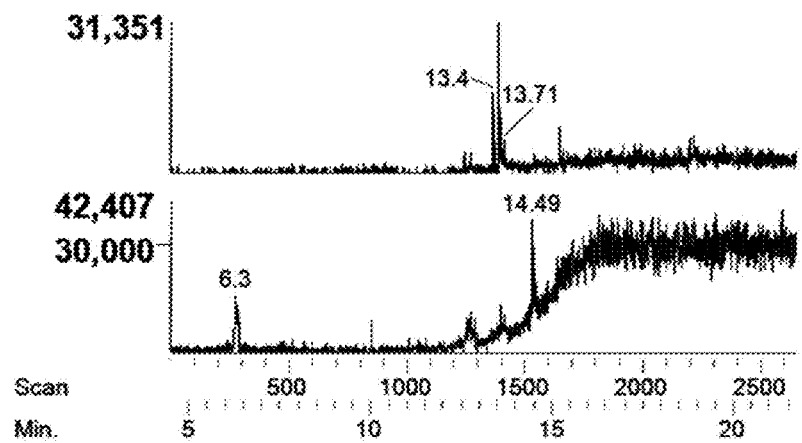
Figure 3I:
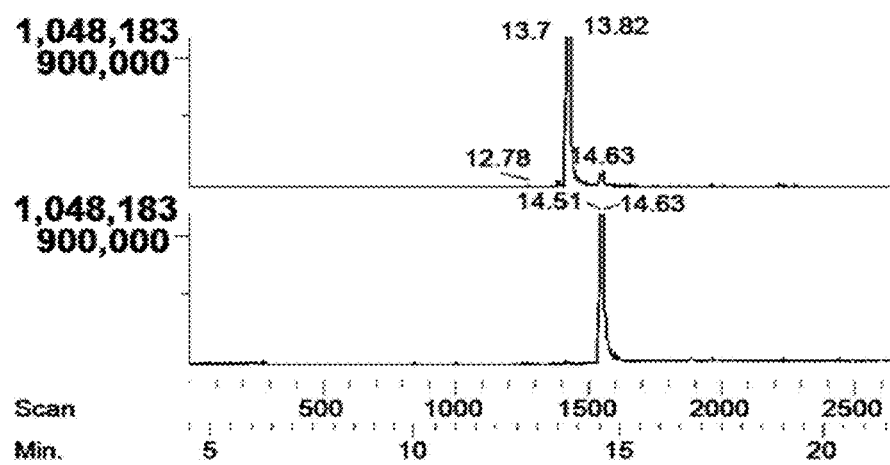
Figure 3J:
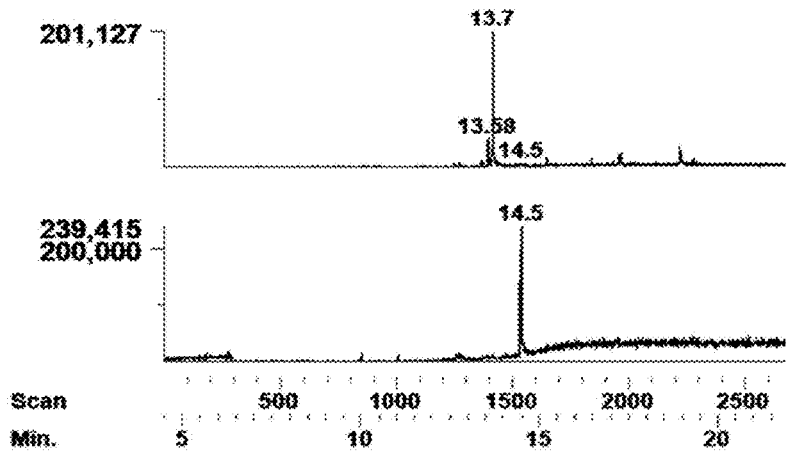
Figure 3K:
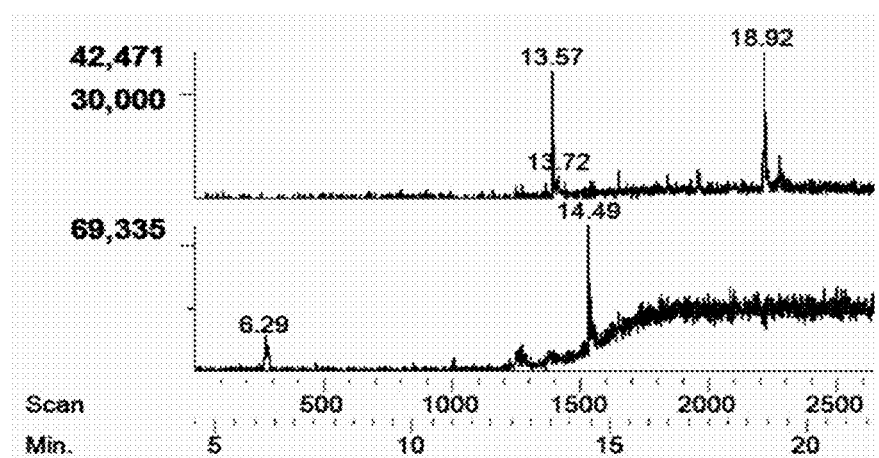
Figure 3L:
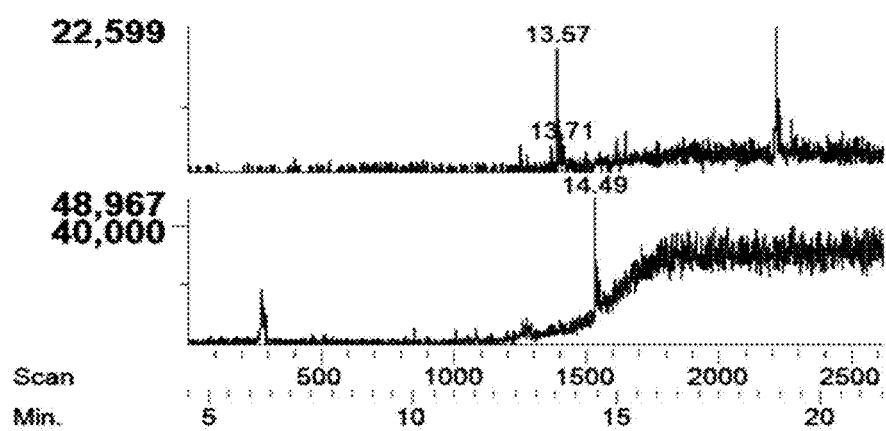

Lentivirus-mediated de novo expression studies were performed, where wild type full-length (GFP-FLPpara) was overexpressed and three different LBD-mutated PPARα (GFP-Y314D, GFP-Y464D and GFP-Y314D/Y464D Ppara) recombinant proteins (FIG. 9D) were expressed in neurons followed by binding analyses with three endogenous ligands. Briefly, site directed mutagenesis was performed in the mouse PPARα with Y314 and Y464 residues replaced separately or together with aspartate (D). After that, the entire mouse GFP-Ppara gene (GFP-FLPpara) and three different mutated genes were cloned in the pLenti6V5-TOPO lentiviral expression vector (FIG. 3D), packaged in lentivirus particle with HEK293FT cells, purified full length and mutated PPARα proteins in a GFP-affinity column, and finally thermal shift assays were performed in order to analyze their conformational stability. Both full length (FIG. 3E, FIG. 9E) and mutated (FIG. 3F, FIG. 9F) proteins displayed a similar pattern of thermal shift with equivalent melting temperature (Tm) suggesting that the mutations in Y314 and Y464 residues did not alter the conformational stability of PPARα. Moreover, OCT, HEX and HMB did not alter the Tm in Y464D-PPARα, demonstrating that mutation of tyrosine 464 to aspartate significantly impacted the binding of these ligands to the LBD of PPARα (FIG. 9G). In another experiment, Ppara-null hippocampal neurons were transduced with different lentiviral PPARα constructs and transduction efficiencies were basically the same in all cases (FIG. 14A) and the level of PPARα was comparable in cells transduced with different constructs (FIGS. 14B-C). After 48 h of transduction, the cells were homogenized, passed through GFP-affinity column, eluted, fractionated with chloroform-methanol, and finally analyzed by GC-MS for the detection of ligands. Interestingly, we observed that the affinity-purified nuclear extract of lenti-GFP-FLPpara (FIG. 3I, FIG. 9I), but not lenti-GFP-transduced (FIG. 3H, FIG. 9H) Ppara-null neurons contained these ligands. Interestingly, the mutation of Y314 was found to partially impact the ligand binding affinity of PPARα as we detected low amount of both OCT and HEX in the nuclear extract of lenti-GFP-Y134D-Ppara transduced Ppara-null neurons (FIG. 3J, FIG. 9J). On the other hand, mutation of the Y464 completely knocked down the ligand binding affinity as we observed profound loss of ligand binding in both lenti-GFP-Y464D-Ppara (FIG. 3K, FIG. 9K) and lenti-GFP-Y314D/Y464D-Ppara (FIG. 3L, FIG. 9L)-transduced Ppara-null neurons. Throughout these analyses, we used 2,4-bis (α, α-dimethyl benzyl) phenol as an internal standard (Supplementary FIG. 5A-F). We normalized peak area of different ligands with that of internal standard and then quantified the binding affinity of these ligands with different construct of PPARα by peak integration statistics (Table 1). Taken together, the detailed GC-MS analyses clearly indicated that both Y314 and Y464 residues of the PPARα-LBD were crucial for its interaction with endogenous ligands.

Figure 4C:
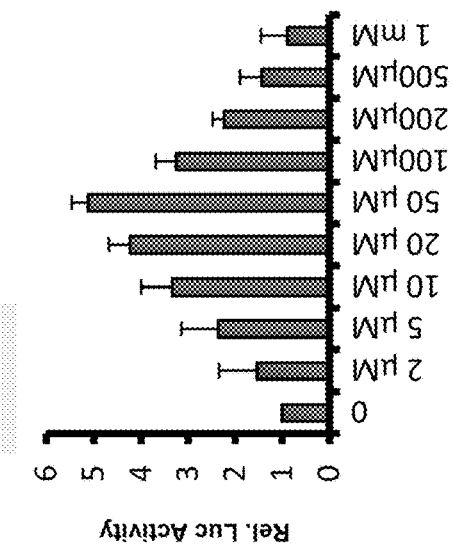
FIGS. 4A-4S. The role of endogenous ligands of PPARα in PPRE-driven luciferase activity in mouse primary astrocytes and neurons.
(FIG. 4D) a cartoon represents the details of PPRE luciferase assay in primary cells infected with lentivirus particles of different PPARα constructs. PPRE luciferase activity was assayed in mouse primary astrocytes transduced with (FIG. 4E) only vector, (FIG. 4F) FLPpara, (FIG. 4G) Y314D, (FIG. 4H) Y464D, and (FIG. 4I) Y314D/Y464D PPARα genes after the treatment of different doses of HEX, OCT, and HMB. PPRE luciferase activity in mouse primary astrocytes pre-infected with lent viruses after the treatment of increasing doses of Wy14643, fenofibrate, and clofibrate [(FIG. 4J) only vector, (FIG. 4K) FLPpara, (FIG. 4L) Y314D, (FIG. 4M) Y464D, and (FIG. 4N) Y314D/Y464D]. PPRE luciferase activity was assayed in mouse primary hippocampal neurons transduced with (FIG. 4O) only vector, (FIG. 4P) FLPpara, (FIG. 4Q) Y314D, (FIG. 4R) Y464D, and (FIG. 4S) Y314D/Y464D PPARα genes after the treatment of different doses of HEX, OCT, and HMB. Results are mean±SD of three independent experiments.
Figure 4B:
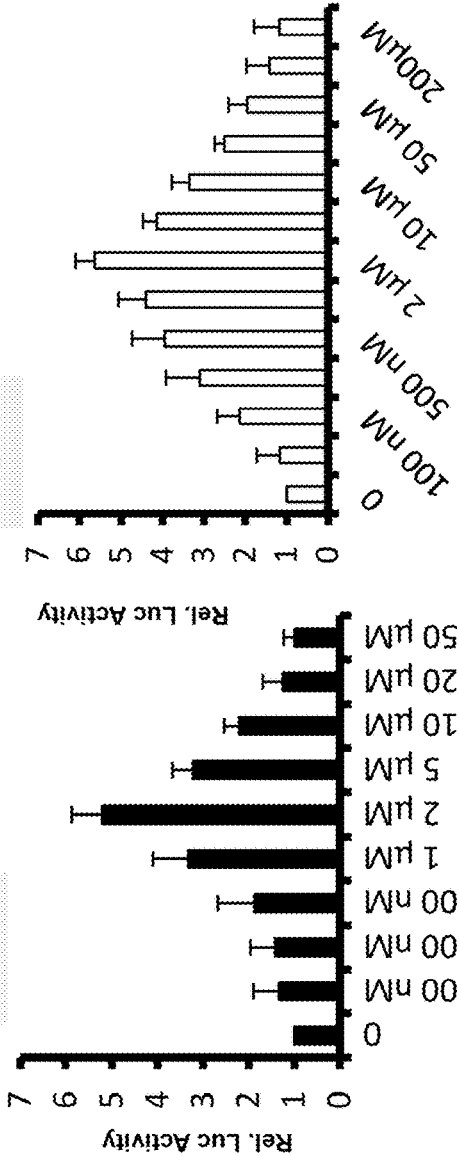
Figure 4A:
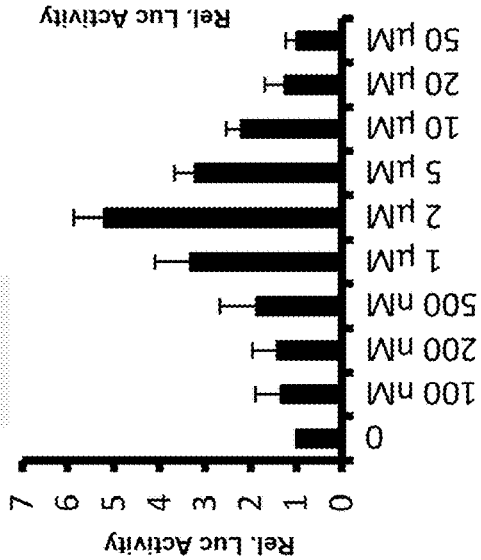
Figure 4D:
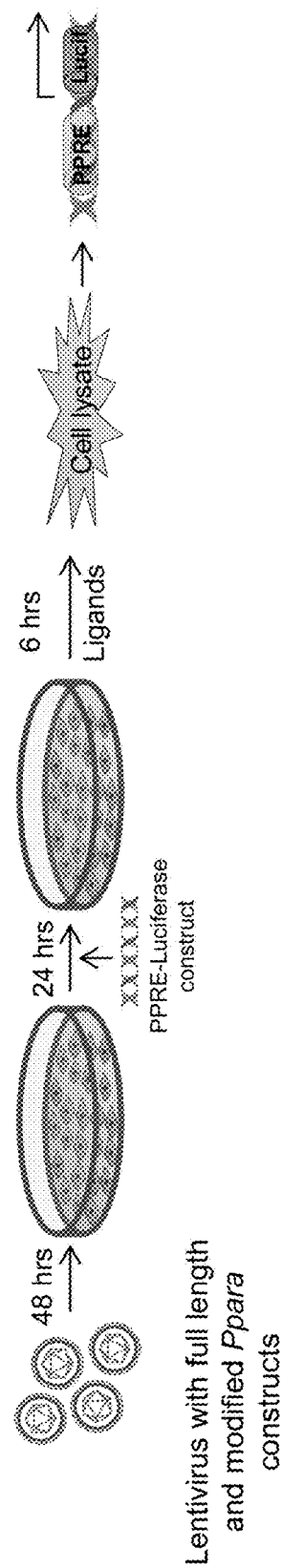
Figure 4E:
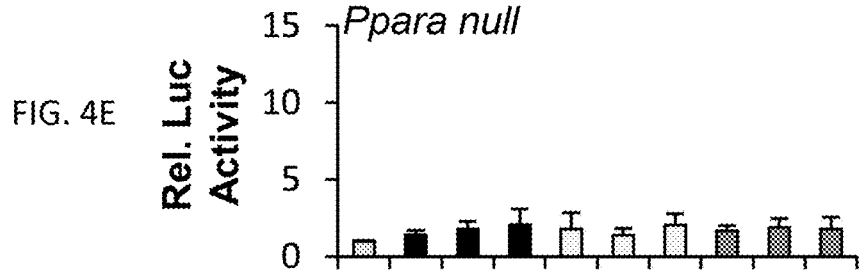
Figure 4F:
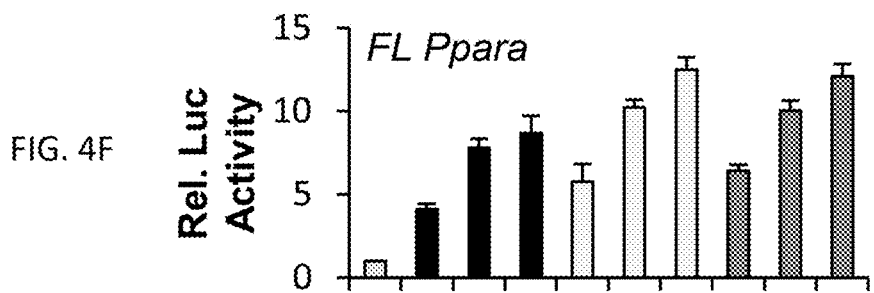

Next, the role of these ligands in controlling the transcriptional activity of PPARα was monitored. First, a PPRE-driven luciferase activity assay was performed in cultured astrocytes treated with different concentrations of OCT (FIG. 4A, FIG. 10B), HEX (FIG. 4B, FIG. 10A), and HMB (FIG. 4C, FIG. 10C). All three ligandsligands increased the PPRE luciferase activity in a dose dependent manner (FIG. 10A-C.). However, PPRE-luciferase gene-transfected astrocytes displayed significant level of cytotoxicity with higher concentrations of HEX (FIG. 10D), OCT (FIG. 10E) and HMB (FIG. 10F), justifying the decrease of PPRE-luciferase activity with higher doses of ligands (FIGS. 10A-C). Consistent with the TR-FRET assay, both OCT and HEX increased PPRE-luciferase activity at much lower concentration as compared to HMB (FIG. 10A-C.). Similarly, these ligands were also able to induce PPRE luciferase activity in Ppara null astrocytes transduced with lenti-FLPPara (FIG. 4E, FIG. 10E), but not lenti-vector (FIG. 10D.).

Figure 4G:
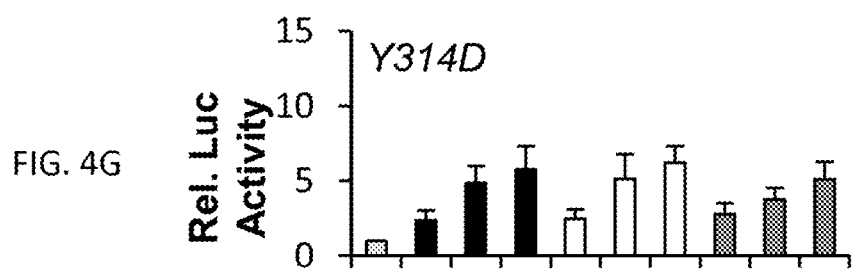
Figure 4H:
Figure 4I:
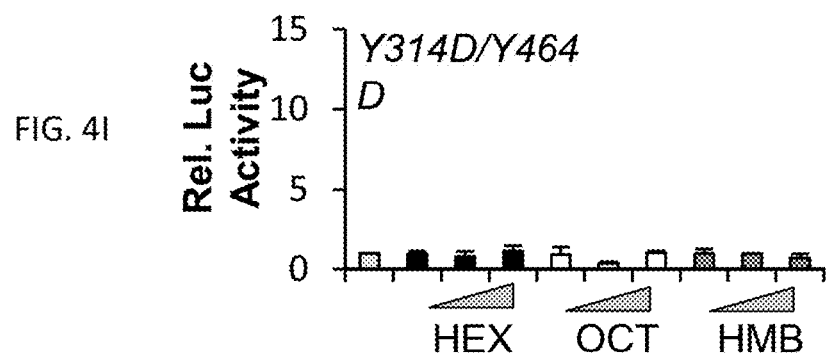
Figure 4J:
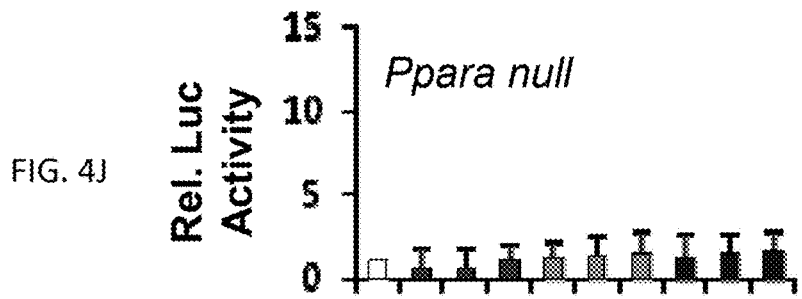
Figure 4K:
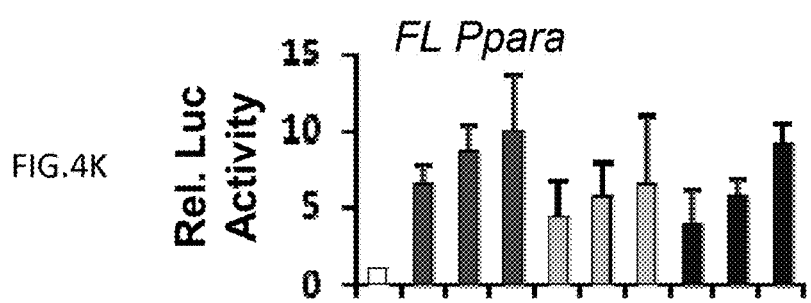
Figure 4L:
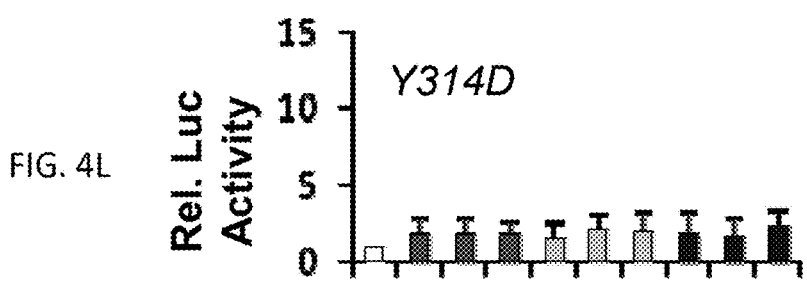
Figure 4M:
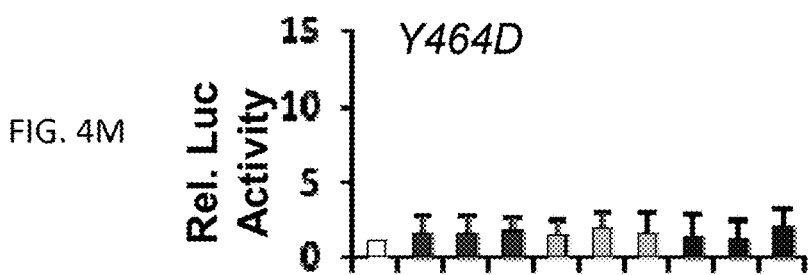
Figure 4N:
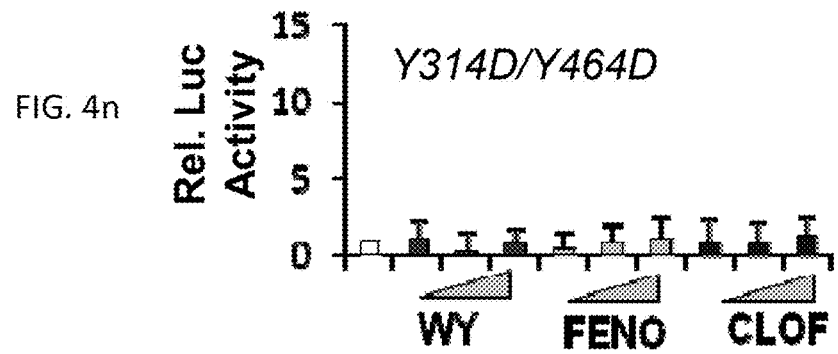
Figure 4O:
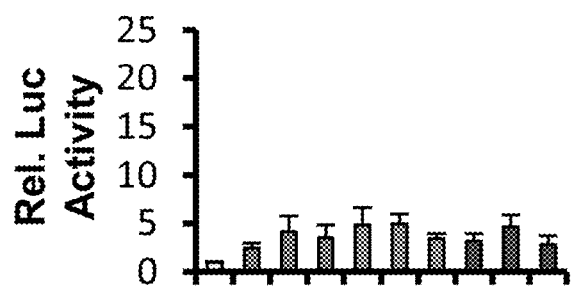
Figure 4P:
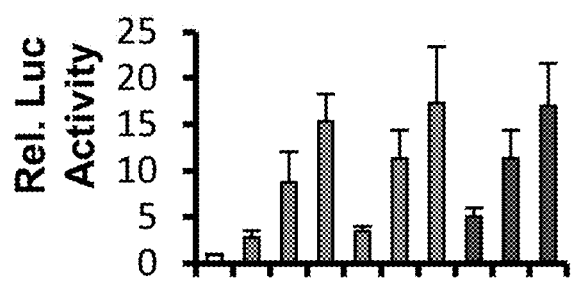
Figure 4Q:
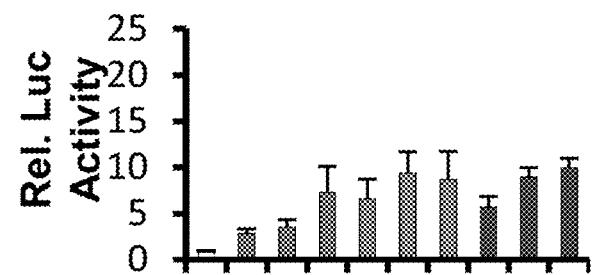
Figure 4R:
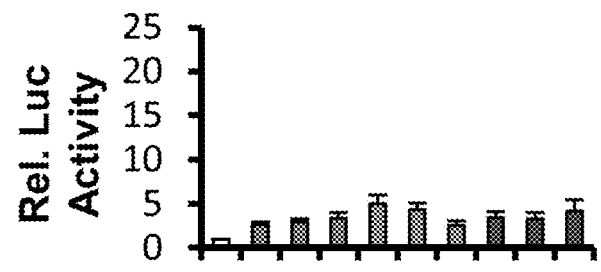
Figure 4S:
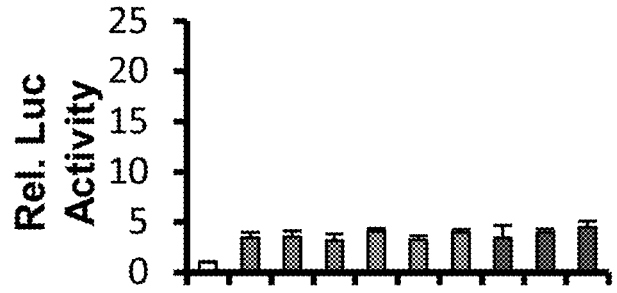
Figures 5E, 5F, 5G, 5H, 5I, 5J, 5K, 5L:
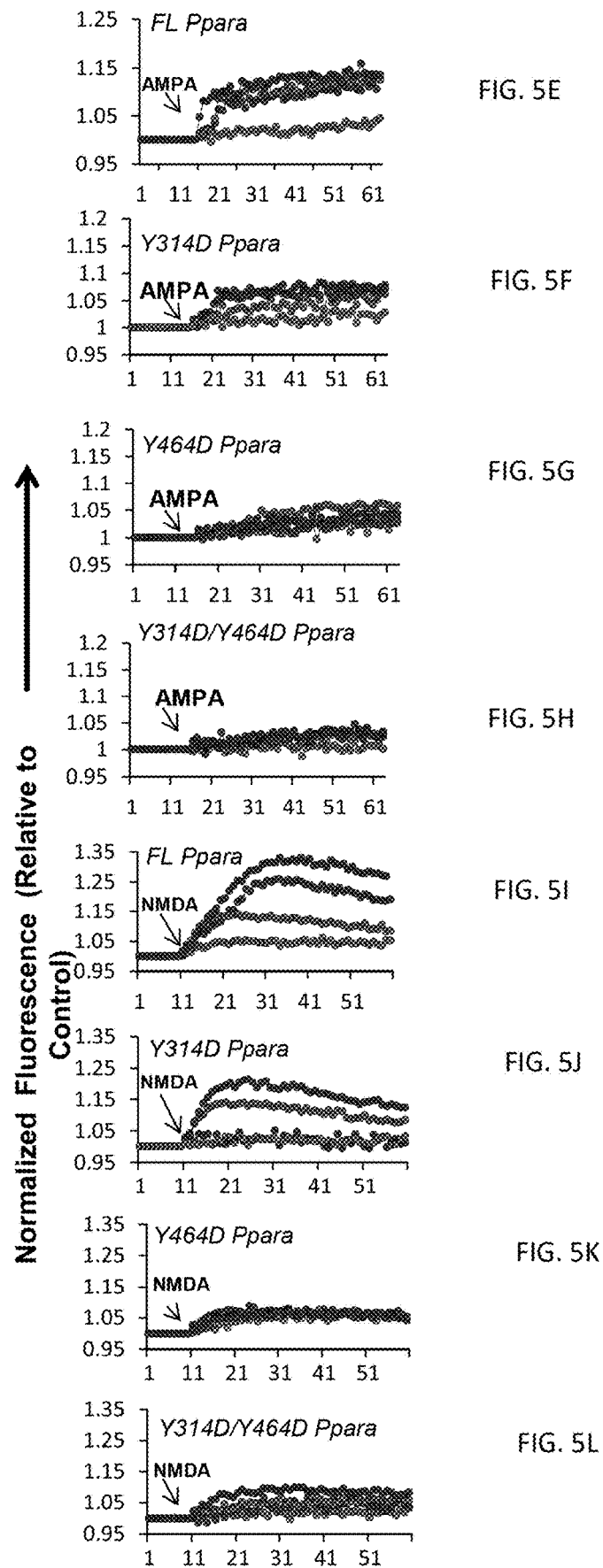
Figure 11G:
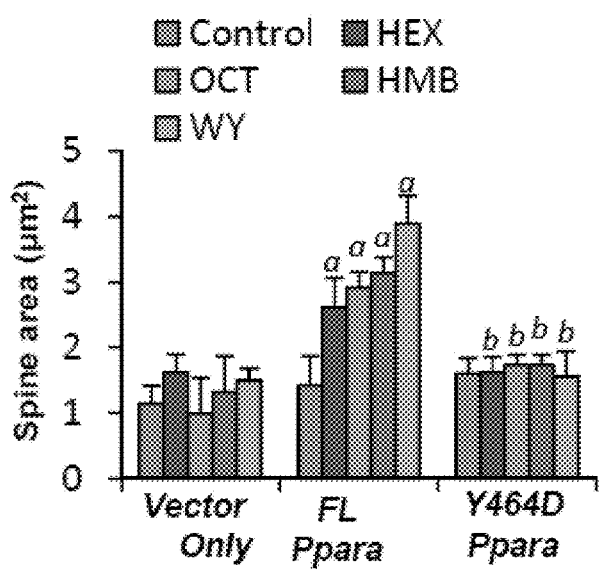
Figure 11H:
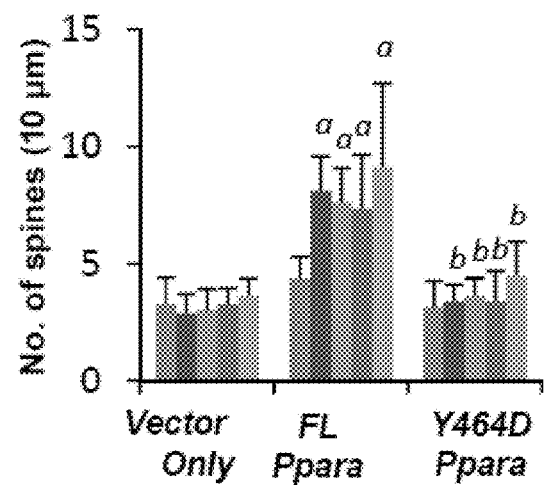
Figure 16F:
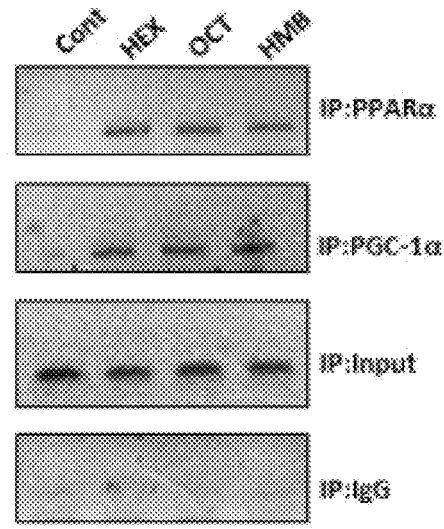
Figure 16G:
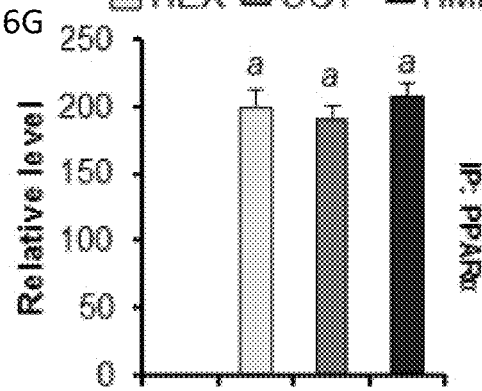
Figure 16H:
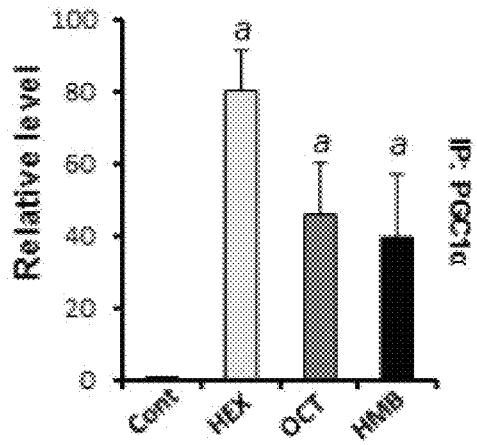

To further confirm the specificity of these ligands to PPARα, we performed PPRE-luciferase assay in PPARβ KO (Pparb-null) astrocytes. These astrocytes were pre-treated with PPARγ-antagonist GW9662 to nullify the involvement of PPARγ in reporter assay. Inhibition of rosiglitazone-mediated increase in PPRE-luciferase activity by GW9662 (FIG. 16A) suggests that this inhibitor is capable of suppressing the function of PPARγ in Pparb-null astrocytes. OCT (FIG. 16B), HEX (FIG. 16C) and HMB (FIG. 16D) markedly increased PPRE luciferase activity in Pparb-null astrocytes. Interestingly, GW9662 remained unable to inhibit OCT-, HEX- and HMB-mediated increase in PPRE-luciferase activity in Pparb-null astrocytes (FIG. 16B-D), indicating the specificity of these ligands towards PPARα. To further confirm this finding, we performed ChIP analyses of the CREB promoter (FIG. 16E) as described recently[6] and observed that all three ligands stimulated the recruitment of PPARα and its coactivator PGC1α to the CREB promoter (FIGS. 16F-H). Since Y314 and Y464 residues of PPARα-LBD were crucial for the interaction with hippocampal ligands, we examined whether these residues were also involved in hippocampal ligand-mediated activation of PPARα. As expected, HEX, OCT and HMB remained unable to induce PPRE-driven luciferase activity in Ppara-null astrocytes (FIG. 11G). However, all three ligands markedly induced PPRE reporter activity in Ppara-null astrocytes that were transduced with lentivirions containing FL-Ppara (FIG. 10H). On the other hand, Y314D mutation in PPARα-LBD displayed partial induction of PPRE-luciferase activity (FIG. 4G, FIG. 10I) as we observed in our GC-MS analysis that the interaction of all three ligands was partially compromised with Y314D PPARα. Consistent with the GC-MS results, all three ligands were unable to stimulate PPRE-luciferase activity in Ppara-null astrocytes infected with lentiviruses containing either Y464D-Ppara (FIG. 4H, FIG. 10J) or Y314D/Y464DPpara (FIG. 4I, FIG. 10K) viruses, suggesting that the Y464D mutation is sufficient to knockdown PPARα activation by its endogenous hippocampal ligands. Commercial ligands of PPARα (WY14643, fenofibrate and clofibrate) were also unable to induce PPRE-luciferase activity in Ppara-null astrocytes (FIG. 10L). However, these commercial ligands markedly induced PPRE-luciferase activity in Ppara-null astrocytes that were transduced with lenti-FL-Ppara (FIG. 10M). On the other hand, commercial ligands of PPARα displayed no luciferase activity when Ppara-null astrocytes were transduced with lenti-Y314D-Ppara (FIG. 4L, FIG. 10N), lenti-Y464D-Ppara (FIG. 4M, FIG. 10O), and lenti-Y314D/Y464D-Ppara (FIG. 4N, FIG. 10P) suggesting that both Y314 and Y464 residues of PPARα are important for the binding with commercially available ligands. Similar to astrocytes, the transduction of either lenti-Y464D-Ppara (FIG. 4R, FIG. 10T) or lenti-Y314D/Y464D-Ppara (FIG. 4S, FIG. 5U), but neither lenti-FL-Ppara (FIG. 4P, FIG. 10Q-R) nor lenti-Y314D-Ppara (FIG. 4Q, FIG. 10S), completely abrogated the PPRE-luciferase activity in OCT-, HEX-, and HMB-treated Ppara-null hippocampal neurons. Collectively, these results suggest a mandatory role for the Y464 residue and a partial role for the Y314 residue in the binding and activation of PPARα by endogenous hippocampal ligands.

The role of the endogenous ligands of PPARα in regulating the synaptic function of hippocampal neurons Next, we investigated whether these hippocampal ligands were capable of improving synaptic function of hippocampal neurons. Immunoblot (FIG. 17A) followed by relative densitometric analyses (FIG. 17B-D) and immunofluorescence analyses of NR2A (FIG. 17E) and GluR1 (FIG. 17F) clearly demonstrated that HEX, OCT and HMB upregulated, NR2A, GluR1 and CREB in WT, but not Ppara-null, hippocampal neurons, suggesting that these ligands increased the expression of synaptic molecules via PPARα.

Dendritic spines are the crucial mediators of synaptic transmission among central neurons and often serve as a primary candidate for the long term morphological substrates of neuronal plasticity[12,13]. Therefore, the effect of these ligands on the increase of spine density in cultured hippocampal neurons was studied. Briefly, mouse Ppara-null hippocampal neurons were transduced with lentivirus containing empty vector, FL-Ppara, or Y464D-Ppara for a week followed by the treatment with OCT, HEX, and HMB for four more days. After that, neurons were labelled with phalloidin to monitor the spine density. Interestingly, the transduction of Ppara-null neurons with lenti-Y464D-Ppara, but not lenti-FL-Ppara, significantly attenuated the density of dendritic spines (FIG. 5A, FIG. 11A). Moreover, the treatment with OCT (FIG. 5B, FIG. 11B), HEX (FIG. 5C, FIG. 11C), and HMB (FIG. 5D) and the synthetic agonist WY14643 (FIG. 11D) stimulated the density of spines only when Ppara-null neurons were transduced with lenti-FL-Ppara, but not with lenti-Y464D-Ppara further suggesting that the PPARα Y464 residue is crucial for the induction of morphological plasticity by its endogenous ligands. This observation was further validated by measuring the area of spine heads (FIG. 11F-G) and number of spines (FIG. 11H) in HEX, OCT, and HMB-treated Ppara-null neurons. HEX (FIG. 17G-H), OCT (FIG. 17I-J) and HMB (FIG. 17K-L) stimulated the expression of CREB in Ppara-null hippocampal neurons that were transduced with lentivirons containing the FL-Ppara gene. On the other hand, HEX, OCT and HMB remained unable to increase the expression of CREB in Ppara-null hippocampal neurons that were transduced with lenti-Y464D-Ppara and lenti-Y464D/Y314D-Ppara(FIG. 17G-L). Moreover, Y314D mutation only partially restored the expression of CREB in response to OCT, HEX, and HMB in lenti-Y314D-Ppara transduced Ppara-null neurons (FIG. 17G-L).

Figure 6A:
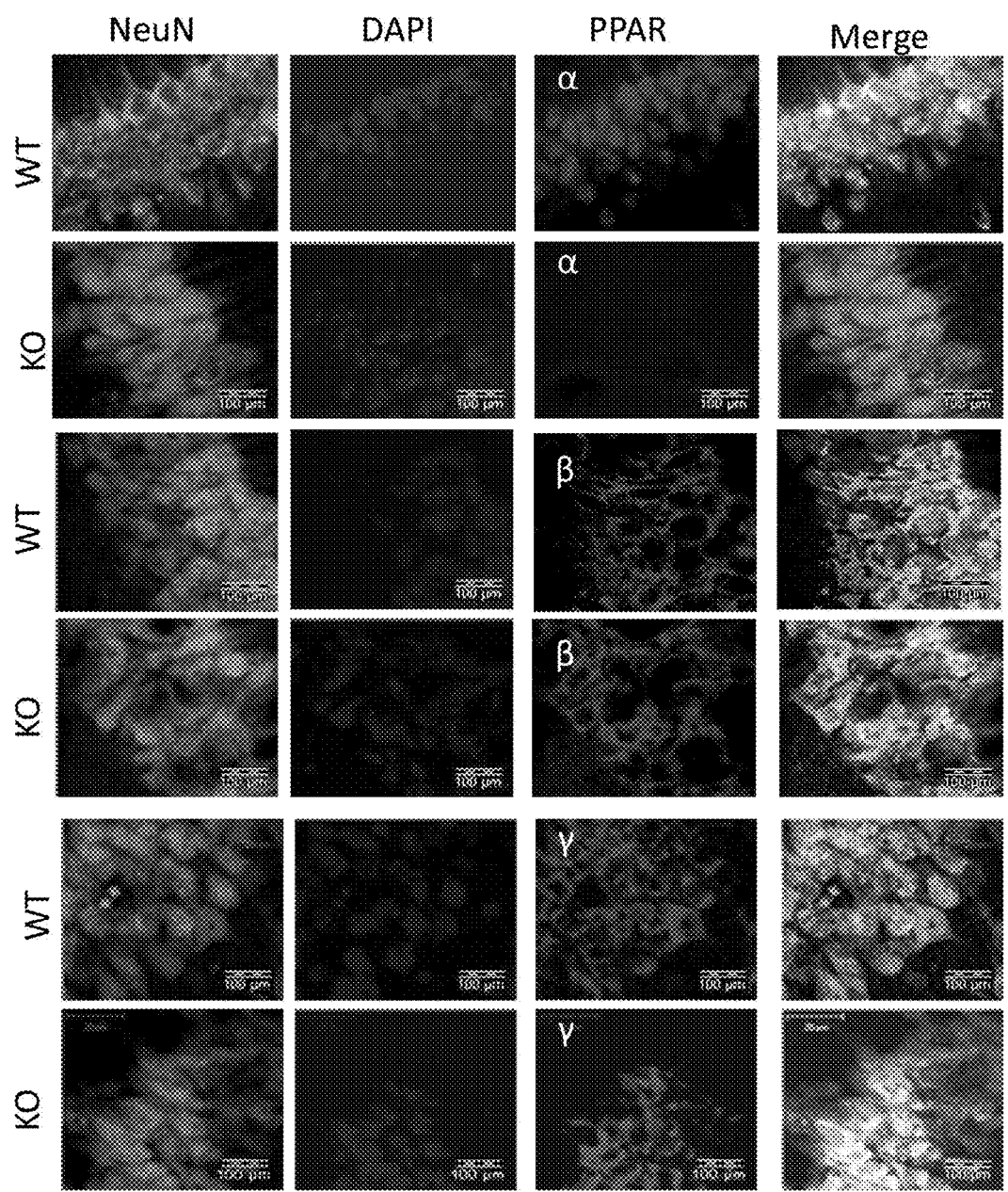
FIGS. 6A-6B. The subcellular localization of PPARα, β and γ isotypes in mouse brain hippocampus.
Figure 6B:
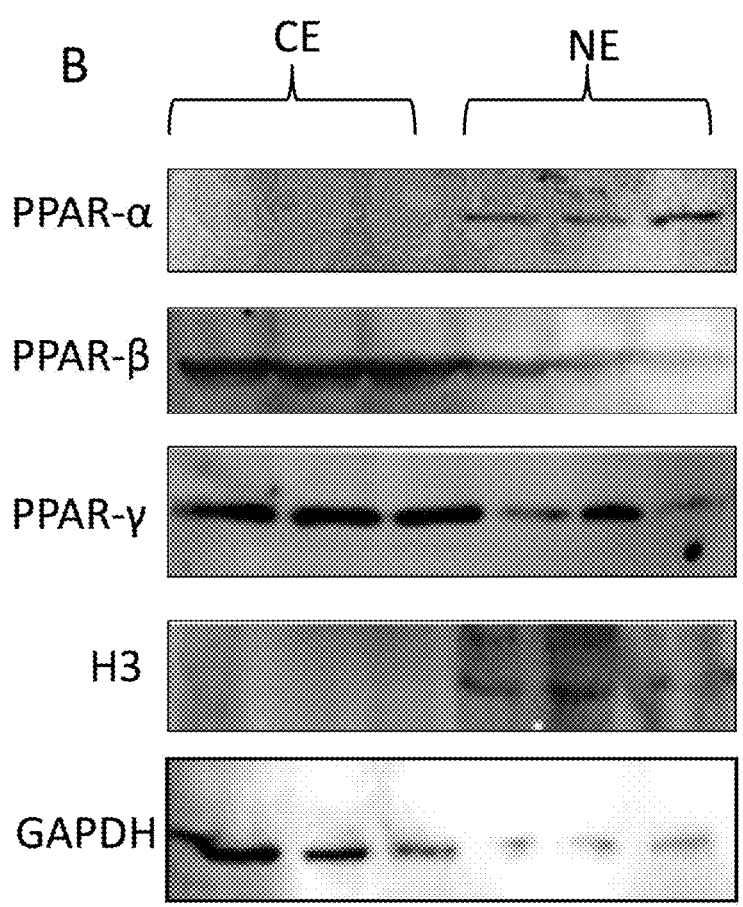

Calcium oscillation through metabotropic receptors has been implicated in synaptic plasticity and recently we have demonstrated that both AMPA and NMDA elicited much weaker calcium influx and a smaller amplitude oscillation in Ppara-null than WT hippocampal neurons[6]. Consistently, we have seen that HEX, OCT and HMB stimulated AMPA- and NMDA-medicated calcium influx in lenti-FL-Ppara-tranduced Ppara-null hippocampal neurons (FIG. 11I-P). However, HEX, OCT and HMB remained unable to increase AMPA—(FIG. 5E-H, FIG. 11I-L) and NMDA-(FIG. 5I-L, FIG. 11M-P) mediated calcium influx in Ppara-null hippocampal neurons that were transduced with either lenti-Y464D-Ppara or lenti-Y314D/Y464D-Ppara. On the other hand, lenti-Y314D-Ppara was only able to partially restore HEX-, OCT- and HMB-elicited calcium influx in AMPA- or NMDA-treated Ppara-null hippocampal neurons (FIGS. 6J & M). These results suggest pivotal role of Y464 residue and limited role of Y314 residue of PPARα in OCT-, HEX-, and HMB-stimulated calcium influx through NMDA and AMPA-sensitive receptors.

Discussion

Since PPARα has been reported to be localized in the different parts of the brain[32] and might play crucial role in controlling different brain function[6,14], there is a growing interest in identifying the endogenous agonist for PPAR-α in this tissue. Although different studies speculated anandamides or 9-olylethanolamide could serve as central ligands of PPARα[15], there is no experimental evidence that shows the molecular interaction between 9-oleoylethanolamide and PPARα, however 9-oleoylethanolamide was shown to display PPARα-independent effects[16]. Moreover, there are many structurally similar fatty acyl amides available in the CNS that have not been evaluated as potential endogenous ligands of PPARα. The isolation and characterization of three novel ligands of PPARα have been delineated (octadecenamide (OCT), hexadecanamide (HEX), and 3-hydroxy-2,2-dimethyl butyrate (HMB)) from the hippocampus. First, GC-MS analyses of PPARα LBD-pulled down fraction of hippocampal nuclear extract revealed the existence of these compounds. Interestingly, these three compounds were detected only in PPARα LBD-, but not PPARβ LBD-pulled down fraction of hippocampal nuclear extract, suggesting that these ligands are specific for PPARα. In addition to these three major ligands, we also detected some thionated compounds including thiazoles (mw 220-240), thiosemicarbazones (mw 190-200), and thiazolidine esters (mw 250-270) while performing GC-MS analyses. Second, de novo establishment of PPARα by lentiviral transduction of the Ppara gene in Ppara-null hippocampal neurons followed by similar GC-MS analysis also resulted in the detection of these three ligands. Third, further characterization of these molecules by TR-FRET and thermal shift assay revealed that HEX, OCT and HMB strongly interacted with the LBD of PPARα. The high-throughput studies indicated that all three ligands served as full ligands of PPARα as we observed the slope of the curve derived from both FRET and thermal-shift assay shifted along the positive direction of X axis. While measuring their affinity, EC50 values of these ligands ($EC50_{OCT}$=4.31 μM; $EC50_{HEX}$=4.36 μM; $EC50_{HMB}$=31.6 μM) were observed higher than the same for GW7647($EC50$=6.62 nM), a pharmacological agonist of PPARα (FIG. 18). These results suggest that these newly discovered hippocampal ligands have less affinity compared to commercially available ligands.

The in silico analysis, site-directed mutation of Y314 and Y464 residues of PPARα followed by lentiviral manipulation of these genes in Ppara-null hippocampal neurons revealed minimal binding of PPARα with these ligands as evident from the GC-MS analyses. The results also found that both Y314 and Y464 residues of PPARα are involved in the interaction with these ligands, with the PPARα Y464 residue being more critical than the Y314 residue in terms of its interaction with the endogenous ligands. This observation was further validated by analysis of the transcriptional activity of PPARα via PPRE luciferase assays where Y464D mutation of PPARα did not restore PPRE-luciferase activity in OCT-, HEX-, and HMB-treated Ppara-null hippocampal neurons. The mutation of tyrosine to aspartate might generate a conformational instability to PPARα protein. However, the thermal melting curve of FL-PPARα and mutated PPARα did not show much difference in terms of the melting temperature of the protein suggesting that this mutation does not affect the conformational stability of PPARα. Previous studies have reported the 9-oleylethanolamine could serve as a ligand for PPARα in the brain; however we could not detect 9-oleylethanolamine in hippocampus by GC-MS after pulling down the hippocampal extracts with recombinant PPARα LBD. One possibility is that PPARα LBD has been pulled down only from the nuclear extracts and that 9-oleylethanolamine is not present in the nucleus. The nuclear fraction of PPARα was targeted for its ligand detection as PPARα is constitutively present in nuclei of hippocampal neurons.

Recently, it has been shown that PPARα regulates the transcription of CREB and controls the expression of CREB-associated synaptic genes[6]. In another study, we have shown that statin-mediated nuclear activation of PPARα is also important to regulate the expression of neurotrophins in different brain cells[31]. Our detailed molecular interaction analyses reveal that statins interact with L331 and Y334 residues of PPARα LBD in the presence of PGC1α and controls the transcription of CREB. However, commercially available ligands and the endogenous ligands described in this study, do not interact with these two residues of PPARα. Instead, these molecules interact with Y314 and Y464 residues of the PPARα LBD. Our site-directed mutagenesis studies followed by GC-MS analyses confirmed that these residues of PPARα controlled its association with endogenous ligands, however PPARα Y464 residue appeared to be more crucial than Y314. Moreover, the PPRE-driven reporter assay indicated that the mutation of Y464 of PPARα completely abolished the activation of PPARα, whereas the mutation of Y314 only partially compromised the transcriptional efficiency of PPARα suggesting the importance of Y464 in the PPARα-LBD is the most crucial amino acid residue for its interaction with endogenous ligands.

Characterizing drugs for improving synaptic plasticity is an important area of research. Interestingly, these hippocampal ligands increased synaptic properties of hippocampal neurons. However, these compounds stimulated the expression of different synaptic molecules in WT, but not in Ppara-null neurons. Stimulation of dendritic spine formation and increase in NMDA- and AMPA-driven calcium influx by hippocampal ligands in Ppara-null hippocampal neurons upon establishment of FLPpara, but not Y464DPpara, indicates the importance of Y464 residue of PPARα in synaptic properties of hippocampal ligands. While Y464 residue of PPARα was fully responsible for the functioning of these ligands, Y314 residue was also partly involved in this process. Earlier studies suggest that OCT could be beneficial in controlling sleep as it has been found in the cerebrospinal fluid during sleep deprivation[34]. Since OCT and two other compounds HEX and HMB are constitutively present in the hippocampus as PPARα ligands, it would be interesting to see if these compounds increase sleep via PPARα.

Materials and Methods:

Animals: Animal maintaining and experiments were in accordance with National Institute of Health guidelines and were approved by the Institutional Animal Care and Use committee of the Rush University of Medical Center, Chicago, Ill. Ppara-null and their wild-type (WT) controls were purchased from Jackson Laboratory. Mice were housed in ventilated micro-isolator cages in an environmentally controlled vivarium (7:00 A.M./7:00 P.M. light cycle; temperature maintained at 21-23° C.; humidity 35-55%). Animals were provided standard mouse chow and water ad libitum and closely monitored for health and overall well-being daily by veterinary staff and the investigator.

Reagents: Rabbit polyclonal anti-PPARα antibody (Abcam; Cat #ab189159; WB and IHC), mouse anti-NeuN antibody (Millipore; Cat #MAB377), rabbit polyclonal anti-PPARβ antibody (Abcam; Cat #ab8937; WB and IHC), anti-PPARγ antibody (Abcam; Cat #ab66343; WB and IHC), anti-NMDAR2A antibody (Cell Signaling for WB at a dilution of 1:1000, Cat #4205; Abcam for IHC, Cat #ab169873), anti-GluR1 antibody (Cell Signaling for WB at a dilution of 1:1000, Cat #13185; Abcam for IHC, Cat #ab131507), anti-CREB antibody (Cell Signaling for WB at a dilution of 1:1000 and IC at a dilution of 1:200, Cat #9104), and anti-Arc antibody (Abcam for WB at a dilution of 1:1000, Cat #ab118929) were used in this study. Different pharmacological compounds including 9-octadecenamide (Cat #02136), hexadecanamide (Cat #S350435), 2,4-bis(α, α-dimethyl benzyl) phenol (Cat #372129), gemfibrozil (Cat #G9518), clofibrate (Cat #C6643), fenofibrate (Cat #F6020), GW9662 (Cat #M6191), WY-14643 (Cat #C7081), and MTT-based toxicity assay kit (Stock No. TOX-1) were purchased from Sigma-Aldrich. GST-PPARα-LBD and GST-PPARβ-LBD were purchased from Protein One. On the other hand, 3-hydroxy 2,2-dimethyl butyric acid ethyl ester (Cat #sc-216452) was purchased from Santa Cruz.

Isolation of Mouse Hippocampal Neurons: Hippocampal neurons were isolated from fetuses (E18) of pregnant female Ppara-null and strain-matched WT littermate mice as described by us [6,13,35-36] with some modifications. Briefly, dissection and isolation procedures were performed in an ice-cold, sucrose buffer solution (sucrose 0.32 M, Tris 0.025 M; pH 7.4)[37]. The skin and the skull were carefully removed from the brain by scissors followed by peeling off the meninges by a pair of fine tweezers. Next, a fine incision was made in the middle line around the circle of Willis and medial temporal lobe was opened up. Hippocampus was isolated as a thin slice of tissue located near the cortical edge of medial temporal lobe. Hippocampal tissues isolated from all fetal pups (n>10) were combined together and homogenized with 1 ml of trypsin for 5 minutes at 37° C. followed by neutralization of trypsin. The single cell suspension of hippocampal tissue was plated in the poly-D-lysine pre-coated 75 mm flask. Five min after plating, the supernatants were carefully removed and replaced with complete neurobasal media. The next day, 10 μM AraC was added to remove glial contamination in the neuronal culture. The pure cultures of hippocampal neurons were allowed to differentiate fully for 9-10 days before treatment[35,36,38].

Isolation of Mouse Astrocytes: Astrocytes were isolated from mixed glial cultures of 7 d old mouse pups according to the procedure of Guilian and Baker[39] as described earlier[17,31,40].

Lentiviral cloning of FLPpara and mutated Ppara (ΔsbdPpara):

Site Directed Mutation:

Mouse PPARα ORF cloned in pCMV6-AC-GFP vector (cat #MG 227641) was purchased from Origene. MG227641 was mutated at Tyr314 with aspartate (Y314D) and Tyr464 with aspartate (Y464D) by site-directed mutation kit (Stratagene)[6]. Two primers in opposite orientation were used to amplify the mutated plasmid in a single PCR reaction. The PCR product was precipitated with ethanol and then phosphorylated by T4 kinase. The phosphorylated fragment was self-ligated by T4 DNA ligase and digested with restriction enzyme Dpnl to eliminate the non-mutated template. The mutated plasmid was cloned and amplified in *Escherichia coli* (DH5-a strain) competent cells.

Generating pLenti6.3/V5-TOPO® constructs of FLPpara and ΔsbdPpara

Briefly, each construct was amplified by PCR, using primer pair (sequence) and every product had a single adenosine (A) to the 3' end. Then the TOPO cloning reaction was performed using Invitrogen kit (K5315-20) with pLenti6.3N5-TOPO vector. For transformation One-Shot Stbl3 competent cells were used. Sequencing of the clones was performed at ACGT Inc.

Producing Lentivirus in 293FT Cells

293FT cells were cultured with 95% confluency in Opti-MEM media without antibiotics. Next day, ViraPower™ Packaging Mix (9 μg/reaction) and pLenti expression plasmid DNA containing either FLPpara or ΔsbdPpara (3 μg/reaction) (12 μg total) were mixed in 1.5 mL of serum-free Opti-MEM® I Medium. In another tube, 36 μL of Lipofectamine® 2000 was added in 1.5 mL of serum-free Opti-MEM® I Medium with gentle mix. After 5 minutes of incubation at room temperature, both the reactions were combined and incubated for 20 mins. After that, the mixture was applied to HEK-293FT cells and incubated overnight at 37° C. in a humidified 5% $CO_2$ incubator. The next day, the media was replaced with serum-free Opti-MEM media and further incubated for 48-72 hrs at 37° C. in a humidified 5% $CO_2$ incubator and then supernatant containing viral particles was collected. Viral particles were concentrated with lenti-concentrator solution and MOI was calculated.

Isolation of Nuclear Extracts and Gas Chromatography Mass Spectra (GC-MS) analysis of PPARα-ligand interaction Sample Preparation Either E18 cultured mouse hippocampal neurons or hippocampal tissue of 6-8 week old male C57/BL6 mice were homogenized in ice-cold nondetergent hypotonic buffer [10 mM HEPES (pH 7.9), 1.5 mM $MgCl_2$, 10 mM KCl, 100 mM DTT, protease and phosphatase inhibitor cocktail]. After 10 min of additional incubation in the hypotonic buffer, the homogenate was centrifuged at 8,000 g at 4° C. for 10 min. Next, the pellet was homogenized in ice-cold extraction buffer [10 mM HEPES (pH 7.9), 1.5 mM $MgCl_2$, 0.21 M NaCl, 0.2 mM EDTA, 25% (v/v) glycerol, 100 mM DTT, protease and phosphatase inhibitor cocktail], placed on a rotating shaker at 4° C. for 1 h, and then centrifuged at 18,000 g for 10 min. The supernatant (nuclear fraction) was incubated with 1.5 μg of GST PPARα LBD (Protein One) at 4° C. for 6 h in a rotating shaker. The reaction mixture was passed through glutathione column (Pierce® GST Spin Purification Kit), washed four times [50 mM Tris HCl (pH 7.4), 100 mM NaCl, protease and phosphatase inhibitor cocktail] and then eluted with free glutathione. The eluate was transferred to methanol: chloroform: water (4:3:1) mixture and then centrifuged at 14,000 rpm for 90 sec. The organic phase was collected, evaporated in the SpeedVac, reconstituted with 30 μL chloroform or acetonitrile, and then analyzed by GC-MS. In another case, E18 cultured hippocampal neurons were transduced with lentiviral particles conjugated with PPARα-LBD or different GFP-tagged mutated constructs followed by pulling down with anti-PPARα antibody or passing the extract through GFP-column of Vector Fusion-Aid GFP Kit (Cat #MB-0732). After that, the eluate was collected from the column with 5M NaCl solution, concentrated with PD-10 desalting column and analyzed for GC-MS.

GC-MS Analyses

A JEOL GCMate II (JEOL USA, Peabody Mass.) mass spectrometer was used in these experiments. The gas chromatograph was an Agilent 6890Plus (Wilmington Del.) equipped with a G1513A auto-injector with 100 vial sample tray connected to a G1512A controller. The gas chromatography column was a fused silica capillary column with a nonpolar 5% phenyl 95% dimethylpolysiloxane phase (Agilent HP-5 ms), 30 meters long, 0.25 mm internal diameter, 0.25 μm film thickness. The carrier gas was Helium (99.9995% Research Grade) run through a STG triple filter (Restek Corp.) at a constant flow rate 1.1 mL/min. The injector was held at 275° C. and was fitted with an Agilent 4 mm ID single taper split liner containing deactivated glass wool. One μL of solution was injected at a split ratio of 20:1. The initial oven temperature was 40° C. held at 2 min, raised to 300° C. at a rate of 10° C. (FIG. 2A-E) or 20° C. (FIGS. 2K & 2L) per min, then held for 17 min (FIG. 2A-E) or 30 min (FIGS. 2K & 2L). This explains the variable retention times of the identified compounds. Total run time was 45 min.

The mass spectrometer was a benchtop magnetic sector operating at a nominal resolving power of 500 using an accelerating voltage of 2500 volts. The spectrometer was operated in full scan EI mode (+Ve) with the filament operating at 70 eV scanning from m/z 10 to m/z 850 using a liner magnet scan. The scan speed was 0.3 sec per scan. The solvent delay was 4.0 min. Data analysis was performed using the TSS Pro software (Shrader analytical & Consulting Laboratories, Inc., Detroit Mich.) provided with the spectrometer. Reconstructed ion current (RIC) chromatographic peaks using ions unique to each compound were used for quantitation. Mass calibration was performed using perfluorokerosene (PFK).

In Silico structural analyses of PPARα complexed with OCT, HEX and HMB.

Ligand Preparation

Ligands (OCT, HEX and HMB) were subjected to LigPrep module implemented in Tripos software[X1], which converted the 2D to 3D structure. Then using the ionization engine, the ligand was prepared at pH 7.0±1. The appropriate stereoisomers were generated along with the low energetic conformers.

Protein Preparation

The crystal structures for PPARα (3VI8.pdb), β (3GWX.pdb), and γ (3U9Q.pdb) were imported from the pdb databank. The protein preparation module of Tripos was utilized to fix up the hydrogen bonding orientation, bond orders, charges, missing side chain atoms, missing loop, protonation at physiological pH, and side chain bumps. Finally, staged minimization was performed for all three protein structures.

Docking of the Ligands

The Surflex docking module[41] implemented in Tripos was used to carry out the docking of OCT, HEX and HMB in PPARα, β and γ crystal structures. After the docking, three major scoring functions such as Total Score (a function of −Log $K_d$), Crash Score (penalty score reflecting the inappropriate penetration of the ligand into the active site pocket) and Polar Score (depicting all the favorable polar interactions) were obtained.

We also computed the binding free energy of OCT, HEX and HMB in PPARα, using Molecular Mechanics Generalized Born Surface Area approach[42]. To account for the structural deformation upon binding, we included adaptation expense that accounts for changes in the intramolecular energetics ($\Delta G_{int}^0$). For ligand strain energy, we specified a 5 å region of the receptor from the centroid of the ligand to be flexible so that the protein structure was relaxed in the computation of the binding energy of the ligands.

To soften the potential for the non-polar part of the ligands, the van der Waals radii of the atoms were scaled to 0.8 in a regular docking experiment. This allowed the dock pose to show as a successful pose even if the distance between the ligand atoms and the protein atoms are less than 1 Å away from each other. We increased the scaling factor to 1.2, in order to eliminate the unreasonable poses.

TR-FRET Analysis

TR-FRET assay was performed using Lanthascreen TR-FRET PPAR-alpha coactivator assay kit (Cat #PV4684). In this assay, different doses of statin drugs were incubated with GST-tagged recombinant PPARα LBD protein, Terbium (Tb)-tagged anti GST antibody and Fluorescein (FL)-tagged PGC1α as directed in the manufacturer's protocol. The entire reaction was set up in corning 384 well plates by an automated robotic injector. Each plate was centrifuged, incubated in a dark place for 30 mins, and then analyzed "molecular devices analyst" machine equipped with dichroic mirror. The excitation wavelength and emission wavelength were set at 340 nm and 540 nm wavelength respectively.

Thermal Shift Assays

Thermal shift assays were performed in Applied Biosystems 7500 standard real-time thermal cycler machine with commercially available thermal shift dye kit (Life technologies; Cat #4461146). For each reaction, purified protein (0.5 µg to 1 µg) was added to 18 µL of thermal shift buffer provided with the kit, and 1-2 µL of dye. Reaction was set 96 well PCR plate in the dark and then placed in the thermal cycler machine using the following two-stage program [(25° C. for 2 mins) 1 cycle; (27° C. for 15 sec, 26° C. for 1 min) 70 cycles; auto increment 1° C. for both stages]. The filter was set at ROX with no quencher filter and no passive filter.

Microarray Analyses

RNA samples were collected from hippocampal tissue of WT and Ppara-null (αKO) mice using Qiagen RNeasy kit (Cat #74104). Quantity and purity of RNA were determined using the NanoDrop LTE (Nanodrop Technologies, Wilmington, Del., USA). The mRNA of each sample was converted into cDNA using SuperScript III First-Strand synthesis Kit (Thermofisher; Cat #18080-051). Next, each cDNA sample was diluted at 1:2 ratio, mixed with SYBR Green qPCR Master Mix (Applied Biosystems, Thermofisher; Cat #4309155), and then aliquoted on 96 well Mouse Plasticity qPCR-arrays (SABiosciences; Cat #PAMM-126Z). Then 96-well plate was placed in ABI Prism 7500 standard qPCR System and run with stage 2, step 2 (60.0° C.@1:00 min) "data collection" module. Once PCR is done, Ct values were imported from the PCR console and uploaded in SABiosciences website for further analyses. As recommended, we used online software modules to proceed with further calculations. Data normalization was performed by correcting all Ct values with the average Ct values of 12 constantly expressed housekeeping genes (HKGs) present on the array. PCR-array results were displayed by clustergram analyses with three color presentation from green (low expression) to black to red (high expression).

RT-PCR Analysis

Total RNA was digested with DNase and RT-PCR was carried out as described earlier[17,18] using a RT-PCR kit from Clontech. GAPDH (glyceraldehyde-3-phosphate dehydrogenase) was used to ascertain that an equivalent amount of cDNA was synthesized from different samples.

Real-Time PCR Analysis

Real time PCR was performed in the ABI-Prism7700 sequence detection system (Applied Biosystems, Foster City, Calif.) as described earlier[17,18] using TaqMan Universal Master mix and FAM-labeled probes and primers (Applied Biosystems). Data were processed by the ABI Sequence Detection System 1.6 software and analyzed by ANOVA.

Immunoblot Analysis

For whole-cell and tissue lysates, samples were homogenized in RIPA buffer containing protease and phosphatase inhibitors (Sigma), passed 10 times through a 26-gauge needle, rotated end over end for 30 min at 4° C., and centrifuged for 10 min at 18,000×g. The supernatant was aliquoted and stored at −80° C. until use. Protein concentrations were determined using a NanoDrop 2000 (Thermo Fisher), and 15-30 µg sample was heat-denatured and resolved on 10% or 12% polyacrylamide-SDS gels, transferred to 0.45 µm nitrocellulose membranes under semidry conditions (15V for 12 min). Membranes were blocked for 1 h with blocking buffer (Li-Cor), incubated with primary antibodies overnight at 4° C. under shaking conditions, washed, incubated with IR-dye-labeled secondary antibodies (1:17,000; Li-Cor) for 45 min at room temperature, washed, and visualized with the Odyssey Infrared Imaging System (Li-Cor). Blots were converted to grayscale and then binary, analyzed using Fiji, and normalized to appropriate loading controls.

Immunohistochemical Analysis

Hippocampal regions were dissected from 18-day-old embryonic fetus as described elsewhere (PMID: 25007337), combined and plated in poly-D-lysine coated plate for another 2-3 weeks for branching. After that, these neurons were transduced with GFP-containing lentivirions for 2 d. Neurons were stained with Dylight-554-conjugated phalloidin (Cat #21834; Thermofisher) as per manufactures protocol and visualized in fluorescence microscope. For tissue staining, 10 µm paraffin embedded mouse brain hippocampal sections were made from 8- to 10-week-old male WT and Ppara-null mice and immuno-stained with anti-PPARα and anti-NeuN antibodies.

Statistical Analyses

All values are expressed as the mean±SD. Differences among means were analyzed using one- or two-way ANOVA with dose of ligands or genotype as the independent factors. Differences in behavioral measures were examined by independent one-way or repeated-measures ANOVAs using SPSS. Homogeneity of variance between test groups was examined using Levene's test. Post-hoc analyses of between-subjects effects were conducted using Scheffe's, Tukey's or Games-Howell tests, where appropriate. $p<0.05$ was considered statistically significant.

The following experiments will be conducted to test the efficacy of HMB, HEX and OCT for treatment of neurodegenerative disorders, lysosomal storage disorders and body weight control. The examples set forth below illustrate the experiments exemplify the use of HMB. Similar experiments will be conducted with HEX and OCT.

Adoptively-Transferred Experimental Allergic Encephalomyelitis (EAE). MS Model.

Female SJL/J mice (4-5 weeks old) will be used. Donor mice will be immunized s.c. with 400 µg bovine Myelin Basic Protein (MBP) and 60 µg M. tuberculosis in Incomplete Freund's Adjuvant (IFA). Animals will be sacrificed 10-12 days post-immunization, and the draining lymph nodes will be harvested and single cell suspensions will be cultured in RPMI 1640 supplemented with 10% Fetal Bovine Serum (FBS), 50 µg/mL MBP, 50 µM 2-ME, 2 mM L-glutamine, 100 U/mL penicillin, and 100 µg/ml streptomycin. On day 4, cells will be harvested and re-suspended in Hank's balanced salt solution (HBSS). A total of $2 \times 10^7$ viable cells in a volume of 200 µL will be injected into the tail vein of naive mice. Pertussis toxin (150 ng/mouse; Sigma-Aldrich) will be injected once via i.p. route on 0 day post-transfer (dpt) of cells. Mice will be treated with OCT (2 and 5 mg/kg body wt/d), HEX (2 and 5 mg/kg body wt/d) and HMB (10 and 20 mg/kg body wt/d) via gavage. During treatment, these drugs will be mixed in 0.5% methylcellulose. Therefore, control animals will receive only 0.5% methylcellulose as vehicle. Six mice will be used in each group. Female mice (4-5 week old) will be randomly selected for any group. Experimental animals will be scored daily for 30 days by a masked investigator, as follows: 0, no clinical disease; 0.5, piloerection; 1, tail weakness; 1.5, tail paralysis; 2, hind limb weakness; 3, hind limb paralysis; 3.5, forelimb weakness; 4, forelimb paralysis; 5, moribund or death.

Relapsing EAE in 5B6 PLP-TCR Tg Mice.

$PLP_{139-151}$-specific 5B6 TCR Tg mice (provided by Prof. Vijay Kuchroo, Harvard Medical School, Boston, Mass.) will be used. Female Tg mice (4-5 weeks old) will be immunized with 10 µg of PLP139-151 in M. tuberculosis in IFA as described above. Mice will be treated with OCT (2 and 5 mg/kg body wt/d), HEX (2 and 5 mg/kg body wt/d) and HMB (10 and 20 mg/kg body wt/d) via gavage. During treatment, these drugs will be mixed in 0.5% methylcellulose. Therefore, control animals will receive only 0.5% methylcellulose as vehicle. Six mice will be used in each group. Female mice (4-5 week old) will be randomly selected for any group. Experimental animals will be scored daily for 30 days by a masked investigator.

Chronic EAE.

C57BL/6 mice will be immunized with 100 µg of MOG35-55 as described above. Mice will also receive two doses of pertussis toxin (150 ng/mouse) on 0 and 2 dpi. Mice will be treated with OCT (2 and 5 mg/kg body wt/d), HEX (2 and 5 mg/kg body wt/d) and HMB (10 and 20 mg/kg body wt/d) via gavage. During treatment, these drugs will be mixed in 0.5% methylcellulose. Therefore, control animals will receive only 0.5% methylcellulose as vehicle. Six mice will be used in each group. Female mice (4-5 week old) will be randomly selected for any group. Experimental animals will be scored daily for 30 days by a masked investigator.

Histological Microscopy.

On 14 dpi (first chronic phase), five mice from each of the following groups (control, EAE, EAE+HMB, and EAE+vehicle) will be anesthetized. After perfusion with phosphate buffered saline (PBS) (pH 7.4) and then with 4% (w/v) paraformaldehyde solution in PBS, cerebellum and whole spinal cord will be dissected out from each mouse. The tissues will be further fixed and then divided into halves: one-half will be used for histological staining and the other half will be used for myelin staining. For histological analysis, routine histology will be performed to obtain perivascular cuffing and morphological details of CNS tissues of EAE mice. Paraformaldehyde-fixed tissues will be embedded in paraffin, and serial sections (4 µm) will be cut. Sections will be stained with conventional H&E staining method. Digital images will be collected under bright-field setting using an ×40 objective. Slides will be assessed in a blinded fashion by three examiners for inflammation in different anatomical compartments (meninges and parenchyma). Inflammation will be scored using the following scale as described: for meninges and parenchyma: 0, no infiltrating cells; 1, few infiltrating cells; 2, numerous infiltrating cells; and 3, widespread infiltration. For vessels: 0, no cuffed vessel; 1, one or two cuffed vessels per section; 2, three to five cuffed vessels per section and 3, more than five cuffed vessels per section. At least six serial sections of each spinal cord from each of five mice per group will be scored and statistically analyzed by AN OVA.

Staining for Myelin.

Sections will be stained with Luxol fast blue for myelin. Slides will be assessed in a blinded fashion for demyelination by three examiners using the following scale: 0, normal white matter; 1, rare foci; 2, a few areas of demyelination; and 3, large areas of demyelination. At least six serial sections of each spinal cord from each of five mice per group will be scored and statistically analyzed by ANOVA.

Semi-Quantitative RT-PCR Analysis.

Total RNA will be isolated from splenic T cells and spinal cord by using the RNeasy mini kit (Qiagen, Valencia, Calif.) and from spleen and cerebellum by using the Ultraspec-II RNA reagent (Biotecx laboratories, Inc, Houston, Tex.) following manufacturer's protocol. To remove any contaminating genomic DNA, total RNA will be digested with DNase. Semi-quantitative RT-PCR will be carried out using a RT-PCR kit from Clonetech (Mountain View, Calif.). Briefly, 1 µg of total RNA will be reverse transcribed using oligo(dT) as primer and MMLV reverse transcriptase (Clontech) in a 20 µL reaction mixture. The resulting cDNA will be appropriately-diluted, and diluted cDNA will be amplified using Titanium Taq DNA polymerase and the following primers. Amplified products will be electrophoresed on a 1.8% agarose gels and visualized by ethidium bromide staining.

```
(SEQ ID NO: 1) iNOS:
Sense:
5'-CCCTTCCGAAGTTTCTGGCAGCAGC-3'

(SEQ ID NO: 2) Antisense:
5'-GGCTGTCAGAGCCTCGTGGCTTTGG-3'

(SEQ ID NO: 3) IL-1β:
Sense:
5'-CTCCATGAGCTTTGTACAAGG-3'

(SEQ ID NO: 4) Antisense:
5'-TGCTGATGTACCAGTTGGGG-3'

(SEQ ID NO: 5) MBP:
Sense:
5'-TGGAGAGATTCACCGAGGAGA-3'

(SEQ ID NO: 6) Antisense:
5'-TGAAGCTCGTCGGACTCTGAG-3'

(SEQ ID NO: 7) GAPDH:
Sense:
5'-GGTGAAGGTCGGTGTGAACG-3'

(SEQ ID NO: 8) Antisense:
5'-TTGGCTCCACCCTTCAAGTG-3'
```

The relative expression of each gene with respect to GAPDH will be measured after scanning the bands with a Fluor Chem 8800 Imaging System (Alpha Innotech, San Leandro, Calif.).

Real-time PCR analysis will be performed using the ABI-Prism7700 sequence detection system (Applied Biosystems, Foster City, Calif.). Briefly, reactions will be performed in a 96-well optical reaction plates on cDNA equivalent to 50 ng DNase-digested RNA in a volume of 25 µL, containing 12.5 µL TaqMan Universal Master mix and optimized concentrations of FAM-labeled probe, forward and reverse primers following the manufacturer's protocol. All primers and FAM-labeled probes for mouse genes and GAPDH will be obtained from Applied Biosystems. The mRNA expressions of respective genes will be normalized to the level of GAPDH mRNA. Data will be processed by the ABI Sequence Detection System 1.6 software and analyzed by ANOVA.

Flow Cytometry.

Two-color flow cytometry will be performed. Briefly, $1 \times 10^6$ lymph node cells (LNC) or splenocytes suspended in flow staining buffer will be incubated at 4° C. with appropriately diluted FITC-labeled Ab to CD4 for 30 min, washed, and re-suspended in fixation and permeabilization solution. Following incubation in dark for 30 min, cells will be washed, blocked with test Fc block (anti-mouse CD16/32) in permeabilization buffer, and subsequently incubated with appropriately diluted PE-labeled Abs to Foxp3 at 4° C. in the dark. After incubation, the cell suspension will be centrifuged, washed thrice, and re-suspended in flow staining buffer. The cells then will be analyzed through FACS (BD Biosciences, San Jose, Calif.). Cells will be gated based on morphological characteristics. Apoptotic and necrotic cells will not be accepted for FACS analysis.

OCT, HEX and HMB Will be Tested for Inhibition of Infiltration of Mononuclear Cells, Inflammation and Demyelination in the Spinal Cord of EAE. Infiltration of autoreactive T cells and associated mononuclear cells is a hallmark of EAE as well as MS. OCT, HEX and HMB treatment will be tested for attenuation of infiltration and inflammation in adoptively-transferred EAE mice. Mice receiving OCT, HEX and HMB from 8 dpt (onset of the acute phase) will be sacrificed on 16 dpt. H & E staining will be examined for widespread infiltration of inflammatory cells into the spinal cord of EAE mice verses HMB treated mice. The relative level of inflammatory cells will be quantitated.

OCT, HEX and HMB treatment will be examined to determine whether these drugs are capable of inhibiting the expression of proinflammatory molecules in the spinal cord of EAE mice. Expression of pro-inflammatory molecules like iNOS and IL-1β will be observed in the spinal cord of untreated EAE mice compared to control mice and HMB-treated mice.

Demyelination is the most important pathological feature in MS, which is also modeled in EAE animals. Therefore, it will be examined whether OCT, HEX and HMB treatment protects EAE mice from demyelination. Spinal cord sections will be stained by luxol fast blue (LFB) for myelin and observed for widespread demyelination zones in the white matter or restoration of myelin. To confirm these findings, the expression of three myelin genes, myelin basic protein (MBP) and proteolipid protein (PLP), will be examined.

Experiments will also be carried out testing HMB, HEX and/or OCT treatment in connection with Parkinson's disease (PD). Examples are described using HMB.

Animals and MPTP Intoxication.

Six- to eight-week old C57BL/6 mice will be used. For acute MPTP intoxication, mice will receive four intraperitoneal (i.p.) injections of MPTP-HCl (18 mg/kg of free base; Sigma Chemical Co., St. Louis, Mo.) in saline at 2-h intervals. Control animals will receive only saline.

HMB Treatment.

Mice will be treated with HMB (10 and 20 mg/kg body wt/d) via gavage. HMB will be mixed in 0.5% methylcellulose (MC) and from 3 h after the last injection of MPTP, mice will be gavaged with 100 µL HMB-mixed MC once daily using gavage needle. Therefore, control MPTP mice received only MC as vehicle.

Western Blot Analysis.

Immunoblot analysis for DJ-1 and TH will be carried out. Briefly, cell homogenates will be electrophoresed, proteins will be transferred onto a nitrocellulose membrane, and bands were visualized with an Odyssey infrared scanner after immunolabeling with respective primary antibodies followed by infra-red fluorophore-tagged secondary antibody (Invitrogen).

HPLC Analyses.

Striatal level of dopamine will be quantified in Complete Stand-Alone HPLC-ECD System EiCOMHTEC-500 (JM Science Inc., Grand Island, N.Y.). Briefly, mice will be sacrificed by cervical dislocation after 7 days of MPTP intoxication and their striata will be collected and immediately frozen in dry ice and stored at −80C until analysis. On the day of the analysis, tissues will be sonicated in 0.2M perchloric acid containing isoproterenol and resulting homogenates were centrifuged at 20,000×g for 15 min at 4 C. After pH adjustment and filtration, 10 µl of supernatant will be injected onto an Eicompak SC-3ODS column (Complete Stand-Alone HPLC-ECD System EiCOMHTEC-500 from JM Science Inc., Grand Island, N.Y.) and analyzed following the manufacturer's protocol.

Upregulation and/or maintenance of PD-related beneficial protein such as DJ-1 in the nigra during neurodegenerative insults may have therapeutic efficacy in PD. MPTP intoxication should decrease the level of DJ-1 in vivo in the nigra. Oral treatment of MPTP-intoxicated mice with HMB will be tested for protection of DJ-1 in the nigra. Protection of nigral tyrosine hydroxylase (TH) levels and dopamine (DA) levels in the striata will also be investigated after MPTP treatment in the presence and absence of HMB.

Future experiments will evaluate whether HMB treatment improves motor functions in MPTP-intoxicated mice. Male C57/BL6 mice will be intoxicated with MPTP and from 6 hours after the last injection of MPTP, the mice will receive HMB (10 and 20 mg/kg body weight/day) via gavage. The mice will be tested for motor functions (A, rotorod; B, movement time; C, number of movements; D, rest time; E, horizontal activity; F, total distance; G, rearing; and H, stereotypy) 7 days after the last injection of MPTP. The data will be means±SEM of six mice per group.

Additional experiments will be conducted to determine if HMB, HEX and/or OCT treatment protects hippocampal neurons and improves memory and learning in 5XFAD mice, an animal model for Alzheimer's disease. Briefly, six-month old male 5XFAD mice will be treated with OCT (2 and 5 mg/kg body wt/d), HEX (2 and 5 mg/kg body wt/d) and HMB (10 and 20 mg/kg body wt/d) via gavage. During treatment, these drugs will be mixed in 0.5% methylcellulose. Therefore, control animals will receive only 0.5% methylcellulose as vehicle. After 30 d of treatment, mice will be tested for Barnes maze, T maze and Novel Object Recognition. Conclusion will be drawn from analysis of at least six mice per group. Hippocampal sections will be also double-labeled for NeuN (marker of neuron) and TUNEL (marker of apoptosis). Results will represent analysis of two hippocampal sections of each of six mice per group.

Experiments will be also carried out in fibroblasts of patients of Batten disease, one of the lysosomal storage disorders. Fibroblasts of patients with late infantile Batten disease will be treated with OCT (1 and 2 µM), HEX (1 and 2 µM) and HMB (10 and 20 µM) for 24 h followed by measuring the activity of tripeptidyl peptidase 1 (TPP1) activity as described by us[19]. After drug treatment, cells will be also monitored for lysosomal biogenesis using Lysotracker as described by us[20].

In order to examine whether OCT, HEX and HMB can induce weight loss, obese (ob/ob) mice will be treated with OCT (2 and 5 mg/kg body wt/d), HEX (2 and 5 mg/kg body wt/d) and HMB (10 and 20 mg/kg body wt/d) via gavage. During treatment, these drugs will be mixed in 0.5% methylcellulose. Therefore, one group of animals will receive only 0.5% methylcellulose as vehicle. After a month of treatment, body weight will be monitored. Six mice will be used in each group.

The above Figures and disclosure are intended to be illustrative and not exhaustive. This description will suggest many variations and alternatives to one of ordinary skill in the art. All such variations and alternatives are intended to be encompassed within the scope of the attached claims. Those familiar with the art may recognize other equivalents to the specific embodiments described herein which equivalents are also intended to be encompassed by the attached claims.

REFERENCES

1. Issemann, I. & Green, S. Activation of a member of the steroid hormone receptor superfamily by peroxisome proliferators. *Nature* 347, 645-50 (1990).
2. Keller, H. et al. Fatty acids and retinoids control lipid metabolism through activation of peroxisome proliferator-activated receptor-retinoid X receptor heterodimers. *Proc Natl Acad Sci USA* 90, 2160-4 (1993).
3. Lehmann, J. M., Lenhard, J. M., Oliver, B. B., Ringold, G. M. & Kliewer, S. A. Peroxisome proliferator-activated receptors alpha and gamma are activated by indomethacin and other non-steroidal anti-inflammatory drugs. *J Biol Chem* 272, 3406-10 (1997).
4. Gocke, A. R. et al. Transcriptional modulation of the immune response by peroxisome proliferator-activated receptor-{alpha} agonists in autoimmune disease. *J Immunol* 182, 4479-87 (2009).
5. Cabrero, A. et al. Increased reactive oxygen species production down-regulates peroxisome proliferator-activated alpha pathway in C2C12 skeletal muscle cells. *J Biol Chem* 277, 10100-7 (2002).
6. Roy, A. et al. Regulation of cyclic AMP response element binding and
hippocampal plasticity-related genes by peroxisome proliferator-activated receptor alpha. *Cell Rep* 4, 724-37.
7. Fanelli, F. et al. Age-dependent roles of peroxisomes in the hippocampus of a transgenic mouse model of Alzheimer's disease. *Mol Neurodegener* 8, 8.
8. Chakravarthy, M. V. et al. Identification of a physiologically relevant endogenous ligand for PPARalpha in liver. *Cell* 138, 476-88 (2009).
9. Schoonjans, K. et al. Induction of the acyl-coenzyme A synthetase gene by fibrates and fatty acids is mediated by a peroxisome proliferator response element in the C promoter. *J Biol Chem* 270, 19269-76 (1995).
10. Kauer, J. A., Malenka, R. C. & Nicoll, R. A. NMDA application potentiates synaptic transmission in the hippocampus. *Nature* 334, 250-2 (1988).
11. Mulkey, R. M., Herron, C. E. & Malenka, R. C. An essential role for protein phosphatases in hippocampal long-term depression. *Science* 261, 1051-5 (1993).
12. Harris, K. M., Jensen, F. E. & Tsao, B. Three-dimensional structure of dendritic spines and synapses in rat hippocampus (CA1) at postnatal day 15 and
adult ages: implications for the maturation of synaptic physiology and long-term potentiation. *J Neurosci* 12, 2685-705 (1992).
13. Roy, A. et al. Enhancement of morphological plasticity in hippocampal neurons by a physically modified saline via phosphatidylinositol-3 kinase. *PLoS One* 9, e101883 (2014).
14. Chakravarthy, M. V. et al. Brain fatty acid synthase activates PPARalpha to maintain energy homeostasis. *J Clin Invest* 117, 2539-52 (2007).
15. Fu, J. et al. Oleylethanolamide regulates feeding and body weight through activation of the nuclear receptor PPAR-alpha. *Nature* 425, 90-3 (2003).
16. Cluny, N. L., Keenan, C. M., Lutz, B., Piomelli, D. & Sharkey, K. A. The identification of peroxisome proliferator-activated receptor alpha-independent effects of oleoylethanolamide on intestinal transit in mice. *Neurogastroenterol Motil* 21, 420-9 (2009).
17. Roy, A., Fung, Y. K., Liu, X. & Pahan, K. Up-regulation of microglial CD11b expression by nitric oxide. *J Biol Chem* 281, 14971-80 (2006).
18. Ghosh, A. et al. Selective inhibition of NF-kappaB activation prevents dopaminergic neuronal loss in a mouse model of Parkinson's disease. *Proc Natl Acad Sci USA* 104, 18754-9 (2007).
19. Ghosh, A. et al. Gemfibrozil and fenofibrate, Food and Drug Administration-approved lipid-lowering drugs, up-regulate tripeptidyl-peptidase 1 in brain cells via peroxisome proliferator-activated receptor α: implications for late infantile Batten disease therapy. *J. Biol. Chem.* 287, 38922-35 (2012).
20. Ghosh, A. et al. Gemfibrozil and fenofibrate, Food and Drug Administration-approved lipid-lowering drugs, up-regulate tripeptidyl-peptidase 1 in brain cells via peroxisome proliferator-activated receptor α: implications for late infantile Batten disease therapy. *J. Biol. Chem.* 290, 10309-24 (2015).
21. Corbett, G. T., Gonzalez, F. J. & Pahan, K. Activation of peroxisome proliferator-activated receptor alpha stimulates ADAM10-mediated proteolysis of APP. *Proc Natl Acad Sci USA* 112, 8445-50 (2015).
22. Gronemeyer, H., Gustafsson, J. A. & Laudet, V. Principles for modulation of the nuclear receptor superfamily. *Nat Rev Drug Discov* 3, 950-64 (2004).
23. Campolongo, P. et al. Fat-induced satiety factor oleoylethanolamide enhances memory consolidation. *Proc Natl Acad Sci USA* 106, 8027-31 (2009).
24. Fu, J., Oveisi, F., Gaetani, S., Lin, E. & Piomelli, D. Oleoylethanolamide, an endogenous PPAR-alpha agonist, lowers body weight and hyperlipidemia in obese rats. *Neuropharmacology* 48, 1147-53 (2005).
25. LoVerme, J., La Rana, G., Russo, R., Calignano, A. & Piomelli, D. The search for the palmitoylethanolamide receptor. *Life Sci* 77, 1685-98 (2005).
26. Fang, X. et al. 20-carboxy-arachidonic acid is a dual activator of peroxisome proliferator-activated receptors alpha and gamma. *Prostaglandins Other Lipid Mediat* 82, 175-84 (2007).

27. Narala, V. R. et al. Leukotriene B4 is a physiologically relevant endogenous peroxisome proliferator-activated receptor-alpha agonist. *J Biol Chem* 285, 22067-74 (2010).
28. Chen, L. et al. Oleoylethanolamide, an endogenous PPAR-alpha ligand, attenuates liver fibrosis targeting hepatic stellate cells. *Oncotarget* 6, 42530-40 (2015).
29. Mattace Raso, G. et al. N-Palmitoylethanolamide protects the kidney from hypertensive injury in spontaneously hypertensive rats via inhibition of oxidative stress. *Pharmacol Res* 76, 67-76 (2013).
30. Melis, M., Carta, G., Pistis, M. & Banni, S. Physiological role of peroxisome proliferator-activated receptors type alpha on dopamine systems. *CNS Neurol Disord Drug Targets* 12, 70-7 (2013).
31. Roy, A. et al. HMG-CoA Reductase Inhibitors Bind to PPARalpha to Upregulate Neurotrophin Expression in the Brain and Improve Memory in Mice. *Cell Metab* 22, 253-65 (2015).
32. Kainu, T., Wikstrom, A. C., Gustafsson, J. A. & Pelto-Huikko, M. Localization of the peroxisome proliferator-activated receptor in the brain. *Neuroreport* 5, 2481-5 (1994).
33. LoVerme, J., La Rana, G., Russo, R., Calignano, A. & Piomelli, D. The search for the palmitoylethanolamide receptor. *Life Sci* 77, 1685-98 (2005).
34. Huitron-Resendiz, S., Gombart, L., Cravatt, B. F. & Henriksen, S. J. Effect of oleamide on sleep and its relationship to blood pressure, body temperature, and locomotor activity in rats. *Exp Neurol* 172, 235-43 (2001).
35. Jana, M., Jana, A., Pal, U. & Pahan, K. A simplified method for isolating highly purified neurons, oligodendrocytes, astrocytes, and microglia from the same human fetal brain tissue. *Neurochem Res* 32, 2015-22 (2007).
36. Saha, R. N. et al. TNF-alpha preconditioning protects neurons via neuron-specific up-regulation of CREB-binding protein. *J Immunol* 183, 2068-78 (2009).
37. Gorini, A., D'Angelo, A. & Villa, R. F. Energy metabolism of synaptosomal subpopulations from different neuronal systems of rat hippocampus: effect of L-acetylcarnitine administration in vivo. *Neurochem Res* 24, 617-24 (1999).
38. Saha, R. N. & Pahan, K. Differential regulation of Mn-superoxide dismutase in neurons and astroglia by HIV-1 gp120: Implications for HIV-associated dementia. *Free Radic Biol Med* 42, 1866-78 (2007).
39. Giulian, D. & Baker, T. J. Characterization of ameboid microglia isolated from developing mammalian brain. *J Neurosci* 6, 2163-78 (1986).
40. Dasgupta, S., Jana, M., Liu, X. & Pahan, K. Role of very-late antigen-4 (VLA-4) in myelin basic protein-primed T cell contact-induced expression of proinflammatory cytokines in microglial cells. *J Biol Chem* 278, 22424-31 (2003).
41. Tripos International. 2011-2014 Certara, L. P. 210 N. Tucker Blvd, Suite 350, St. Louis Mo. 63101 (2011).
42. Im, W., Feig, M. & Brooks, C. L., 3rd. An implicit membrane generalized born theory for the study of structure, stability, and interactions of membrane proteins. *Biophys J* 85, 2900-18 (2003).

TABLE 1

Peak integration statistics of mass spectrometric analyses for HEX and OCT in Ppara-nuW hippocampal neurons infected with lentivirions containing different Ppara constructs.

| | Sample Name | Ion, m/z | Peak R.T, minutes | Adjusted peak area | Peak area of Int. Standard | Rel. Abundance (RA) | % RA |
|---|---|---|---|---|---|---|---|
| HEX ↑ | Vector Only | 255.01 | 13.71 | 17632 | 916408 | 0.019240338 | 1.92 |
| | FL-Ppara | 255.01 | 13.7 | 23806805 | 989368 | 24.06263898 | 2406 |
| | Y314D-Ppara | 255.23 | 13.7 | 637636 | 1710699 | 0.372734186 | 37.3 |
| | Y464D-Ppara | 255.01 | 13.72 | 18646 | 1149966 | 0.016214392 | 1.62 |
| ↓ | Y314D/Y464D-Ppara | 255.17 | 13.71 | 6843 | 575146 | 0.011897849 | 1.19 |
| OCT ↑ | Vector Only | 281.13 | 14.49 | 79623 | 916408 | 0.086885972 | 8.69 |
| | FL-Ppara | 280.97 | 14.5 | 24671057 | 989368 | 24.93617845 | 2494 |
| | Y314D-Ppara | 281.23 | 14.51 | 827358 | 1710699 | 0.48363739 | 48.4 |
| | Y464D-Ppara | 281.24 | 14.49 | 266871 | 1149966 | 0.2320686 | 23.2 |
| ↓ | Y314D/Y464D-Ppara | 281.05 | 14.49 | 128107 | 575146 | 0.222738226 | 22.3 |

Ppara-null hippocampal neurons were transduced with lentivirions containing different Ppara constructs for 48 h followed by the affinity purification through GFP column. After that, the eluted fraction was fractionated with the chloroform-methanol extraction procedure and the organic phase was analyzed by GCMS. Peaks for Hexadecanamide (HEX) and 9-octadecenamide (OCT) were analyzed and their detailed peak integration statistics were displayed above. Peak area was adjusted with baseline and then normalized with the peak area of the internal standard [2,4-Bis(αα-dimethylbenzyl)phenol]. The normalized value was shown as the relative abundance and finally presented in a percent scale.

TABLE 2

List of physiologically available possible nuclear ligands of PPARα in brain

| Class of Compounds | MW | Biosynthetic process | CAS Number |
|---|---|---|---|
| 3-Hydroxy-(2,2)-dimethyl butanoic acid, ethyl ester | 160.0 | Fatty acid Oxidation | 69737-23-1 |
| Thiosemicarbazones | 190-200 | Unknown | unknown |
| Thiazoles | 220-240 | Unknown | unknown |
| Thiazolidine esters | 250-270 | Unknown | unknown |
| Hexadecanamide | 255.01 | Very long chain Fatty acid β oxidation | 629-54-9 |
| 9-octadecenamide | 281.38 | Very long chain Fatty acid β oxidation | 301-02-0 |

The invention claimed is:

1. A method of modulating peroxisome proliferator-activated receptor α (PPARα) activity in a hippocampal neuronal cell in a subject in need thereof, the method comprising:
administering an effective amount of a PPARα ligand to the subject, wherein the PPARα ligand is hexadecanamide (HEX).

2. The method according to claim 1, comprising administering the effective amount of the PPARα ligand to a subject having dementia, a neurodegenerative disorder, a lysosomal storage disorder or obesity.

3. The method according to claim 2, wherein the neurodegenerative disorder is selected from the group consisting of Parkinson's disease, Alzheimer's disease, multiple sclerosis, Huntington's disease and HIV-associated dementia.

4. The method according to claim 2, wherein the lysosomal storage disorder is selected from the group consisting of Batten disease, Tay-Sach's disease, Farber's disease and Fabry's disease.

5. The method according to claim 1, wherein the effective amount of the PPARα ligand is delivered orally.

6. The method according to claim 1, wherein the effective amount of the PPARα ligand increases synaptic function in the subject.

7. The method according to claim 1, wherein the effective amount of the PPARα ligand upregulates calcium entry into hippocampal neuronal cells.

8. A method of treating a neurodegenerative disorder in a subject by modulating peroxisome proliferator-activated receptor a (PPARα) in a hippocampal neuronal cell, the method comprising administering an effective amount of a PPARα ligand to the subject, wherein the PPARα ligand is hexadecanamide (HEX), and the neurodegenerative disorder is selected from the group consisting of Parkinson's disease, Alzheimer's disease, multiple sclerosis, Huntington's disease and HIV-associated dementia.

9. A method of treating a lysosomal storage disorder in a subject by modulating peroxisome proliferator-activated receptor α (PPARα) in a hippocampal neuronal cell, the method comprising administering an effective amount of a PPARα ligand to the subject, wherein the PPARα ligand is hexadecanamide (HEX) and the lysosomal storage disorder is selected from the group consisting of Batten disease, Tay-Sach's disease, Farber's disease and Fabry's disease.

* * * * *

UNITED STATES PATENT AND TRADEMARK OFFICE
CERTIFICATE OF CORRECTION

PATENT NO. : 11,344,524 B2
APPLICATION NO. : 16/816524
DATED : May 31, 2022
INVENTOR(S) : Kalipada Pahan et al.

It is certified that error appears in the above-identified patent and that said Letters Patent is hereby corrected as shown below:

In the Claims

In Claim 8, Column 36, Line 37, after "receptor", please delete "a" and insert therefore --α--

Signed and Sealed this
Seventeenth Day of January, 2023

*Katherine Kelly Vidal*
*Director of the United States Patent and Trademark Office*